US012479908B2

(12) United States Patent
Conejo-Garcia et al.

(10) Patent No.: US 12,479,908 B2

(45) Date of Patent: Nov. 25, 2025

(54) ANTIBODIES AGAINST PROGRAMMED CELL DEATH PROTEIN 1 (PD1) AND USES THEREOF

(71) Applicant: H. LEE MOFFITT CANCER CENTER AND RESEARCH INSTITUTE, INC., Tampa, FL (US)

(72) Inventors: Jose Conejo-Garcia, Tampa, FL (US); Subir Biswas, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 916 days.

(21) Appl. No.: 17/599,875

(22) PCT Filed: Mar. 30, 2020

(86) PCT No.: PCT/US2020/025792

§ 371 (c)(1),
(2) Date: Sep. 29, 2021

(87) PCT Pub. No.: WO2020/205775

PCT Pub. Date: Oct. 8, 2020

(65) Prior Publication Data

US 2022/0204622 A1 Jun. 30, 2022

Related U.S. Application Data

(60) Provisional application No. 62/826,622, filed on Mar. 29, 2019.

(51) Int. Cl.

| | |
|---|---|
| ***C07K 16/00*** | (2006.01) |
| ***A61P 35/00*** | (2006.01) |
| ***C07K 16/10*** | (2006.01) |
| ***C07K 16/28*** | (2006.01) |
| *A61K 39/00* | (2006.01) |

(52) U.S. Cl.

CPC .............. *C07K 16/00* (2013.01); *A61P 35/00* (2018.01); *C07K 16/1003* (2023.08); *C07K 16/2818* (2013.01); *A61K 2039/505* (2013.01); *C07K 2317/21* (2013.01); *C07K 2317/34* (2013.01); *C07K 2317/52* (2013.01); *C07K 2317/54* (2013.01); *C07K 2317/73* (2013.01); *C07K 2317/77* (2013.01); *C07K 2319/03* (2013.01); *C07K 2319/32* (2013.01); *C07K 2319/33* (2013.01)

(58) Field of Classification Search

None

See application file for complete search history.

(56) References Cited

U.S. PATENT DOCUMENTS

2009/0017017 A1 1/2009 Rasmussen et al.
2012/0058906 A1 3/2012 Smider et al.

OTHER PUBLICATIONS

Liu, et al, Signal Transduction and Targeted Therapy, 2023, 8, 1-6 (Year: 2023).*

Rudikoff, et al., PNAS, 1982, 79, p. 1979-1983 (Year: 1982).*

Janeway, et al., Immunobiology: The Immune System in Health and Disease, 5th edition, 2001 (Year: 2001).*

Kanyavuz, et. al., Nat Rvw Immuno, 2019, 19, 355-368 (Year: 2019).*

Kipriyanov, et. al, Molecular Biotech, 2004, 26, 39-60 (Year: 2004).*

Twomey, et. al, AAPS Journal, 2021, 23, 1-11 (Year: 2021).*

International Search Report and Written Opinion in PCT/US2020/025792. Mailed Jul. 22, 2020. 9 pages.

Andreu, P. et al. FcRgamma activation regulates inflammation-associated squamous carcinogenesis. Cancer Cell 17, 121-134, doi:10.1016/j.ccr.2009.12.019 (2010).

Boland, J. L. et al. Early disease progression and treatment discontinuation in patients with advanced ovarian cancer receiving immune checkpoint blockade. Gynecol Oncol 152, 251-258, doi:10.1016/j.ygyno.2018.11.025 (2019).

Boyd, A. W., Bartlett, P. F. & Lackmann, M. Therapeutic targeting of EPH receptors and their ligands. Nat Rev Drug Discov 13, 39-62, doi:10.1038/nrd4175 (2014).

Brandtzaeg, P. Mucosal immunity in the female genital tract. J Reprod Immunol 36, 23-50 (1997).

Cardone, M. & Mostov, K. Wortmannin inhibits transcytosis of dimeric IgA by the polymeric immunoglobulin receptor. FEBS Lett 376, 74-76 (1995).

Conejo-Garcia, J. R. et al. Ovarian carcinoma expresses the NKG2D ligand Letal and promotes the survival and expansion of CD28-antitumor T cells. Cancer Res 64, 2175-2182 (2004).

Coukos, G., Conejo-Garcia, J. R., Roden, R. B. & Wu, T. C. Immunotherapy for gynaecological malignancies. Expert Opin Biol Ther 5, 1193-1210 (2005).

Counihan, N. A. & Anderson, D. A. Specific IgA Enhances the Transcytosis and Excretion of Hepatitis A Virus. Sci Rep 6, 21855, doi:10.1038/srep21855 (2016).

Cubillos-Ruiz, J. R. et al. CD277 is a Negative Co-stimulatory Molecule Universally Expressed by Ovarian Cancer Microenvironmental Cells. Oncotarget 1, 329-328 (2010).

Cubillos-Ruiz, J. R. et al. ER Stress Sensor XBP1 Controls Anti-tumor Immunity by Disrupting Dendritic Cell Homeostasis. Cell 161, 1527-1538, doi:10.1016/j.cell.2015.05.025 S0092-8674(15)00575-9 [pii] (2015).

(Continued)

*Primary Examiner* — Michael Szperka

*Assistant Examiner* — Samantha Lake Hopkins

(74) *Attorney, Agent, or Firm* — Meunier Carlin & Curfman LLC

(57) ABSTRACT

Disclosed herein are novel PD1 binding molecules and methods of their use.

12 Claims, 59 Drawing Sheets

Figures 1A, 1B:
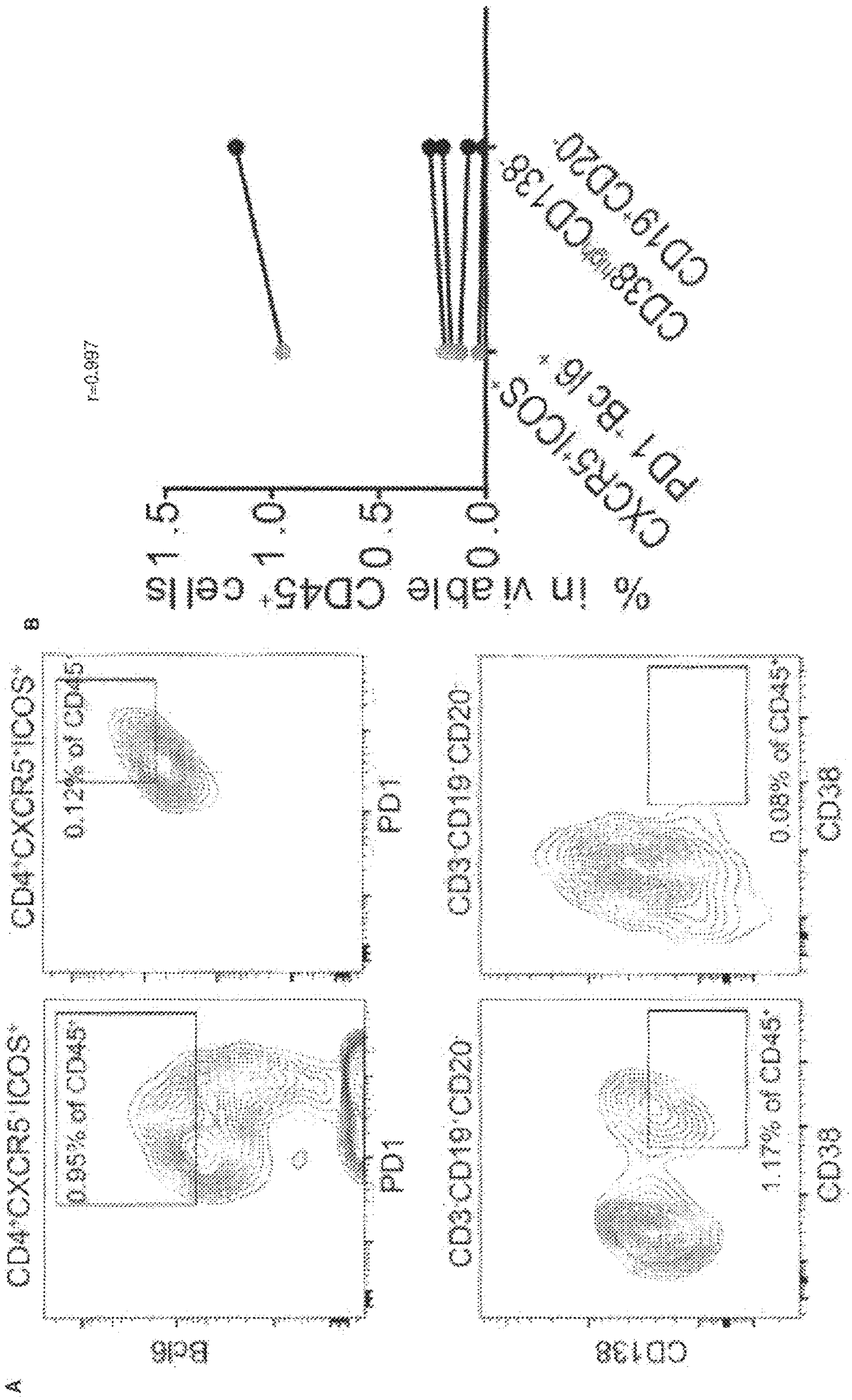

Specification includes a Sequence Listing.

(56) References Cited

OTHER PUBLICATIONS

Cubillos-Ruiz, J. R. et al. Polyethylenimine-based siRNA nanocomplexes reprogram tumor-associated dendritic cells via TLR5 to elicit therapeutic antitumor immunity. J Clin Invest 119, 2231-2244 (2009).
Curiel, T. J. et al. Blockade of B7-H1 improves myeloid dendritic cell-mediated antitumor immunity. Nat Med 9, 562-567, doi:10.1038/nm863 nm863 [pii] (2003).
Curiel, T. J. et al. Specific recruitment of regulatory T cells in ovarian carcinoma fosters immune privilege and predicts reduced survival. Nat Med 10, 942-949, doi:10.1038/nm1093 (2004).
Denton, A. E. et al. Type I interferon induces CXCL13 to support ectopic germinal center formation. J Exp Med 216, 621-637, doi:10.1084/jem.20181216 (2019).
Di Caro, G. et al. Occurrence of tertiary lymphoid tissue is associated with T-cell infiltration and predicts better prognosis in early-stage colorectal cancers. Clin Cancer Res 20, 2147-2158, doi:10.1158/1078-0432.CCR-13-2590 1078-0432.CCR-13-2590 [pii] (2014).
Dieu-Nosjean, M. C. et al. Tertiary lymphoid structures, drivers of the anti-tumor responses in human cancers. Immunol Rev 271, 260-275, doi:10.1111/imr.12405 (2016).
Figueiro, F. et al. Phenotypic and functional characteristics of CD39high human regulatory B cells (Breg). Oncoimmunology 5, e1082703, doi:10.1080/2162402X.2015.1082703 1082703 [pii] (2016).
Gelabert-Baldrich, M. et al. Dynamics of KRas on endosomes: involvement of acidic phospholipids in its association. FASEB J 28, 3023-3037, doi:10.1096/fj.13-241158 (2014).
Gu-Trantien, C. et al. CXCL13-producing TFH cells link immune suppression and adaptive memory in human breast cancer. JCI Insight 2, doi:10.1172/jci.insight.91487 (2017).
Hamanishi, J. et al. Programmed cell death 1 ligand 1 and tumor-infiltrating CD8+ T lymphocytes are prognostic factors of human ovarian cancer. Proc Natl Acad Sci U S A 104, 3360-3365 (2007).
Hamanishi, J., Mandai, M. & Konishi, I. Immune checkpoint inhibition in ovarian cancer. Int Immunol 28, 339-348, doi:10.1093/intimm/dxw020 dxw020 [pii] (2016).
Havenar-Daughton, C. et al. CXCL13 is a plasma biomarker of germinal center activity. Proc Natl Acad Sci U S A 113, 2702-2707, doi:10.1073/pnas.1520112113 (2016).
Helmink, B. A. et al. B cells and tertiary lymphoid structures promote immunotherapy response. Nature 577, 549-555, doi:10.1038/s41586-019-1922-8 (2020).
Hiraoka, N. et al. Intratumoral tertiary lymphoid organ is a favourable prognosticator in patients with pancreatic cancer. Br J Cancer 112, 1782-1790, doi:10.1038/bjc.2015.145 bjc2015145 [pii] (2015).
Huarte, E. et al. Depletion of dendritic cells delays ovarian cancer progression by boosting antitumor immunity. Cancer Res 68, 7684-7691, doi:0008-5472.CAN-08-1167 [pii] 10.1158/0008-5472.CAN-08-1167 (2008).
Huarte, E. et al. PILAR is a novel modulator of human T-cell expansion. Blood 112, 1259-1268 (2008).
Hung, C. F., Tsai, Y. C., He, L. & Wu, T. C. Control of mesothelin-expressing ovarian cancer using adoptive transfer of mesothelin peptide-specific CD8+ T cells. Gene Ther 14, 921-929, doi:10.1038/sj.gt.3302913 (2007).
Hunziker, W., Whitney, J. A. & Mellman, I. Selective inhibition of transcytosis by brefeldin A in MDCK cells. Cell 67, 617-627 (1991).
Jinushi, M., Hodi, F. S. & Dranoff, G. Therapy-induced antibodies to MHC class I chain-related protein A antagonize immune suppression and stimulate antitumor cytotoxicity. Proc Natl Acad Sci U S A 103, 9190-9195, doi:10.1073/pnas.0603503103 (2006).
Kroeger, D. R., Milne, K. & Nelson, B. H. Tumor-Infiltrating Plasma Cells are Associated with Tertiary Lymphoid Structures, Cytolytic T-Cell Responses, and Superior Prognosis in Ovarian Cancer. Clin Cancer Res 22, 3005-3015, doi:10.1158/1078-0432.CCR-15-2762 1078-0432.CCR-15-2762 [pii] (2016).
Kryczek, I. et al. B7-H4 expression identifies a novel suppressive macrophage population in human ovarian carcinoma. J Exp Med 203, 871-881 (2006).
Labidi-Galy, S. I. et al. High grade serous ovarian carcinomas originate in the fallopian tube. Nat Commun 8, 1093, doi:10.1038/s41467-017-00962-1 (2017).
Ladanyi, A. et al. Density of DC-LAMP(+) mature dendritic cells in combination with activated T lymphocytes infiltrating primary cutaneous melanoma is a strong independent prognostic factor. Cancer Immunol Immunother 56, 1459-1469, doi:10.1007/s00262-007-0286-3 (2007).
Lee, K. E. et al. Hif1a Deletion Reveals Pro-Neoplastic Function of B Cells in Pancreatic Neoplasia. Cancer Discov 6, 256-269, doi:10.1158/2159-8290.CD-15-0822 (2016).
Li Chew, C. et al. In Vivo Role of INPP4B in Tumor and Metastasis Suppression through Regulation of PI3K-AKT Signaling at Endosomes. Cancer Discov 5, 740-751, doi:10.1158/2159-8290.CD-14-1347 (2015).
Mazanec, M. B., Kaetzel, C. S., Lamm, M. E., Fletcher, D. & Nedrud, J. G. Intracellular neutralization of virus by immunoglobulin A antibodies. Proc Natl Acad Sci U S A 89, 6901-6905 (1992).
McMullen, T. P., Lai, R., Dabbagh, L., Wallace, T. M. & de Gara, C. J. Survival in rectal cancer is predicted by T cell infiltration of tumour-associated lymphoid nodules. Clin Exp Immunol 161, 81-88, doi:10.1111/j.1365-2249.2010.04147.x CEI4147 [pii] (2010).
Messina, J. L. et al. 12-Chemokine gene signature identifies lymph node-like structures in melanoma: potential for patient selection for immunotherapy? Sci Rep 2, 765, doi:10.1038/srep00765 (2012).
Montfort, A. et al. A Strong B-cell Response Is Part of the Immune Landscape in Human High-Grade Serous Ovarian Metastases. Clin Cancer Res 23, 250-262, doi:10.1158/1078-0432.CCR-16-0081 (2017).
Murphy, J. E., Padilla, B. E., Hasdemir, B., Cottrell, G. S. & Bunnett, N. W. Endosomes: a legitimate platform for the signaling train. Proc Natl Acad Sci U S A 106, 17615-17622, doi:10.1073/pnas.0906541106 (2009).
Mysona, D. et al. A combined score of clinical factors and serum proteins can predict time to recurrence in high grade serous ovarian cancer. Gynecol Oncol 152, 574-580, doi:10.1016/j.ygyno.2018.12.015 (2019).
Nielsen, J. S. et al. CD20+ tumor-infiltrating lymphocytes have an atypical CD27-memory phenotype and together with CD8+ T cells promote favorable prognosis in ovarian cancer. Clin Cancer Res 18, 3281-3292, doi:10.1158/1078-0432.CCR-12-0234 1078-0432.CCR-12-0234 [pii] (2012).
Park, B. V. et al. TGFbeta1-Mediated SMAD3 Enhances PD-1 Expression on Antigen-Specific T Cells in Cancer. Cancer Discov 6, 1366-1381, doi:10.1158/2159-8290.CD-15-1347 (2016).
Patterson, K. I., Brummer, T., O'Brien, P. M. & Daly, R. J. Dual-specificity phosphatases: critical regulators with diverse cellular targets. Biochem J 418, 475-489, doi:10.1042/bj20082234 (2009).
Perales-Puchalt, A. et al. Follicle-Stimulating Hormone Receptor Is Expressed by Most Ovarian Cancer Subtypes and Is a Safe and Effective Immunotherapeutic Target. Clin Cancer Res 23, 441-453, doi:10.1158/1078-0432.CCR-16-0492 (2017).
Redjimi, N. et al. NY-ESO-1-specific circulating CD4+ T cells in ovarian cancer patients are prevalently T(H)1 type cells undetectable in the CD25+ FOXP3+ Treg compartment. PLoS One 6, e22845, doi:10.1371/journal.pone.0022845 PONE-D-11-05345 [pii] (2011). Oct. 1, 2019.
Robbins, P. F. et al. Tumor regression in patients with metastatic synovial cell sarcoma andgenetically engineered lymphocytes reactive with NY-ESO-1. J Clin Oncol 29, 917-924, doi:10.1200/JCO.2010.32.2537 (2011).
Romanska, H. M. & Berditchevski, F. Tetraspanins in human epithelial malignancies. J Pathol 223, 4-14, doi:10.1002/path.2779 (2011).
Rutkowski, M. R. et al. Microbially driven TLR5-dependent signaling governs distal malignant progression through tumor-promoting inflammation. Cancer Cell 27, 27-40, doi:10.1016/j.ccell.2014.11.009 S1535-6108(14)00460-7 [pii] (2015).

(56) References Cited

OTHER PUBLICATIONS

Sato, E. et al. Intraepithelial CD8+ tumor-infiltrating lymphocytes and a high CD8+/regulatory T cell ratio are associated with favorable prognosis in ovarian cancer. Proc Natl Acad Sci U S A 102, 18538-18543 (2005).

Scarlett, U. K. et al. In situ stimulation of CD40 and Toll-like receptor 3 transforms ovarian cancer-infiltrating dendritic cells from immunosuppressive to immunostimulatory cells. Cancer Res 69, 7329-7337, doi:0008-5472.CAN-09-0835 [pii] 10.1158/0008-5472.CAN-09-0835 (2009).

Scarlett, U. K. et al. Ovarian cancer progression is controlled by phenotypic changes in dendritic cells. J Exp Med 209, 495-506, doi:jem.20111413 [pii] 10.1084/jem.20111413 (2012).

Schwartz-Cornil, I., Benureau, Y., Greenberg, H., Hendrickson, B. A. & Cohen, J. Heterologous protection induced by the inner capsid proteins of rotavirus requires transcytosis of mucosal immunoglobulins. J Virol 76, 8110-8117 (2002).

Shalapour, S. et al. Inflammation-induced IgA+ cells dismantle anti-liver cancer immunity. Nature 551, 340-345, doi:10.1038/nature24302 (2017).

Shen, M., Sun, Q., Wang, J., Pan, W. & Ren, X. Positive and negative functions of B lymphocytes in tumors. Oncotarget, doi:10.18632/oncotarget.10094 10094 [pii] (2016).

Stavnezer, J. & Kang, J. The surprising discovery that TGF beta specifically induces the IgA class switch. J Immunol 182, 5-7 (2009).

Stephen, T. L. et al. SATB1 Expression Governs Epigenetic Repression of PD1 in Tumor-Reactive T Cells. Immunity 46, 51-64, doi:10.1016/j.immuni.2016.12.015 (2017).

Stephen, T. L. et al. Transforming Growth Factor beta-Mediated Suppression of Antitumor T Cells Requires FoxP1 Transcription Factor Expression. Immunity 41, 427-439, doi:10.1016/j.immuni.2014.08.012 S1074-7613(14)00306-9 [pii] (2014).

Teillaud, J. L. & Dieu-Nosjean, M. C. Tertiary Lymphoid Structures: An Anti-tumor School for Adaptive Immune Cells and an Antibody Factory to Fight Cancer? Front Immunol 8, 830, doi:10.3389/fimmu.2017.00830 (2017).

Tesone, A. J. et al. Satb1 Overexpression Drives Tumor-Promoting Activities in Cancer-Associated Dendritic Cells. Cell Rep 14, 1774-1786, doi:10.1016/j.celrep.2016.01.056 (2016).

Turula, H. & Wobus, C. E. The Role of the Polymeric Immunoglobulin Receptor and Secretory Immunoglobulins during Mucosal Infection and Immunity. Viruses 10, doi:10.3390/v10050237 (2018).

Wirsing, A. M., Rikardsen, O. G., Steigen, S. E., Uhlin-Hansen, L. & Hadler-Olsen, E. Characterisation and prognostic value of tertiary lymphoid structures in oral squamous cell carcinoma. BMC Clin Pathol 14, 38, doi:10.1186/1472-6890-14-38 1472-6890-14-38 [pii] (2014).

Wu, X. et al. Combined Anti-VEGF and Anti-CTLA-4 Therapy Elicits Humoral Immunity to Galectin-1 Which Is Associated with Favorable Clinical Outcomes. Cancer Immunol Res 5, 446-454, doi:10.1158/2326-6066.CIR-16-0385 (2017).

Xiao, X. et al. PD1hi Identifies a Novel Regulatory B-cell Population in Human Hepatoma That Promotes Disease Progression. Cancer Discov 6, 546-559, doi:10.1158/2159-8290.CD-15-1408 2159-8290.CD-15-1408 [pii] (2016).

Yokokawa, J. et al. Identification of novel human CTL epitopes and their agonist epitopes of mesothelin. Clin Cancer Res 11, 6342-6351, doi:11/17/6342 [pii] 10.1158/1078-0432.CCR-05-0596 (2005).

Zhang, L. et al. Intratumoral T cells, recurrence, and survival in epithelial ovarian cancer. N Engl J Med 348, 203-213 (2003).

Zou, W. et al. Stromal-derived factor-1 in human tumors recruits and alters the function of plasmacytoid precursor dendritic cells. Nat Med 7, 1339-1346, doi:10.1038/nm1201-1339 nm1201-1339 [pii] (2001).

* cited by examiner

A

B

B

C

E

J

Figure 9:
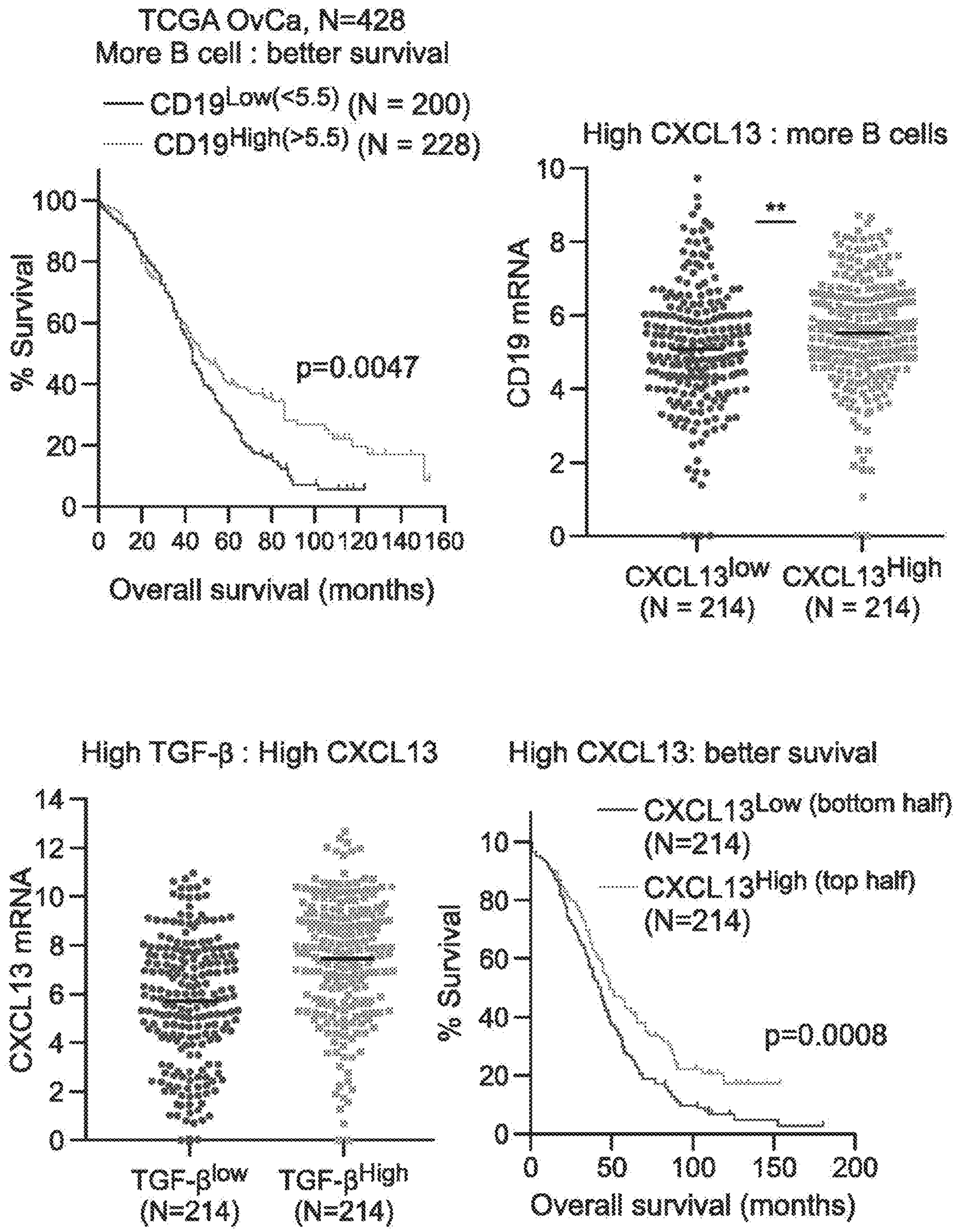

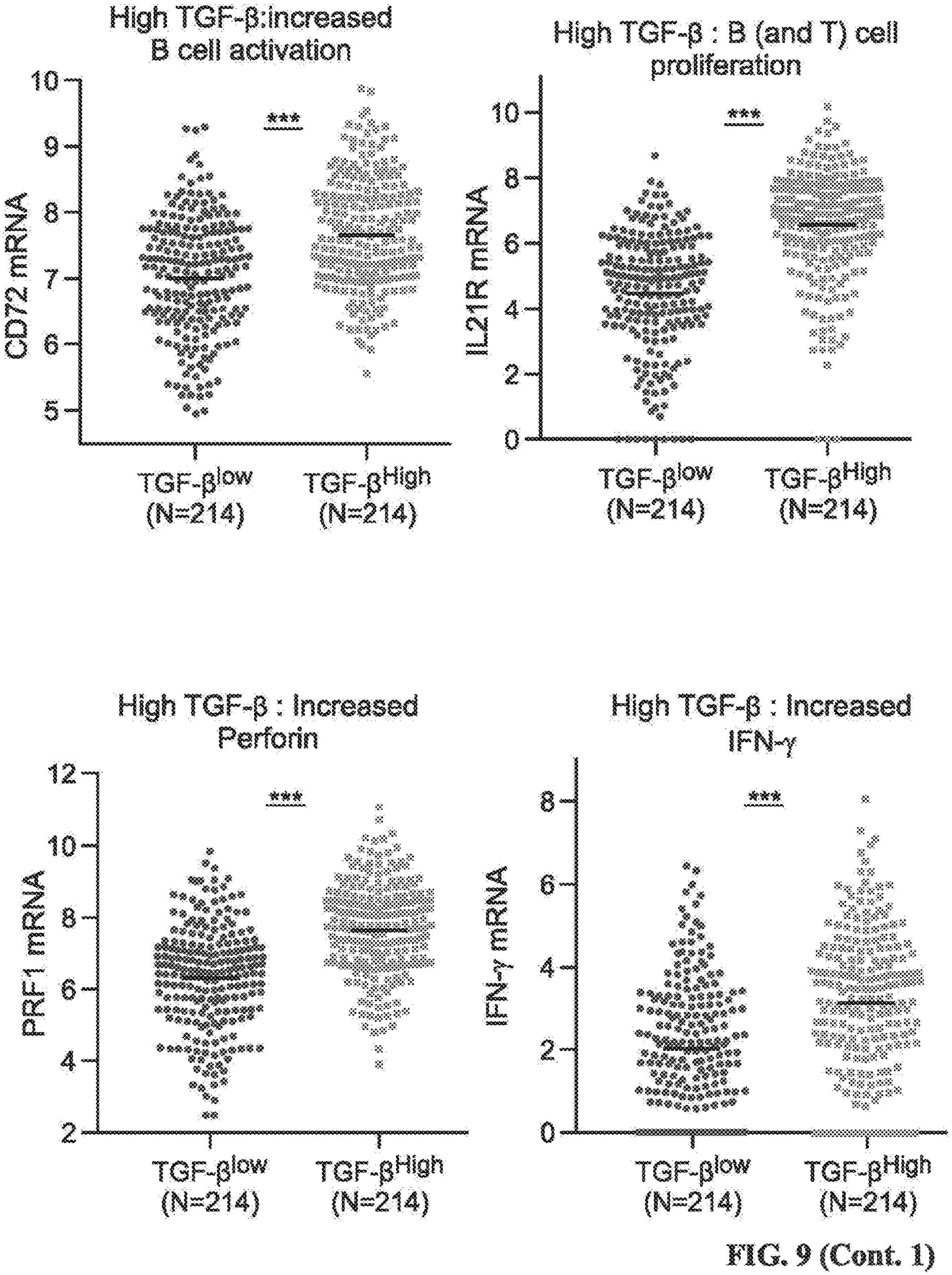
FIG. 9 (Cont. 1)

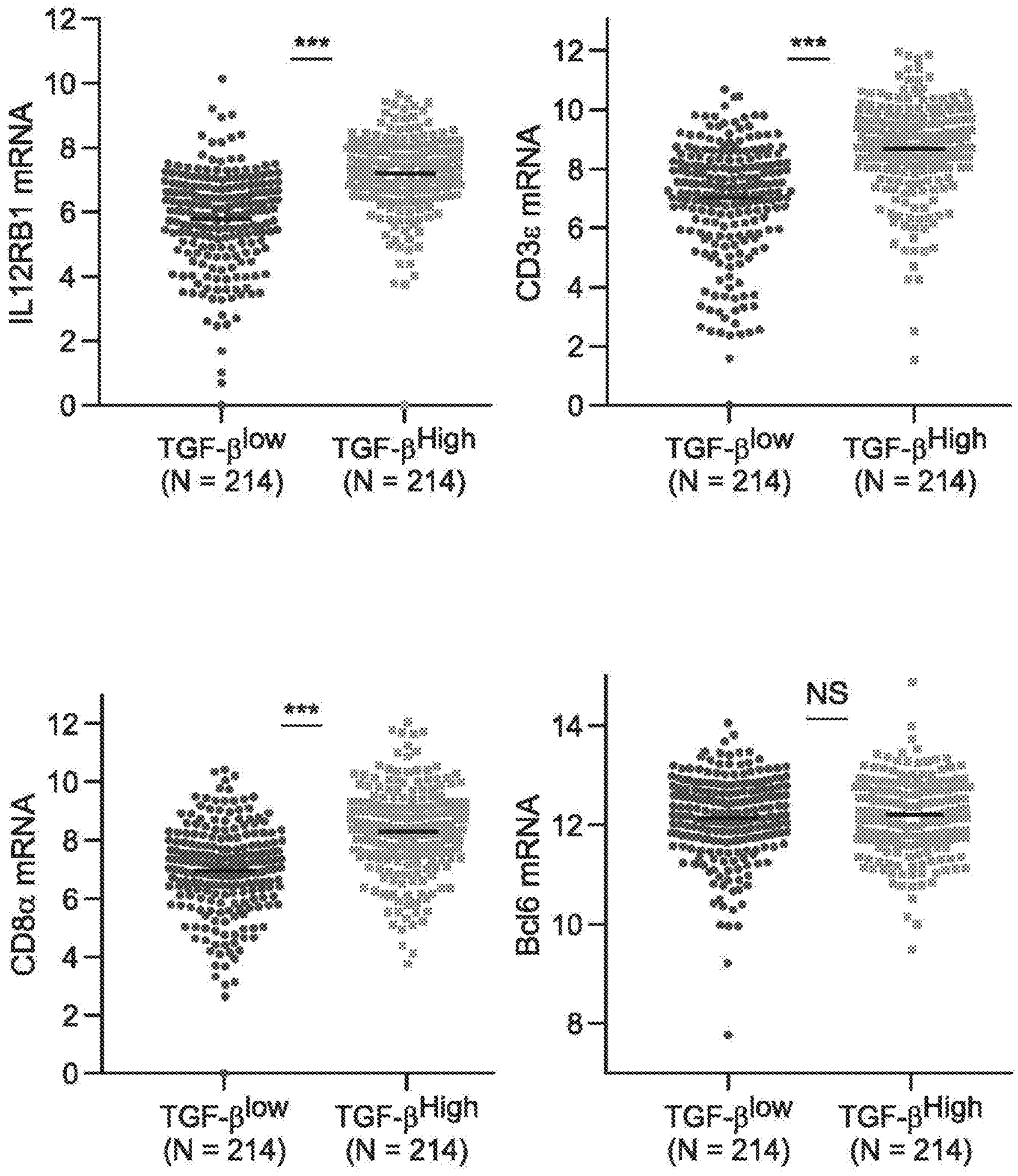
FIG. 9 (Cont. 2)

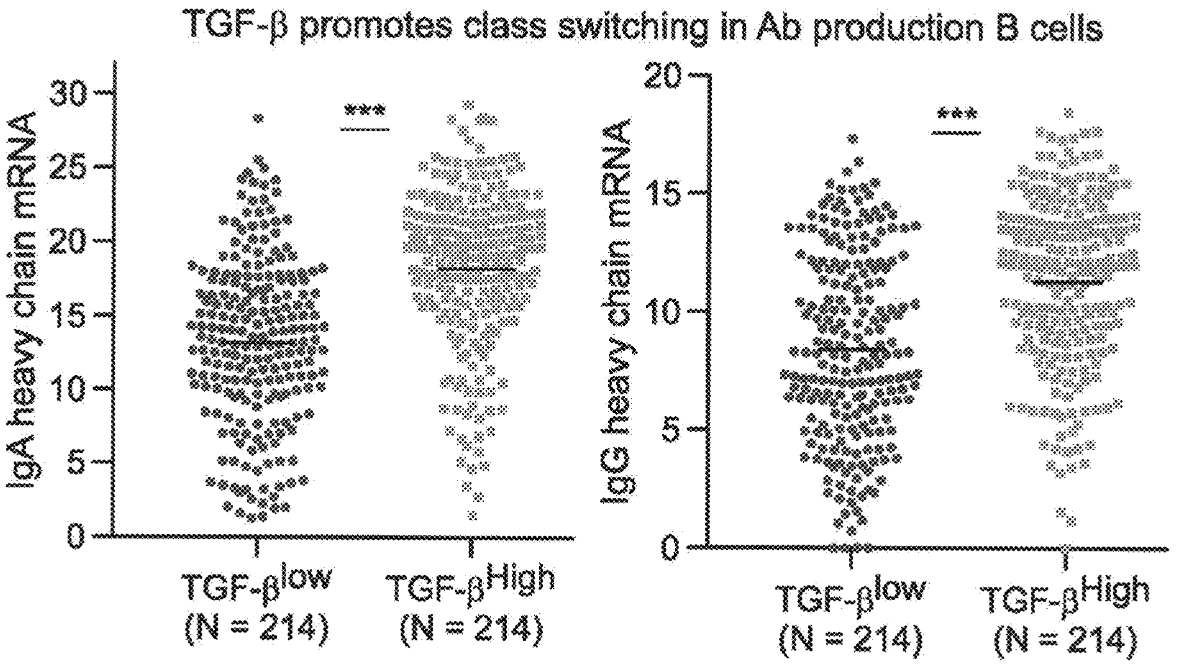
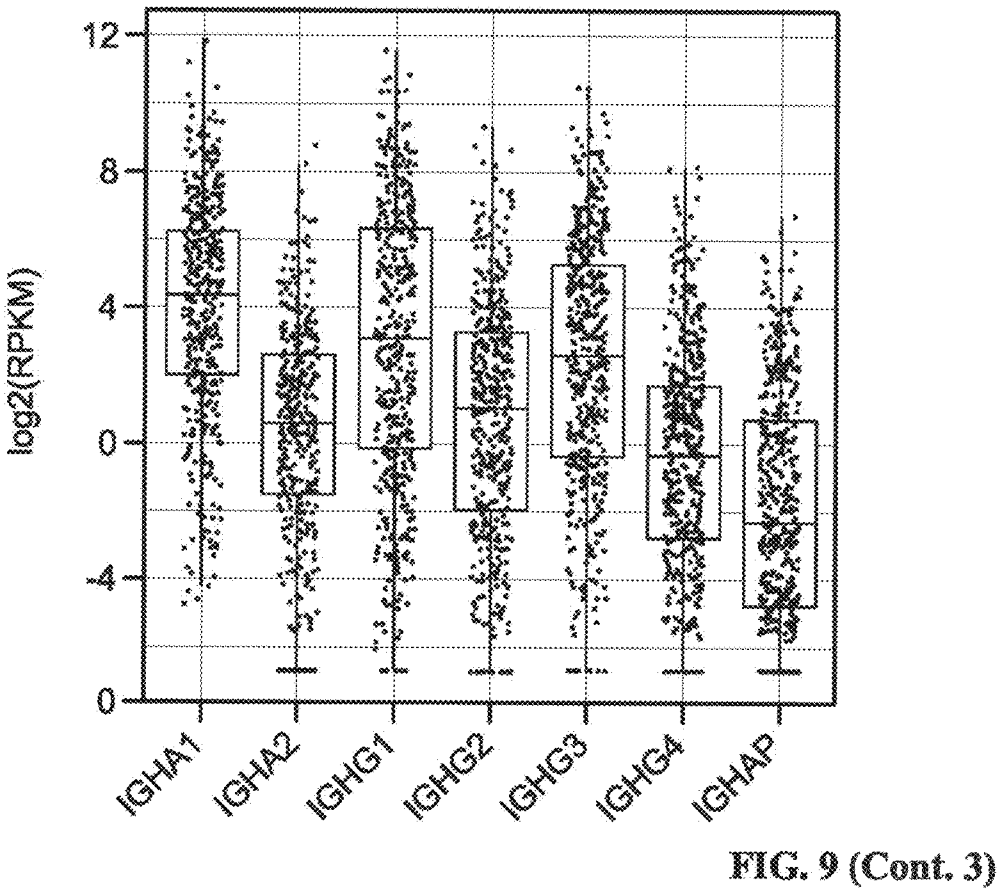
FIG. 9 (Cont. 3)

C

D

F

G

H

I

J

K

Figure 16A:
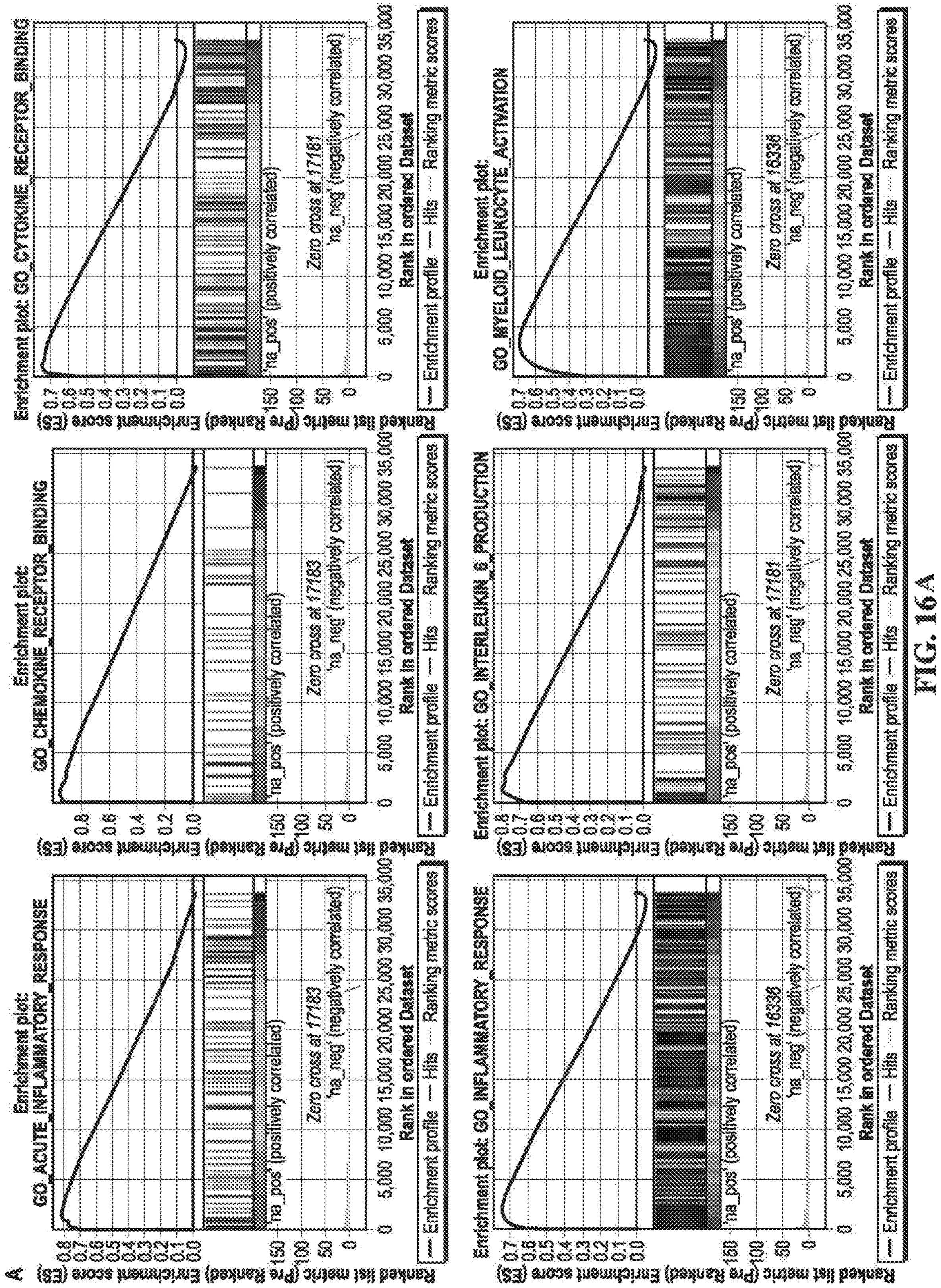

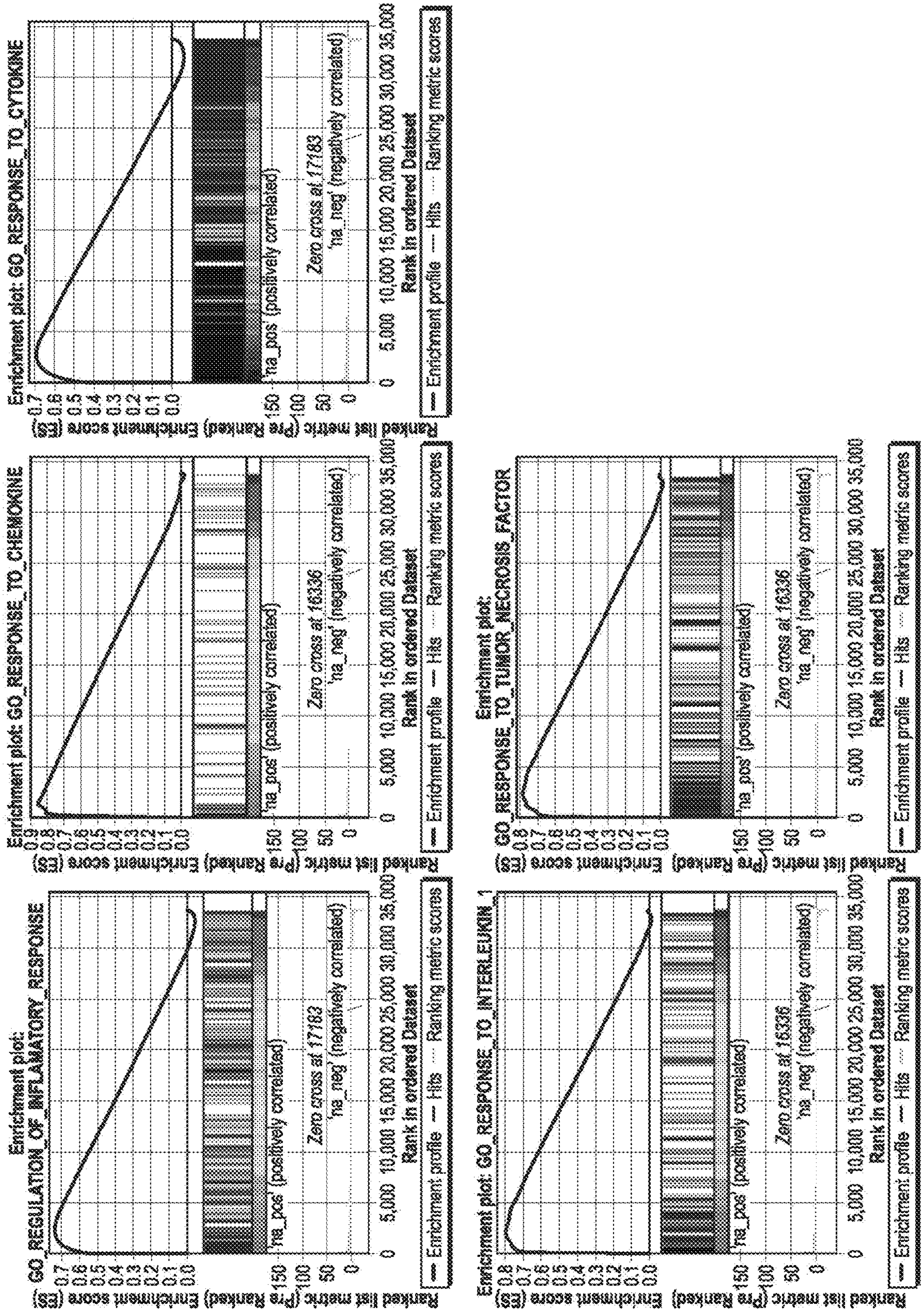
FIG. 16 A (Cont. 1)

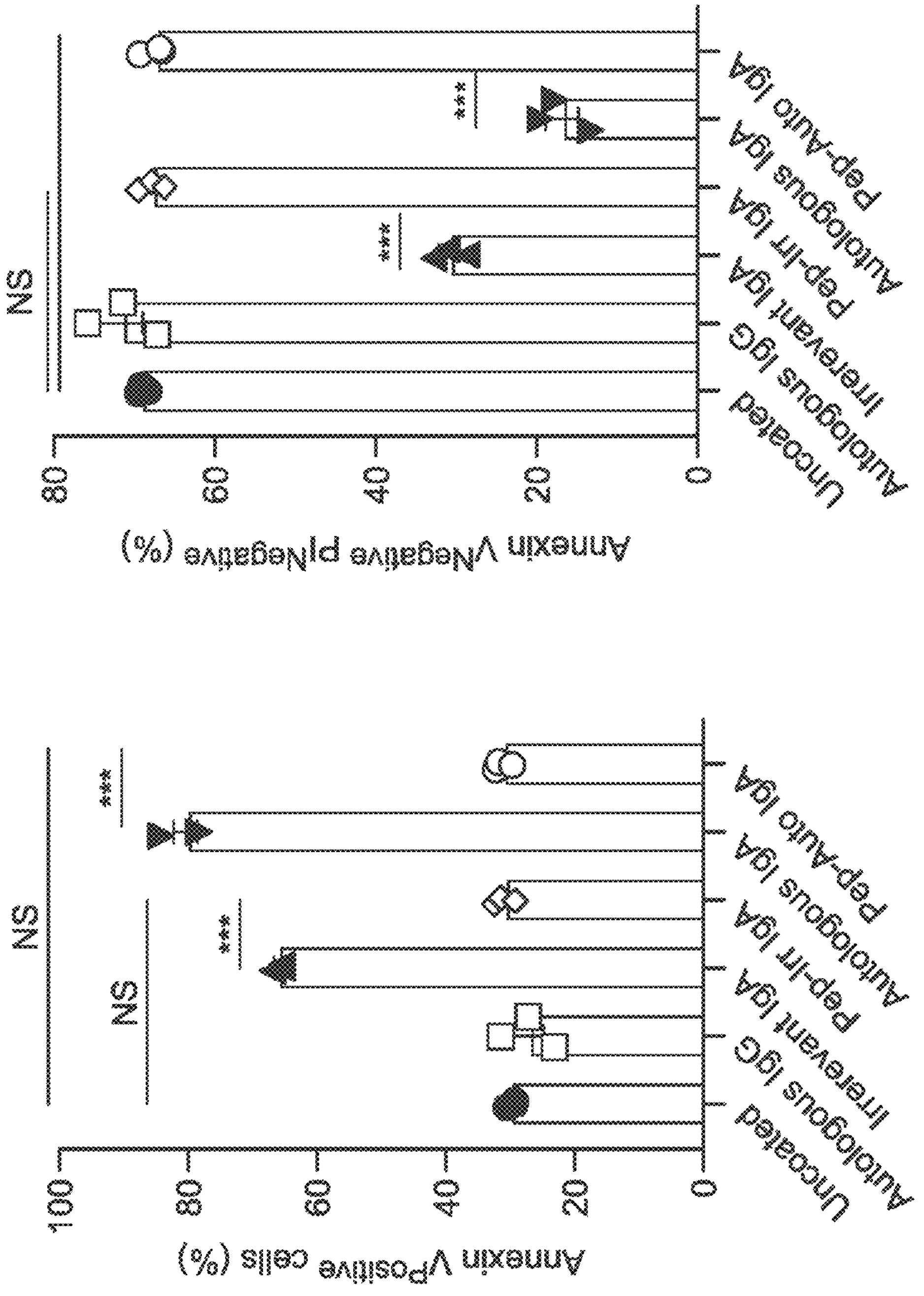
FIG. 17 B (Cont. 1)

G

H

E

| Sample | CDR3 | % in TLS |
|---|---|---|
| 1 | CARGRSSSSYYMDVW | 74.8% |
| 1 | CARASVPAPITGTIIWFDPW | 14.1% |
| 2 | CARVESYPSEYYYFGMDVW | 73.2% |
| 2 | CATTYSSSSGFDCW | 24.5% |
| 3 | CARASVPAPITGTIIWFDPW | 40.8% |
| 3 | CARGRSSSSYYMDVW | 30.2% |
| 3 | CTHDWRNW | 21.6% |
| 4 | CVKSAGRTSASPSYYYMDVW | 35.6% |
| 4 | CARGRGRDCRSSNCYYMDVW | 28.6% |
| 4 | CARGRSSSSYYMDVW | 28.2% |

Figures 25A, 25B:
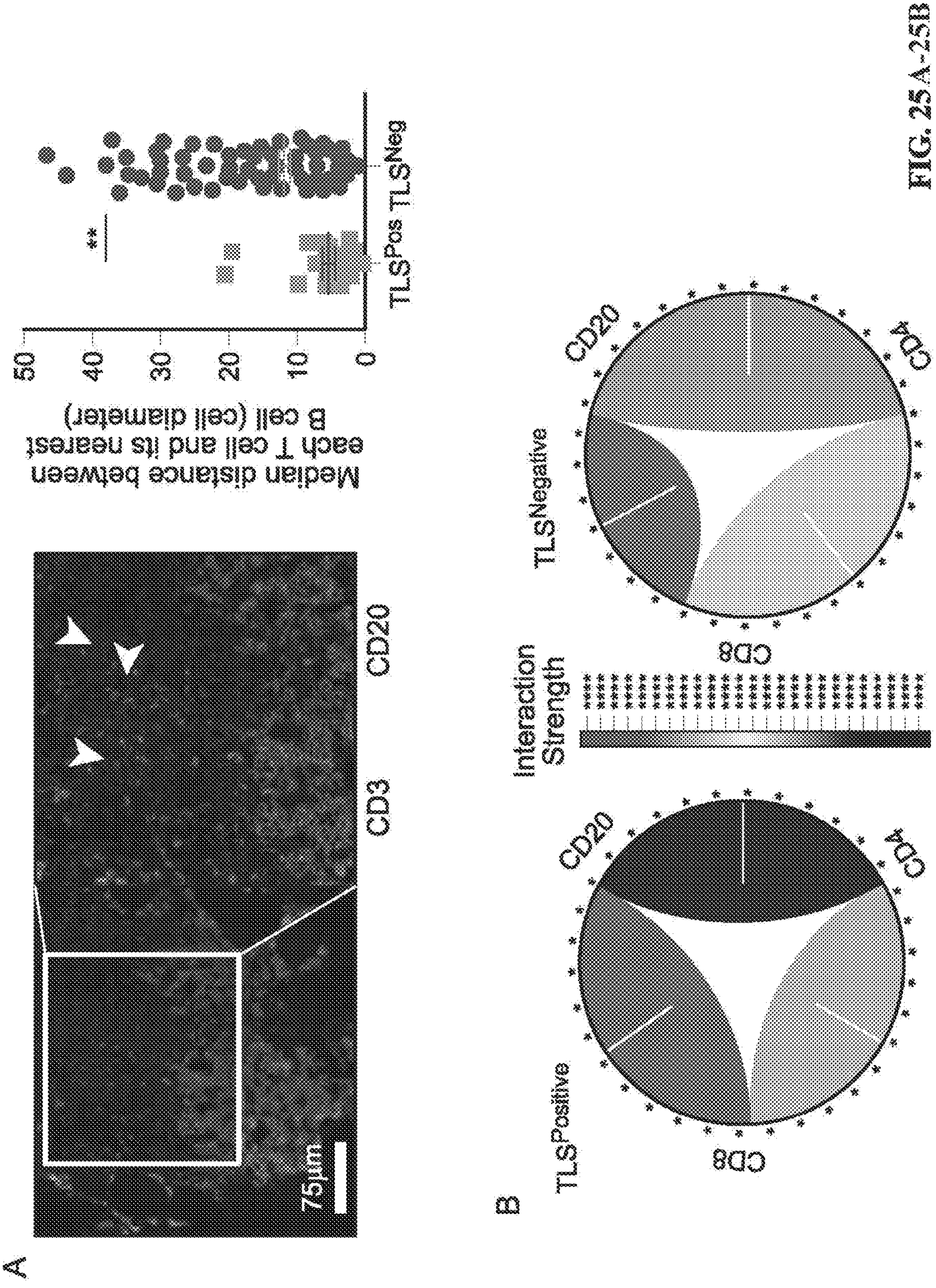
Figures 25C, 25D:
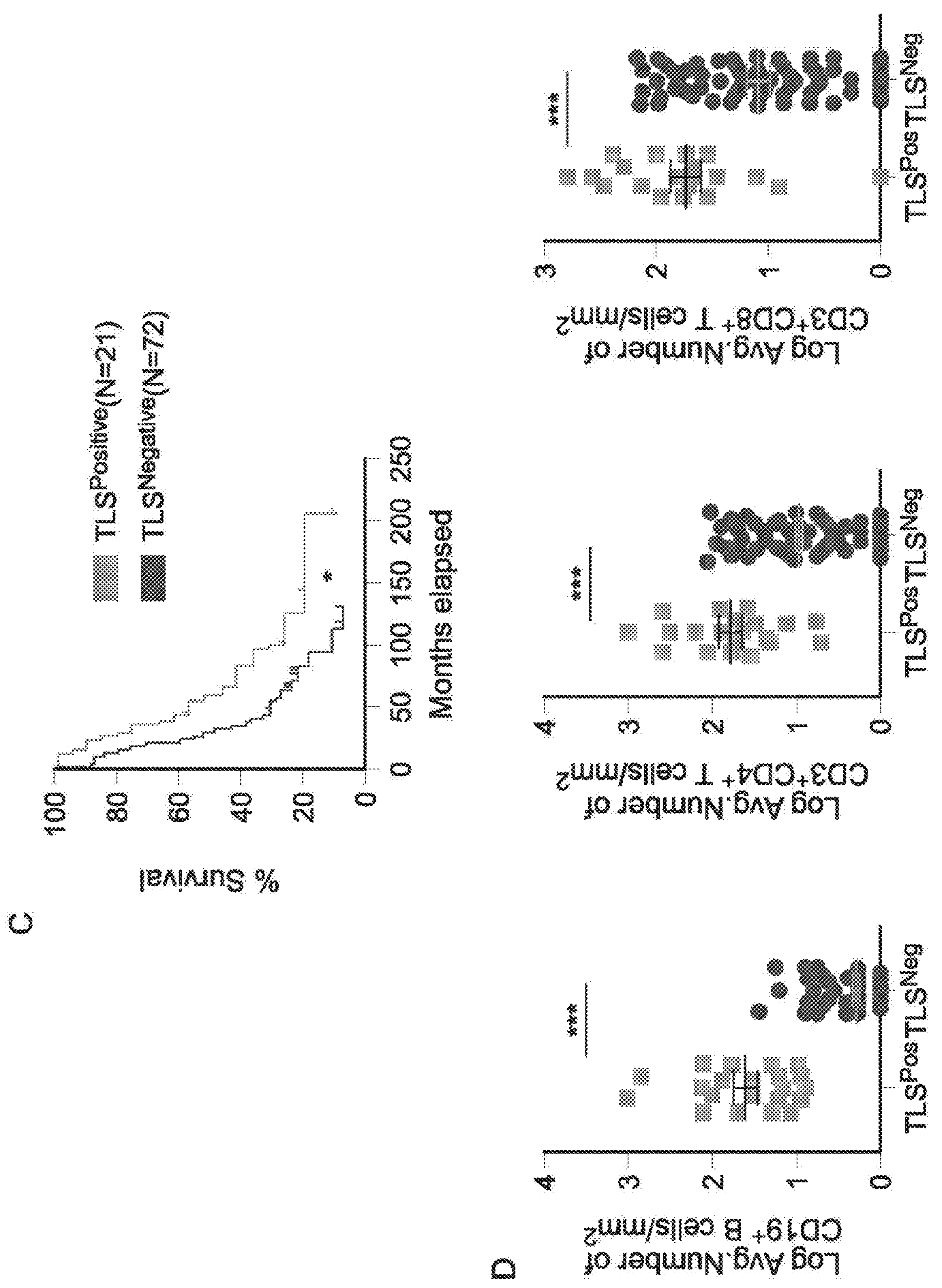
Figure 25E:
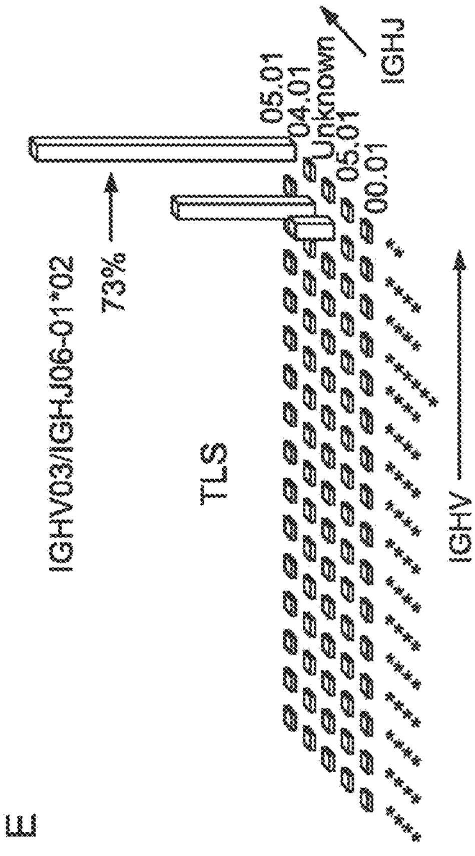
Figure 25E:
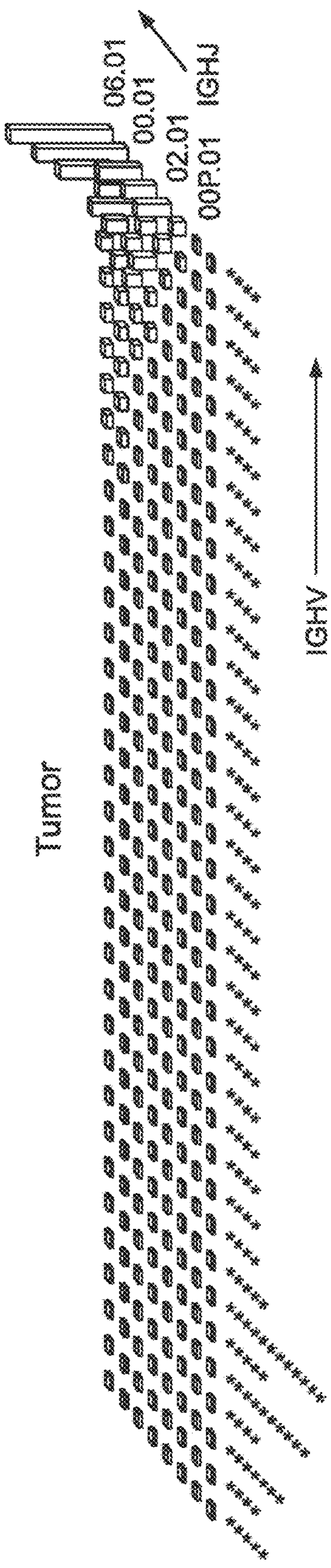
Figure 25:
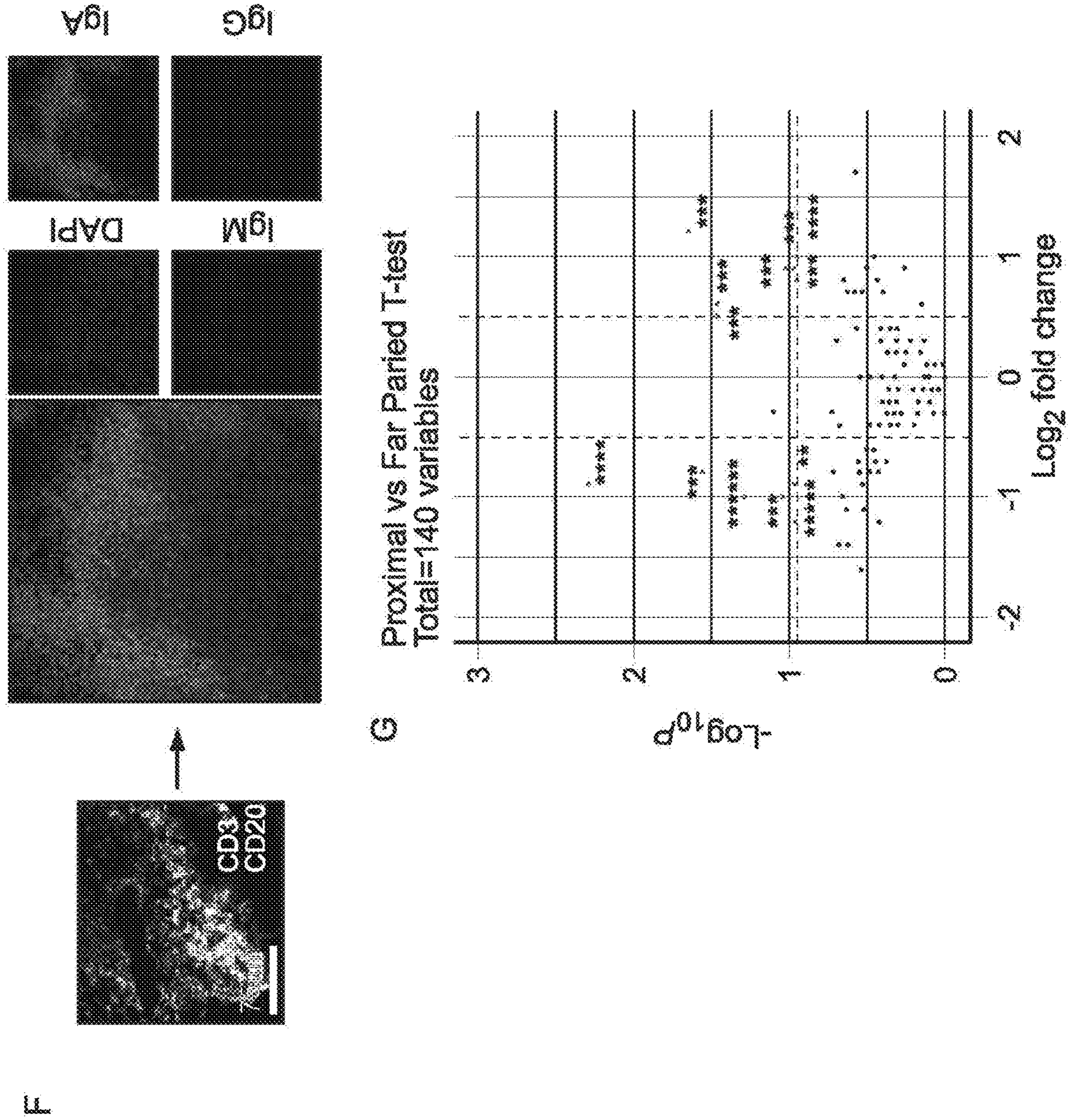

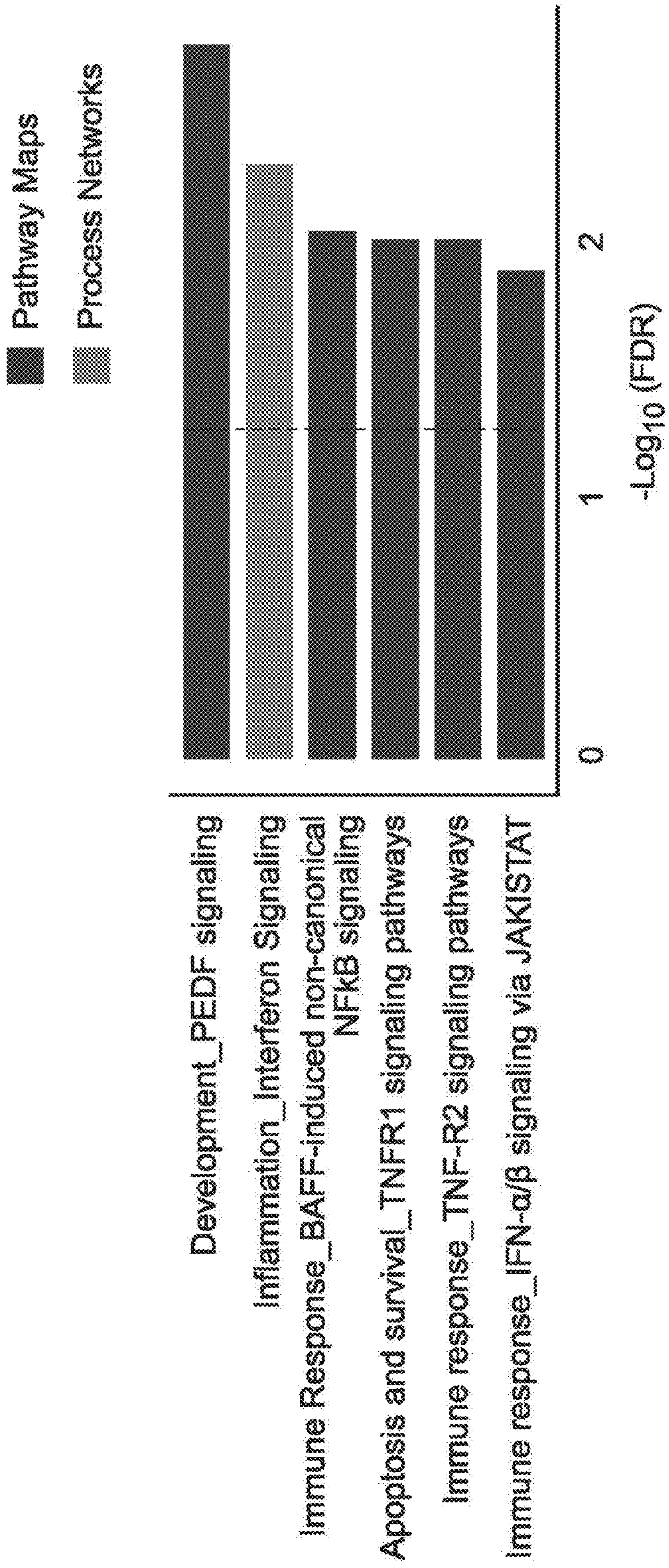
FIG. 25 G (Cont. 1)

Figure 26:
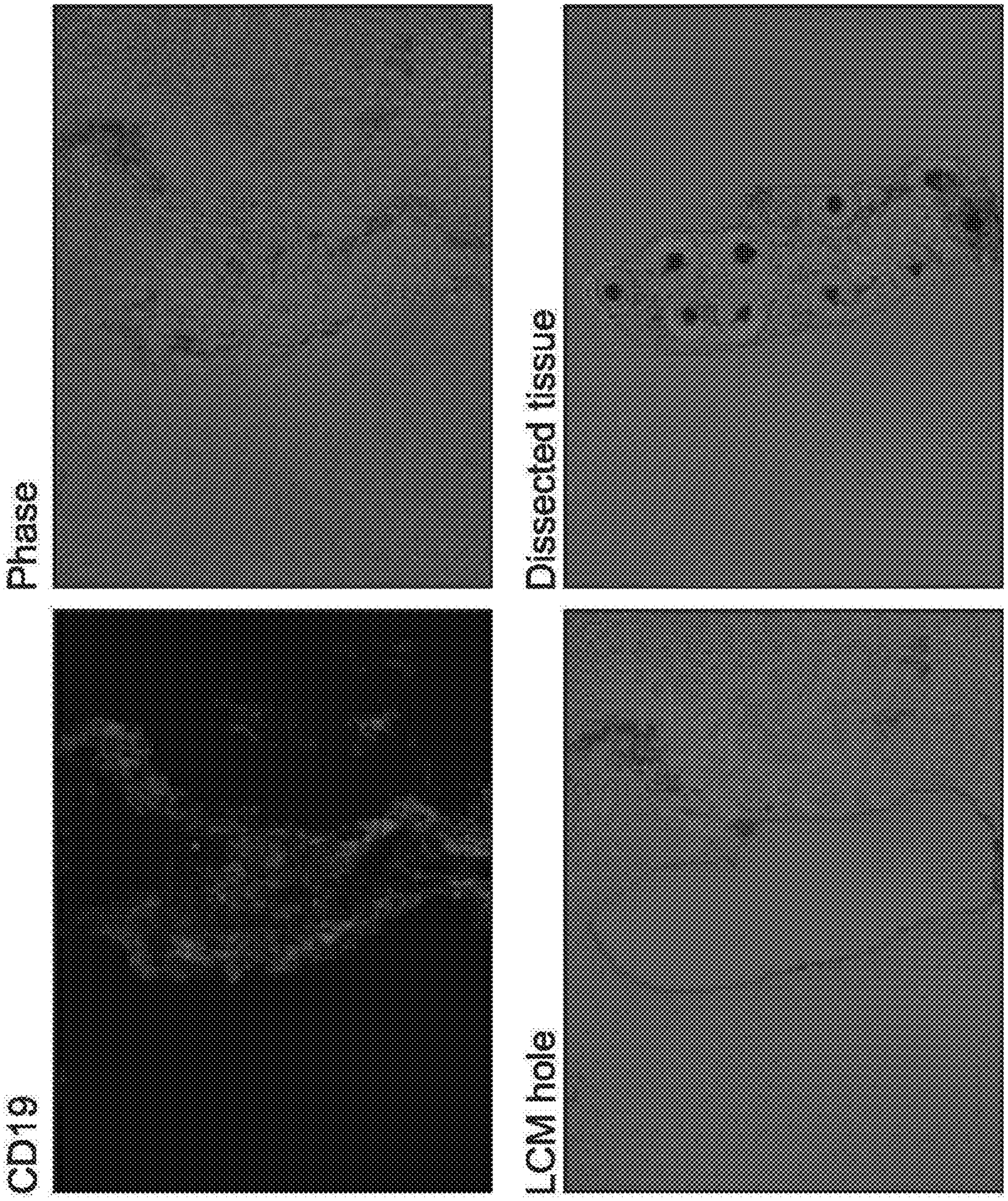

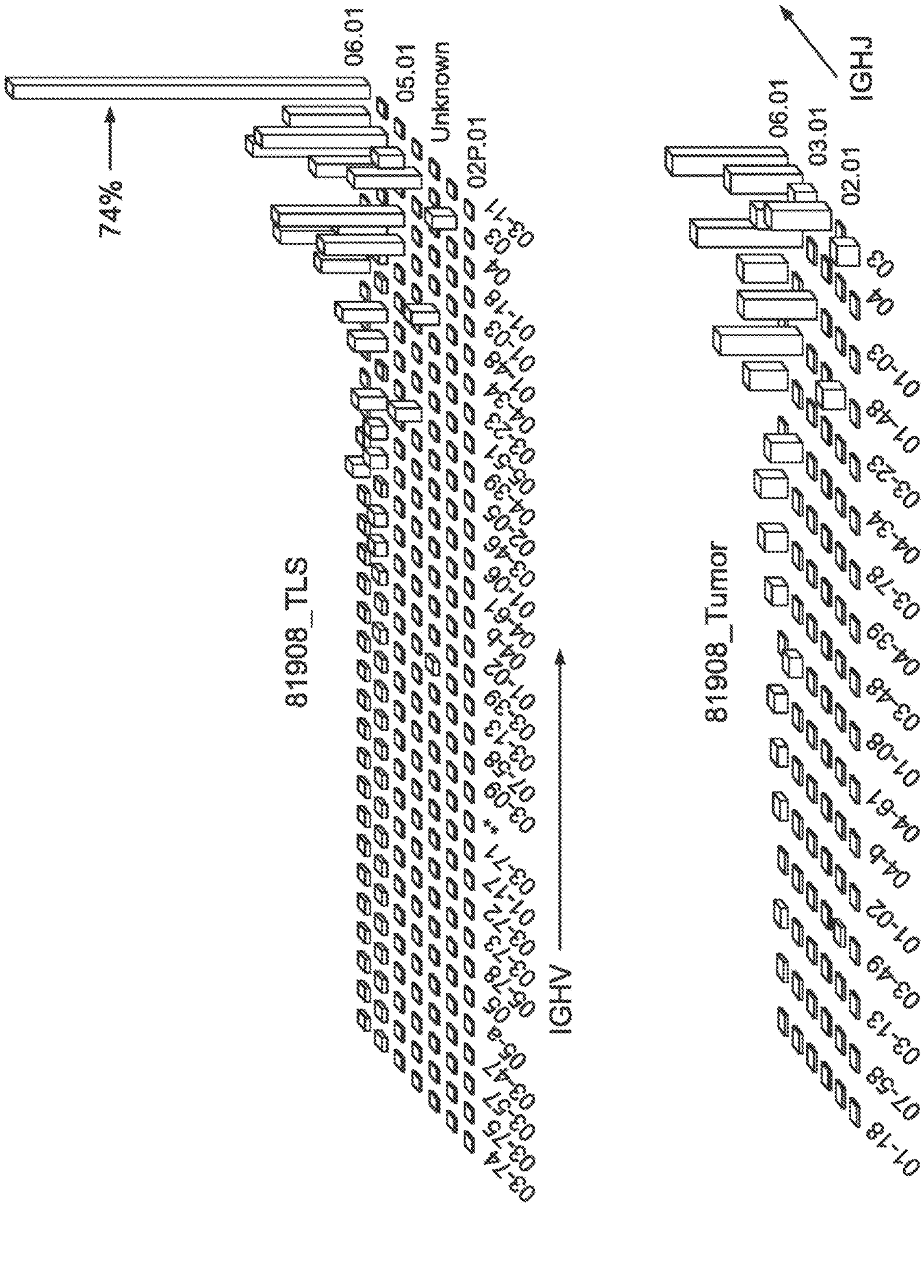
FIG. 26 (Cont. 1)

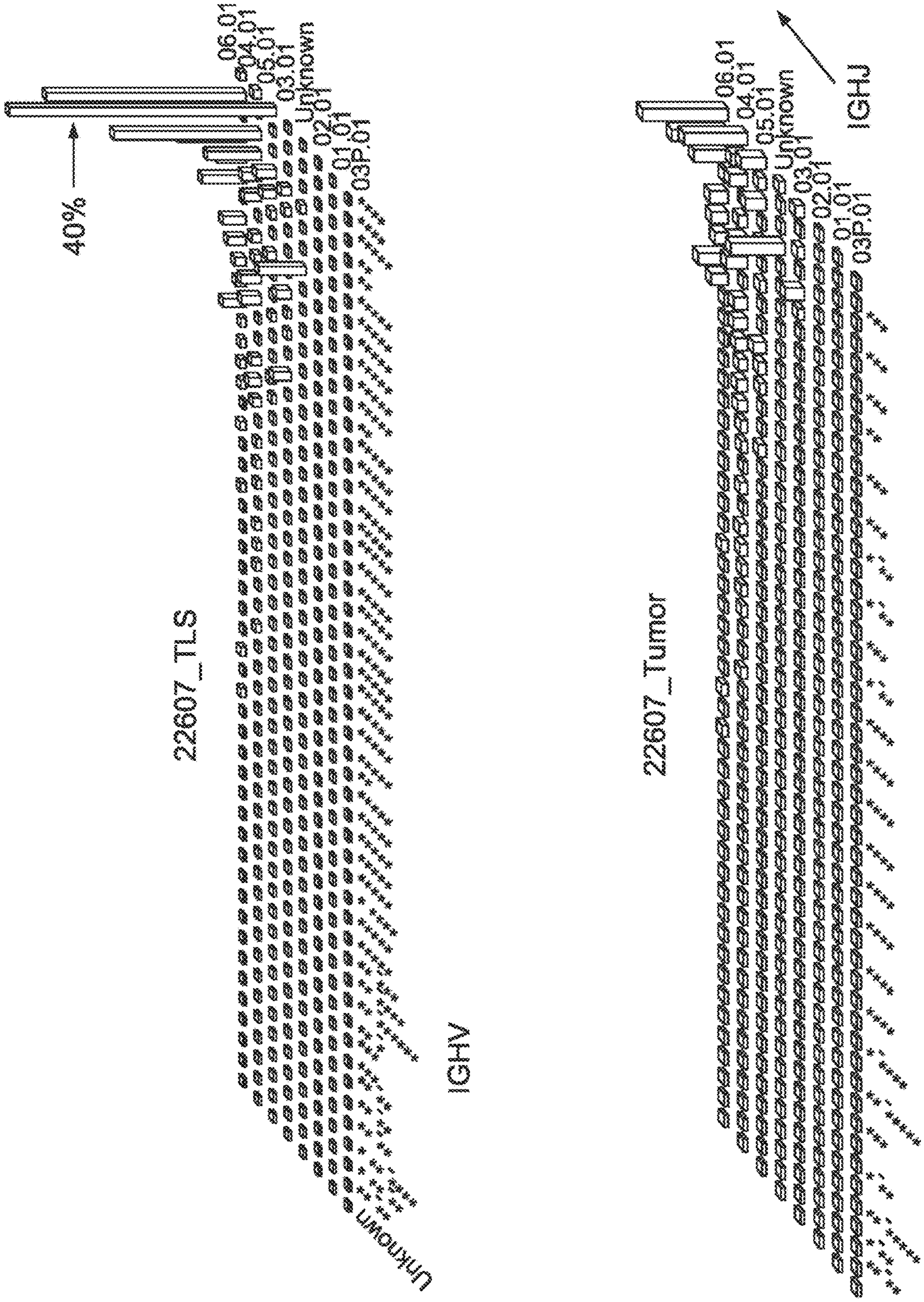
FIG. 26 (Cont. 2)

```
SEQUENCE LISTING

<160> NUMBER OF SEQ ID NOS: 14

<210> SEQ ID NO 1
```

<211> LENGTH: 125
<212> TYPE: PRT
<213> ORGANISM: Artificial Sequence
<220> FEATURE:
<223> OTHER INFORMATION: Synthetic construct

<400> SEQUENCE: 1

```
Gln Leu Val Gln Ser Gly Ala Glu Val Lys Lys Pro Gly Ala Ser Val
1               5                   10                  15

Lys Val Ser Cys Lys Ala Ser Gly Tyr Thr Phe Thr Ser Tyr Asp Ile
            20                  25                  30

Asn Trp Val Arg Gln Ala Thr Gly Gln Gly Leu Glu Trp Met Gly Trp
        35                  40                  45

Met Asn Pro Asn Ser Gly Asn Thr Gly Tyr Ala Gln Lys Phe Gln Gly
    50                  55                  60

Arg Val Thr Met Thr Arg Asn Thr Ser Ile Ser Thr Ala Tyr Met Glu
65                  70                  75                  80

Leu Ser Ser Leu Arg Ser Glu Asp Thr Ala Val Tyr Tyr Cys Ala Arg
                85                  90                  95

Gly Gly Gly Ala Ser Ser Trp Tyr Ser Val Tyr Tyr Tyr Tyr Tyr Met
            100                 105                 110

Asp Val Trp Gly Lys Gly Thr Thr Val Thr Val Ser Ser
        115                 120                 125
```

<210> SEQ ID NO 2
<211> LENGTH: 109
<212> TYPE: PRT
<213> ORGANISM: Artificial Sequence
<220> FEATURE:
<223> OTHER INFORMATION: Synthetic construct

<400> SEQUENCE: 2

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Tyr Asn Asn Trp Pro Pro
                85                  90                  95

Leu Phe Thr Phe Gly Pro Gly Thr Lys Val Asp Ile Lys
            100                 105
```

<210> SEQ ID NO 3
<211> LENGTH: 10
<212> TYPE: PRT
<213> ORGANISM: Artificial Sequence
<220> FEATURE:
<223> OTHER INFORMATION: Synthetic construct

<400> SEQUENCE: 3

```
Gly Tyr Thr Phe Thr Ser Tyr Asp Ile Asn
1               5                   10
```

<210> SEQ ID NO 4
<211> LENGTH: 13

<212> TYPE: PRT
<213> ORGANISM: Artificial Sequence
<220> FEATURE:
<223> OTHER INFORMATION: Synthetic construct

<400> SEQUENCE: 4

Trp Met Asn Pro Asn Ser Gly Asn Thr Gly Tyr Ala Gln
1 5 10

<210> SEQ ID NO 5
<211> LENGTH: 19
<212> TYPE: PRT
<213> ORGANISM: Artificial Sequence
<220> FEATURE:
<223> OTHER INFORMATION: Synthetic construct

<400> SEQUENCE: 5

Arg Gly Gly Gly Ala Ser Ser Trp Tyr Ser Val Tyr Tyr Tyr Tyr Tyr
1 5 10 15

Met Asp Val

<210> SEQ ID NO 6
<211> LENGTH: 11
<212> TYPE: PRT
<213> ORGANISM: Artificial Sequence
<220> FEATURE:
<223> OTHER INFORMATION: Synthetic construct

<400> SEQUENCE: 6

Arg Ala Ser Gln Gly Val Ser Ser Tyr Leu Ala
1 5 10

<210> SEQ ID NO 7
<211> LENGTH: 7
<212> TYPE: PRT
<213> ORGANISM: Artificial Sequence
<220> FEATURE:
<223> OTHER INFORMATION: Synthetic construct

<400> SEQUENCE: 7

Asp Ala Ser Asn Arg Ala Thr
1 5

<210> SEQ ID NO 8
<211> LENGTH: 11
<212> TYPE: PRT
<213> ORGANISM: Artificial Sequence
<220> FEATURE:
<223> OTHER INFORMATION: Synthetic construct

<400> SEQUENCE: 8

Gln Gln Tyr Asn Asn Trp Pro Pro Leu Phe Thr
1 5 10

<210> SEQ ID NO 9
<211> LENGTH: 381
<212> TYPE: DNA
<213> ORGANISM: Artificial Sequence
<220> FEATURE:
<223> OTHER INFORMATION: Synthetic construct

<400> SEQUENCE: 9
aggtgcagct ggtgcagtct ggggctgagg tgaagaagcc tggggcctca gtgaaggtct 60
cctgcaaggc ttctggatac accttcacca gttatgatat caactgggtg cgacaggcca 120
ctggacaagg gcttgagtgg atgggatgga tgaaccctaa cagtggtaac acaggctatg 180
cacagaagtt ccagggcaga gtcaccatga ccaggaacac ctccataagc acagcctaca 240
tggagctgag cagcctgaga tctgaggaca cggccgtgta ttactgtgcg agaggggggg 300
gggccagcag ctggtactcg gtgtactact actactacat ggacgtctgg ggcaaaggga 360
ccacggtcac cgtctcctca g 381

<210> SEQ ID NO 10
<211> LENGTH: 329
<212> TYPE: DNA
<213> ORGANISM: Artificial Sequence
<220> FEATURE:
<223> OTHER INFORMATION: Synthetic construct

<400> SEQUENCE: 10
gagaaatagt gatgacgcag tctccagcca ccctgtctgt gtctccaggg gaaagagcca 60
ccctctcctg cagggccagt cagagtgtta gcagcaactt agcctggtac cagcagaaac 120
ctggccaggc tcccaggctc ctcatctatg gtgcatccac cagggccact ggtatcccag 180
ccaggttcag tggcagtggg tctgggacag agttcactct caccatcagc agcctgcagt 240
ctgaagattt tgcagtttat tactgtcagc agtataataa ctggcctcct ctattcactt 300
tcggccctgg gaccaaagtg gatatcaaa 329

<210> SEQ ID NO 11
<211> LENGTH: 1255
<212> TYPE: PRT
<213> ORGANISM: Artificial Sequence
<220> FEATURE:
<223> OTHER INFORMATION: Amino acid sequence for SI (RBM);S2

<400> SEQUENCE: 11

Met Phe Ile Phe Leu Leu Glu Leu Thr Leu Thr Ser Gly Ser Asp Leu
1 5 10 15

Asp Arg Cys Thr Thr Glu Asp Asp Val Gln Ala Pro Asn Tyr Thr Gln
20 25 30

His Thr Ser Ser Met Arg Gly Val Tyr Tyr Pro Asp Glu Ile Glu Arg
35 40 45

Ser Asp Thr Leu Tyr Leu Thr Gln Asp Leu Phe Leu Pro Phe Tyr Ser
50 55 60

Asn Val Thr Gly Phe His Thr Ile Asn His Thr Phe Gly Asn Pro Val
65 70 75 80

Ile Pro Phe Lys Asp Gly Ile Tyr Phe Ala Ala Thr Glu Lys Ser Asn
85 90 95

Val Val Arg Gly Trp Val Glu Gly Ser Thr Met Asn Asn Lys Ser Gln
100 105 110

Ser Val Ile Ile Ile Asn Asn Ser Thr Asn Val Val Ile Arg Ala Cys
115 120 125

Asn Phe Glu Leu Cys Asp Asn Pro Phe Phe Ala Val Ser Lys Pro Met
130 135 140

Gly Thr Gln Thr His Thr Met Ile Phe Asp Asn Ala Phe Asn Cys Thr
145 150 155 160

Phe Glu Tyr Ile Ser Asp Ala Phe Ser Leu Asp Val Ser Glu Lys Ser
165 170 175

Gly Asn Phe Lys His Leu Arg Glu Phe Val Phe Lys Asn Lys Asp Gly
180 185 190

Phe Leu Tyr Val Tyr Lys Gly Tyr Gln Pro Ile Asp Val Val Arg Asp
195 200 205

```
Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Glu Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Glu Glu Ile Asp Lys Gly Ile Tyr Gln Thr Ser Asn
    290                 295                 300

Glu Arg Val Val Pro Ser Gly Asp Val Val Arg Glu Pro Asn Ile Thr
305                 310                 315                 320

Asn Leu Cys Pro Phe Gly Glu Val Glu Asn Ala Thr Lys Glu Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Glu Ser Thr Glu Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Glu Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Glu Gln Pro Phe Gln Gln Phe Gly Arg Asp Val Ser Asp Glu Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620
```

```
Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Glu Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Glu Gly Ala Gly Ala Ala Leu Gln Ile Pro Phe
865                 870                 875                 880

Ala Met Gln Met Ala Tyr Arg Glu Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Glu Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                1015                1020

Phe Cys  Gly Lys Gly Tyr His  Leu Met Ser Phe Pro  Gln Ala Ala
    1025                1030                1035

Pro His  Gly Val Val Phe Leu  His Val Thr Tyr Val  Pro Ser Gln
```

```
    1040                1045                1050

Glu Arg  Asn Phe Thr Thr Ala  Pro Ala Ile Cys His  Glu Gly Lys
    1055                1060                1065

Ala Tyr  Phe Pro Arg Glu Gly  Val Phe Val Phe Asn  Gly Thr Ser
    1070                1075                1080

Trp Phe  Ile Thr Gln Arg Asn  Phe Phe Ser Pro Gln  Ile Ile Thr
    1085                1090                1095

Thr Asp  Asn Thr Phe Val Ser  Gly Asn Cys Asp Val  Val Ile Gly
    1100                1105                1110

Ile Ile  Asn Asn Thr Val Tyr  Asp Pro Leu Gln Pro  Glu Leu Asp
    1115                1120                1125

Ser Phe  Lys Glu Glu Leu Asp  Lys Tyr Phe Lys Asn  His Thr Ser
    1130                1135                1140

Pro Asp  Val Asp Leu Gly Asp  Ile Ser Gly Ile Asn  Ala Ser Val
    1145                1150                1155

Val Asn  Ile Gln Lys Glu Ile  Asp Arg Leu Asn Glu  Val Ala Lys
    1160                1165                1170

Asn Leu  Asn Glu Ser Leu Ile  Asp Leu Gln Glu Leu  Gly Lys Tyr
    1175                1180                1185

Glu Gln  Tyr Ile Lys Trp Pro  Trp Tyr Val Trp Leu  Gly Phe Ile
    1190                1195                1200

Ala Gly  Leu Ile Ala Ile Val  Met Val Thr Ile Leu  Leu Cys Cys
    1205                1210                1215

Met Thr  Ser Cys Cys Ser Cys  Leu Lys Gly Ala Cys  Ser Cys Gly
    1220                1225                1230

Ser Cys  Cys Lys Phe Asp Glu  Asp Asp Ser Glu Pro  Val Leu Lys
    1235                1240                1245

Gly Val  Lys Leu His Tyr Thr
    1250                1255
```

<210> SEQ ID NO 12
<211> LENGTH: 16
<212> TYPE: PRT
<213> ORGANISM: Artificial Sequence
<220> FEATURE:
<223> OTHER INFORMATION: Epitope for S1

<400> SEQUENCE: 12

```
Met Gly Cys Val Leu Ala Trp Asn Thr Arg Asn Ile Asp Ala Thr Ser
1               5                   10                  15
```

<210> SEQ ID NO 13
<211> LENGTH: 16
<212> TYPE: PRT
<213> ORGANISM: Artificial Sequence
<220> FEATURE:
<223> OTHER INFORMATION: Epitope for S1

<400> SEQUENCE: 13

```
Leu Arg His Gly Lys Leu Arg Pro Phe Glu Arg Asp Ile Ser Asn Val
1               5                   10                  15
```

<210> SEQ ID NO 14
<211> LENGTH: 22
<212> TYPE: PRT
<213> ORGANISM: Artificial Sequence
<220> FEATURE:
<223> OTHER INFORMATION: Epitope for S1

<400> SEQUENCE: 14

-continued

```
Leu Ser Asn Val Pro Phe Ser Pro Asp Gly Lys Pro Cys Thr Pro Pro
1               5                   10                  15

Ala Leu Asn Cys Tyr Trp
            20
```

ANTIBODIES AGAINST PROGRAMMED CELL DEATH PROTEIN 1 (PD1) AND USES THEREOF

CROSS REFERENCE TO RELATED APPLICATIONS

This application is a United States National Phase Patent Application of International Patent Application Number PCT/US2020/025792, filed on Mar. 30, 2020, which claims the benefit of U.S. Provisional Application No. 62/826,622, filed on Mar. 29, 2019, applications which are incorporated herein by reference in its entirety.

STATEMENT OF GOVERNMENT SUPPORT

This invention was made with Government support under Grant No. CA232758 awarded by the National Institutes of Health. The Government has certain rights in the invention.

REFERENCE TO SEQUENCE LISTING

The sequence listing submitted on Apr. 22, 2025, as a text file entitled "10110-224US1_ST25.txt" created on Apr. 16, 2025, and having a file size of 16.3 kilobytes is hereby incorporated by reference pursuant to 37 C.F.R. § 1.52 (e) (5).

I. BACKGROUND

Today, tumor immunology is primarily focused on T cells. However, T cells do not work in isolation. Within tumor beds, for instance, T and B cells often interact to form highly organized structures similar to lymph nodes, termed tertiary lymphoid structures (TLS). TLS contain a discrete T-cell zone occupied by CD4 and CD8 T cells, and high endothelial venules, adjacent to B-cell follicles, including germinal centers with interdigitating networks of follicular dendritic cells (DCs). TLS are associated with better outcomes in many tumors, including 23% of ovarian carcinomas, and have identified distinctive populations of CD45+CD19+CD20−CD138−CD38+ plasmoblasts in >50% of freshly dissociated human ovarian carcinomas. The proportion of T follicular helper (TFH) cells (crucial for the formation of germinal centers and isotype switched antibody production) strongly correlates with the percentage of plasmoblasts in the same samples. To aid present immunotherapies, what are needed are immortalized isotyped-switched B cells from TLS+ human cancers.

II. SUMMARY OF THE INVENTION

Disclosed herein, in one aspect, are binding molecules directed to PD1 that suitable for use in the treatment of PD1 mediated diseases and disorders.

In one aspect, disclosed herein are isolated PD1 binding molecules (such as, for example an antibody or immunotoxin) comprising a heavy chain variable domain comprising a Complementary Determining Region (CDR) 3 (CDR3) as set forth in SEQ ID NO: 5.

Also disclosed herein are isolated PD1 binding molecules of any preceding aspect wherein the binding molecule further comprises one or both CDRs as set forth in SEQ ID NO: 3 and SEQ ID NO: 4 (for example a binding molecule comprising a heavy chain variable domain comprises the CDRs as set forth in SEQ ID NO: 5 and SEQ ID NO: 3, SEQ ID NO: 5 and SEQ ID NO: 4, or SEQ ID NO: 3, SEQ ID NO: 4, and SEQ ID NO: 5). In one aspect, the isolated binding molecule can comprise the variable heavy chain domain as set forth in SEQ ID NO: 1.

In one aspect disclosed herein are isolated PD1 binding molecules of any preceding aspect, wherein the binding molecule further comprises a light chain variable domain comprising at least one CDR as set forth in SEQ ID NO: 6, SEQ ID NO: 7, or SEQ ID NO: 8 (such as, for example, a carriable light chain domain comprising the CDRs as set forth in SEQ ID NO: 6 and SEQ ID NO: 7; SEQ ID NO: 6 and SEQ ID NO: 8; SEQ ID NO: 7 and SEQ ID NO: 8; or SEQ ID NO: 6, SEQ ID NO: 7, and SEQ ID NO: 8). In one aspect, the isolated binding molecule can comprise the variable light chain domain as set forth in SEQ ID NO: 2 (for example a PD1 binding molecule comprising a variable heavy chain domain as set forth in SEQ ID NO: 1 and a variable light chain domain as set forth in SEQ ID NO: 2).

In one aspect, disclosed herein are PD1 binding molecules of any preceding aspect, wherein the binding molecule is an antibody and the antibody has an isotype of IgA. Accordingly, also disclosed herein are antibodies and/or immunotoxins comprising a heavy chain variable region as set forth in SEQ ID NO: 1 and/or a light chain variable region as set forth in SEQ ID NO: 2.

Also disclosed herein are methods for treating, ameliorating, decreasing, preventing, inhibiting, or reducing a cancer or metastasis in a subject, preferably a PD1-positive cancer or tumor, comprising to said patient a therapeutically effective amount of an anti-PD1 antibody comprising a variable heavy chain domain comprising a CDR3 as set forth in SEQ ID NO: 5.

In one aspect disclosed herein are methods of making the PD1 binding molecule of any preceding aspect (including anti-PD1 antibodies) or Coronavirus S protein binding molecule (including binding molecules that bind S protein epitopes) comprising isolating a B cell from a tertiary lymphoid structure within a tumor bed, immortalizing the isolated B cell, and sorting for reactive B cells. In one aspect, the B cells can be sorted using magnetic beads or flow cytometry to isolate cells based on binding to one or more of CD19, CD45, CD20, CD138, and/or CD38, wherein B cells as plasmoblasts comprise CD45+CD19+CD20-CD138-CD38+ B cells. The isolated B cells can be activated by incubating the isolated B cells with CD40 and/or IL-21 for between 2 and 10 days, preferably between 3 and 5 days, for example, 1, 2, 3, 4, 5, 6, 7, 8, 9, or days. In one aspect, the activation is less than 5 days. Following activation, the activated B cells can be immortalized with an Epstein Barr Virus (EBV). In some aspect, the methods can optionally further comprise a second round of activation following infection. In one aspect, the methods can further comprise sorting for reactive B cells using tetramers with biotinylated peptides and streptavidin-APC to sort immortalized B cells from the pool of ovarian cancer-derived B cells. Immortalized B cells can then be cultured in the presence of IL-21 and plate-bound antigen to induce affinity maturation with plate-bound antigen.

In one aspect, disclosed herein are methods of treating, inhibiting, ameliorating, decreasing, and/or preventing a coronaviral infection (such as, for example COVID-19) comprising administering one or more binding molecules (such as, for example, anti SARS-CoV-2 S protein antibodies) made by the methods of any preceding aspect. In one aspect, the binding molecules administered can be one or a cocktail of antibodies that bind B cell epitopes of the S protein of a coronavirus (such as for example, SARS-COV-2).

III. BRIEF DESCRIPTION OF THE DRAWINGS

The accompanying drawings, which are incorporated in and constitute a part of this specification, illustrate several embodiments and together with the description illustrate the disclosed compositions and methods.

FIGS. 1A and 1B show the positive correlation between T follicular helper (TFH) cells and plasmoblasts in human ovarian cancer and this accumulation is associated with improved outcomes. Five human advanced, serous, solid ovarian carcinoma specimens were freshly dissociated and the presence of live CD45+CD3+CD4+CXCR5+ICOS+PD1highBCL6+ TFH cells and CD45+C19+CD20−CD3−CD138−CD38+ plasmoblasts was quantified by flow cytometry, gating on viable (Zombie Yellowneg) cells. FIG. 1A shows examples of samples with (left, bottom) and without (right, bottom) plasmoblasts are shown. FIG. 1B shows the correspondence between the proportions of TFH and plasmoblasts in different specimens. R=0.997 (Pearson's correlation).

Figure 2B:
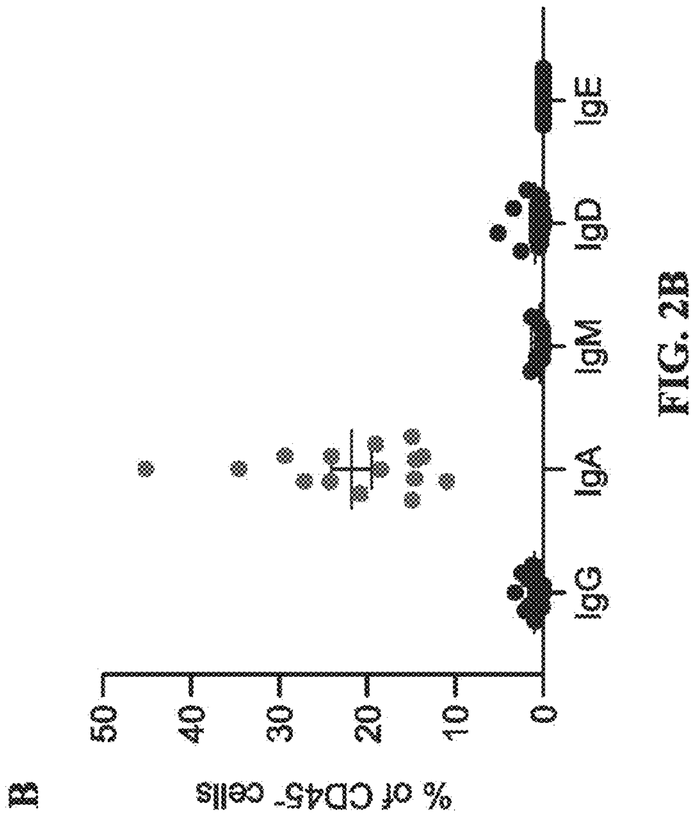
Figure 2A:
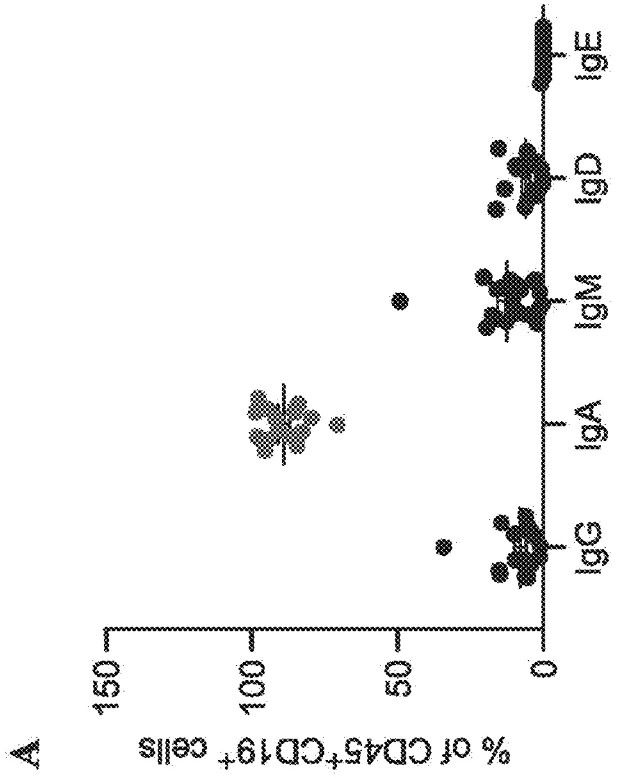

FIGS. 2A and 2B show that IgA producing B cells dominate the humoral response in human ovarian cancer. Fifteen human advanced, serous, solid ovarian carcinoma specimens were freshly dissociated and the presence of different classes of antibodies was detected of $CD45^{+}CD19^{+}$ B cells (2A) and $CD45^{-}$ cells (2B). This figures shows that the cells in the tumor microenvironment (TME) that are not leukocytes can also bind IgA.

Figure 3A:
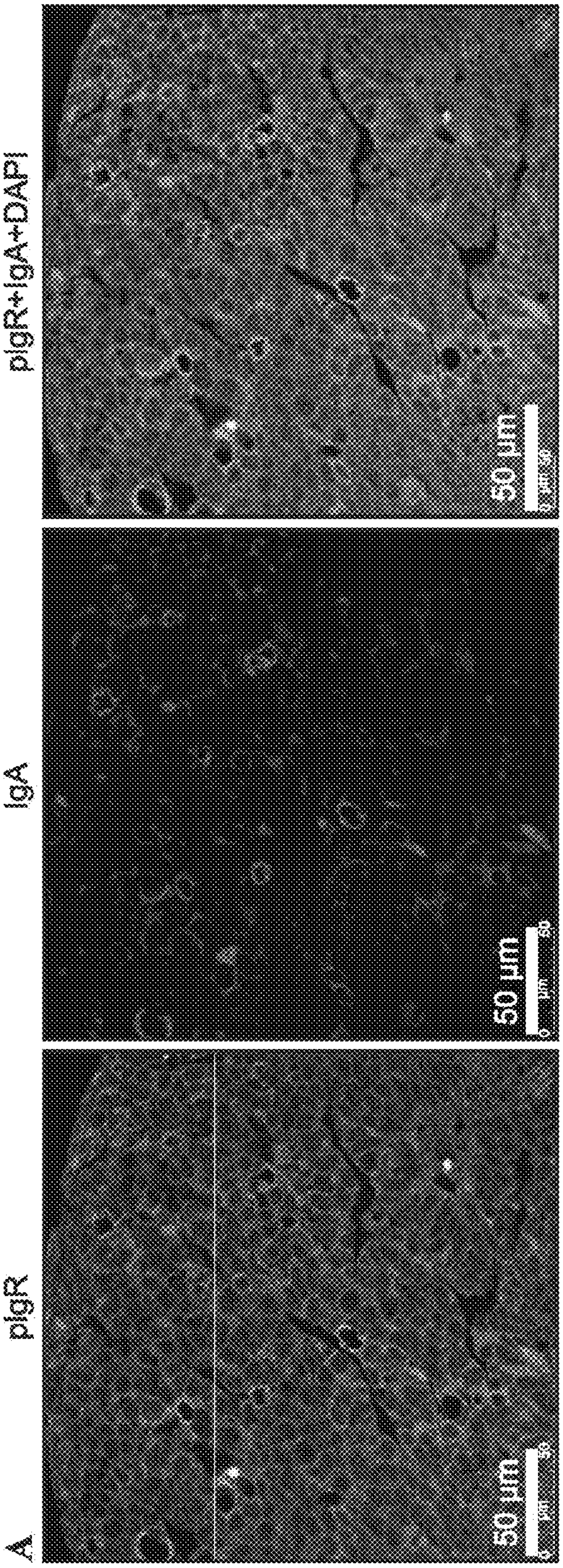
Figure 3B:
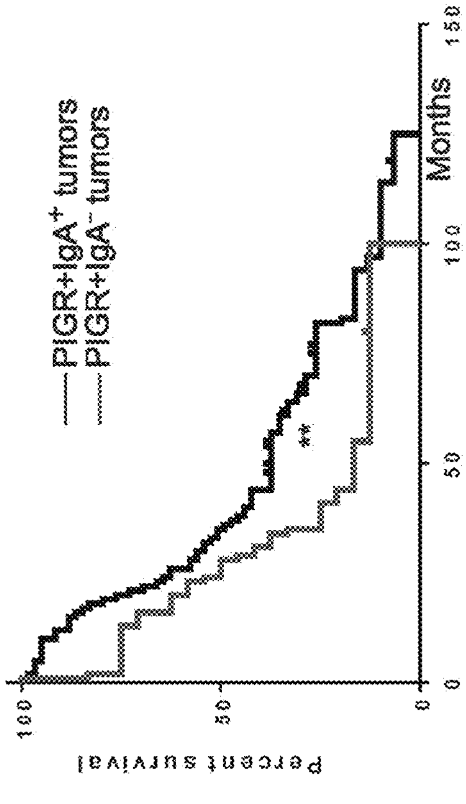

FIGS. 3A and 3B show that most human ovarian carcinomas express polymeric IgA Receptor (PIGR) and are coated by IgA. FIG. 3A shows 97 human stage III/IV serous ovarian carcinomas were stained with fluorescently labelled anti-PIGR and anti-IgA antibodies, plus DAPI. Combined PIGR+IgA signals were quantified using a Vectra spectral imaging system (PE) and an arbitrary threshold for positive (n=51) vs. negative (n=46) tumors was established by 2 independent observers. FIG. 3B shows Log-rank analysis of Kaplan-Meyer survival curves shows superior outcomes for patients with PGIR/IgA+ tumors.

Figure 4:
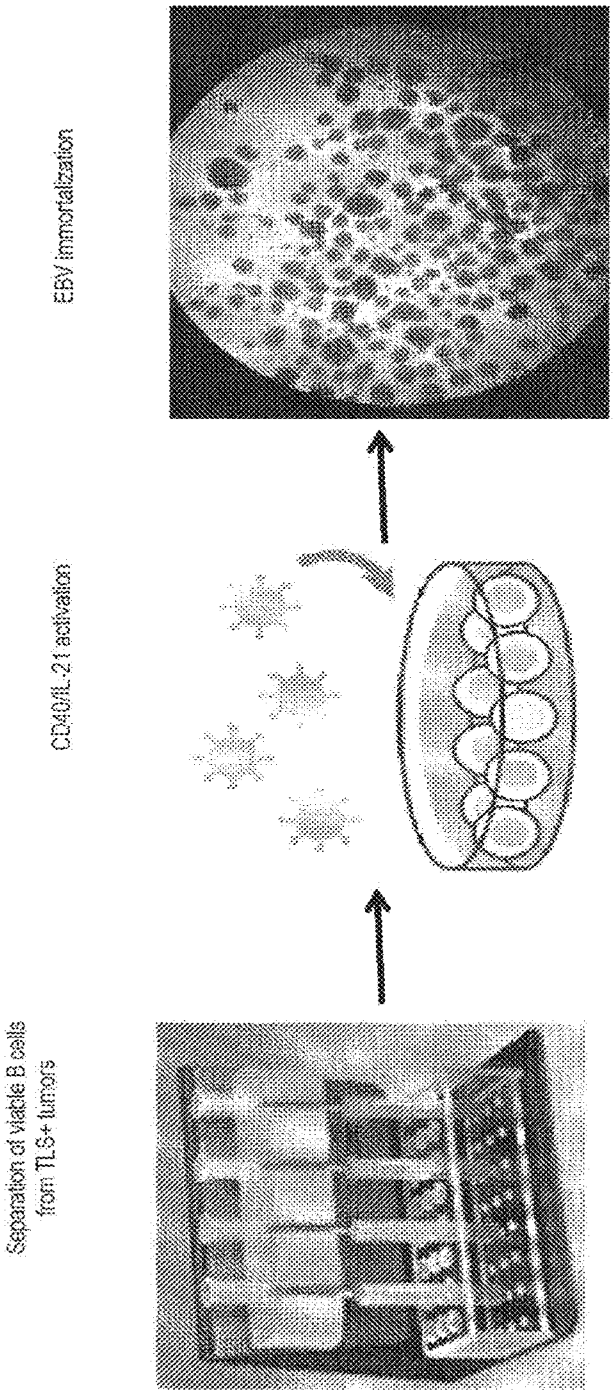

FIG. 4 shows optimization of a protocol for immortalizing B cells from freshly dissociated ovarian carcinomas. CD19+ B cells are magnetically immunopurified from freshly dissociated or cryopreserved human ovarian carcinomas and immediately activated for 3-5 days with a combination of CD40 agonistic antibodies and IL-21. Activated B cells are then infected with EBV, with activating conditions persisting for 5-7 additional days. An example of immortalized B cells is shown on the right.

Figure 5:
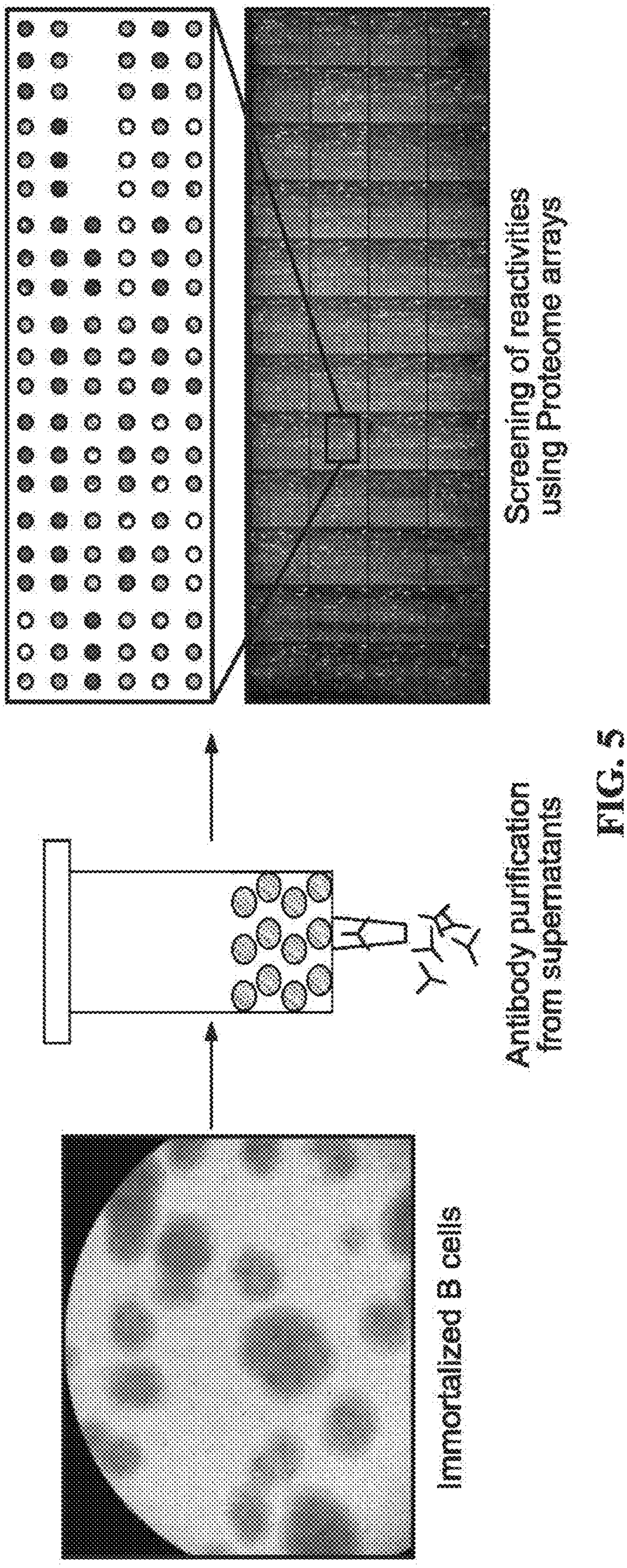

FIG. 5 shows characterization of IgA and IgG produced at tumor beds. IgA and IgG will be independently immunopurified from ≥8 ovarian carcinomas with conglomerates of B and T cells compatible with TLS and an equal number of samples where TLS are not identified in at least 2 sections.

FIG. 6. (A) Overall survival associated with the presence of CD19+ B-cells and CD3+ T-cells within ovarian carcinomas as assessed by multiplex immunofluorescence of TMAs corresponding to 575 HGSOC patients from the New England Case-Control Study cohort (NECC; 181 patients), the Nurses' Health Study (NHS; 301 patients) and Moffitt Cancer Center (MCC; 93 patients). B-cell infiltration is defined as the presence of CD19+ positive cells on any of the duplicate sections analyzed for each tumor, respectively. *, p≤0.05; , p≤0.01; *, p≤0.001; (log-rank (Mantel-Cox) test). (B) Overall survival associated with the presence of intraepithelial (i.e.,) CD19+ B-cells and ieCD8+ T-cells within ovarian carcinomas as assessed by multiplex immunofluorescence of TMAs corresponding to 575 HGSOC patients from the NHS, NECC, MCC cohorts. B-cells and CD8+ T-cells infiltration are defined as the presence of CD19+ or CD8+ positive cells on any of the duplicate sections analyzed for each tumor, respectively. *, p≤0.05; , p≤0.01; NS, not significant (log-rank (Mantel-Cox) test). (C) Higher number of IgG-coated cells in the PCK+ tumor islets (average from duplicated cores) is not associated with improved outcome in HGSOC, analyzed using median IgA-coating threshold in MCC and NECC cohorts. NS, Not significant; (log-rank (Mantel-Cox) test). (D) Colocalization of IgA with pIgR+ (IgA-pIgR co-localization≥median) cells in the PCK+ tumor islets is associated with improved outcome in HGSOC, compared to only pIgRHigh samples (≥median) without IgA co-localization (co-localization<median), in MCC and NECC cohorts. , p≤0.01; (log-rank (Mantel-Cox) test).

Figure 7:
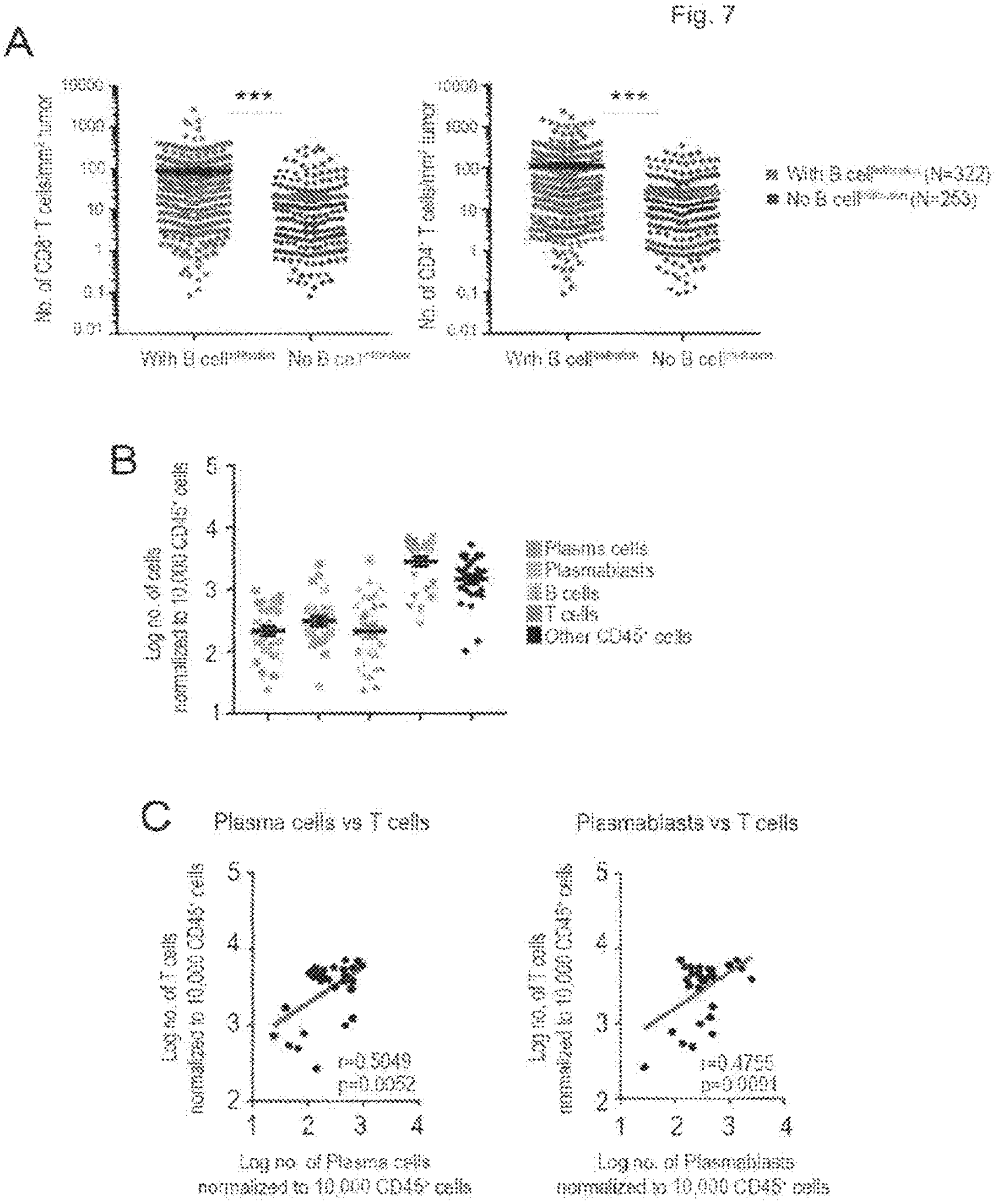

FIG. 7. (A) Accumulation of CD8+ (left) and CD4+ (right) T-cells in the PCK+ tumor islets are associated with the presence of B cells. (B) FACS analysis showing number (log) of plasma cells (CD45+CD3−CD19+/−CD20−CD138+), plasmablasts (CD45+CD3−CD19+CD20−CD38high), B cells (CD45+CD3−CD19+CD20+), T cells (CD45−CD3−) and other leukocytes (CD45+CD3−CD19−CD20−CD138−) in HGSOC (n=29). The data is normalized to 10,000 viable CD45+ leukocytes. (C) Graphs showing correlations between log no. of T cells and plasma cells (left; correlation co-efficient (r)=0.5049; p=0.0052); and between T cells and plasmablasts (right; correlation co-efficient (r)=0.4755; p=0.0091); All three cell types represent absolute counts normalized to 10,000 CD45+ leukocytes.

Figure 8A:
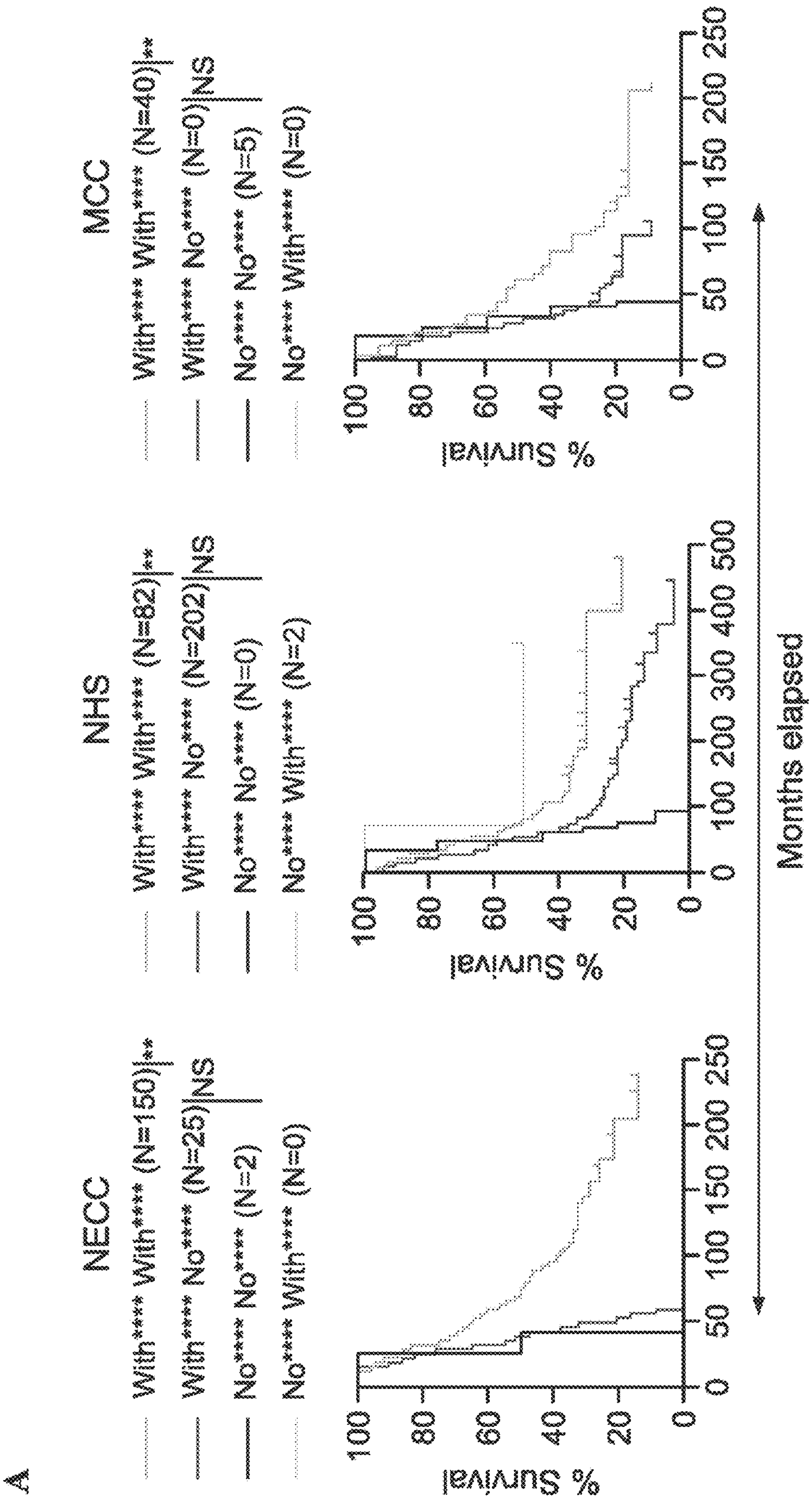
Figure 8:
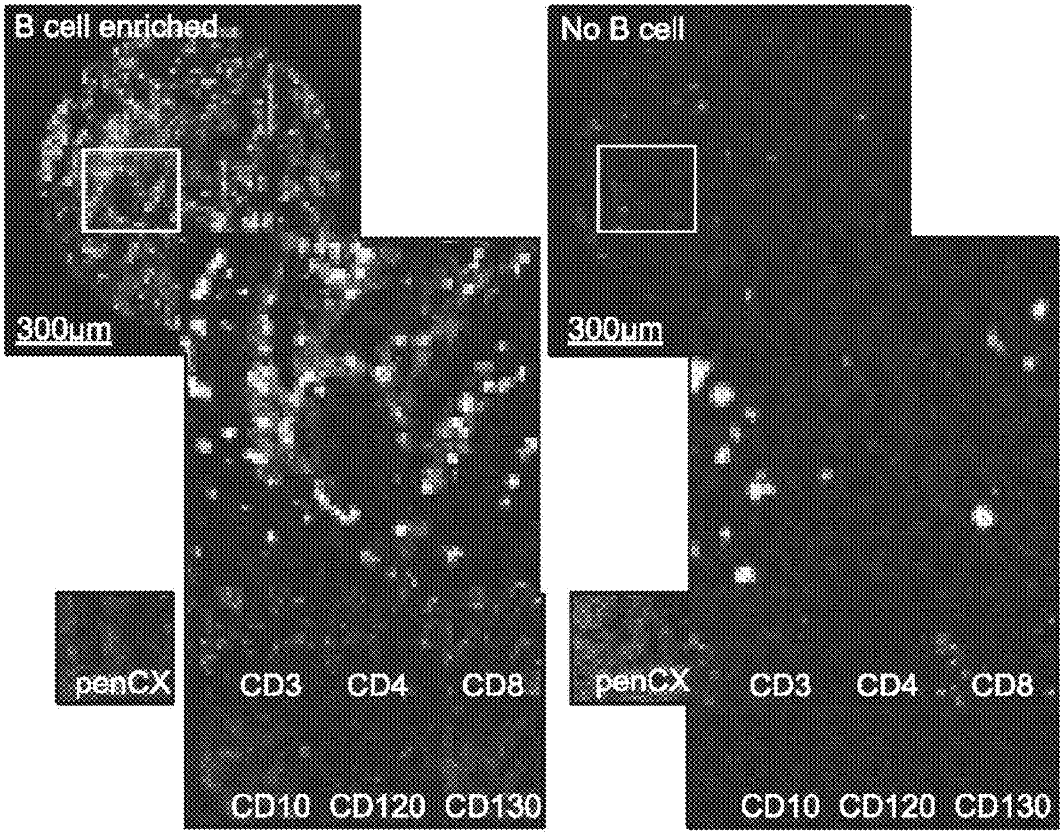
Figure 8:
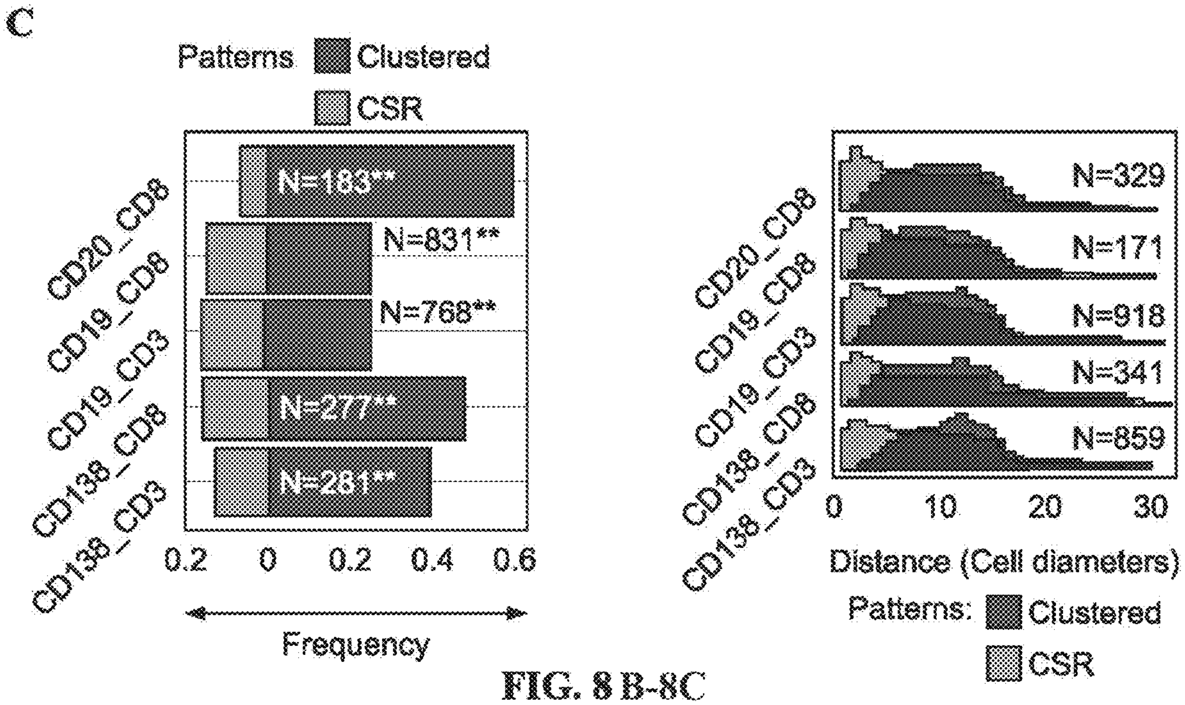

FIG. 8. B cell responses and IgA-pIgR co-localization are associated with protective immunity in human ovarian cancer. (A) Overall survival associated with the presence of intraepithelial (ie) CD19+ B-cells and CD3+ T-cells within ovarian carcinomas, as assessed by multiplex immunofluorescence of TMAs corresponding to 575 HGSOC patients from 3 cohorts: New England Case-Control Study (NECC; 181 patients), Nurses' Health Study (NHS; 301 patients); and Moffitt Cancer Center (MCC; 93 patients). B-cell and T-cell infiltration are defined as the presence of CD19+ or CD3+ positive cells on any of the duplicate sections analyzed for each tumor. , p≤0.01; NS, not significant (log-rank (Mantel-Cox) test). (B) Representative staining of the association between the accumulations of T- and B-cells at tumor beds. Bar, 200 μm. (C) Left, Frequency of histological sections that exhibit complete spatial randomness (CSR), versus those that show spatial clustering between each pair of cell phenotypes. N indicates the number of cores (each tumor is represented in 2 different cores in the array). *, p≤0.001 (chi-square test). Right, Histogram of distances at which significant spatial clustering between phenotypes is observed. CSR (Cyan) is the primary spatial pattern at short distances, but clustering (Purple) between cell types emerges as the dominant pattern as distance increases. (D) Left, Representative FACS analysis of immunoglobulin isotypes on the surface of B-cells infiltrating 29 different freshly dissociated human HGSOCs. Right, Percentage of cell counts of IgA/IgG/IgM+ cells per 10,000 viable Ig+CD45+ cells (FACS analysis). B cells, CD45+CD3−CD19+CD20+ cells; Plasmablasts, CD45+CD3−CD19+CD20+CD38High cells; Plasma cells, CD45+CD3−CD19+/−CD20−CD138+ cells. Each dot represents one tumor. To compare IgA+ versus the IgG+/IgM+ cell percentage in B cells, plasmablasts and plasma cells, two-way anova followed by Dunnett's ad hoc tests for multiple comparison was performed on arcsintransformed percentage data (IgA vs. IgG, p-value=1e-10; IgA vs. IgM, p-value=1e-

10). (E) Bar graphs representing the percentage of each isotype produced by plasma cells (top) or B cells (bottom) in the same tumors, normalized to 10,000 viable CD45+ cells. (F) Improved survival is associated with the presence of CD19+CD138+ plasma cells (multiplex immunofluorescence; any of the duplicated sections for each tumor) within HGSOCs for the 3 independent cohorts. *, $p\leq0.05$; **, $p\leq0.01$; (log-rank (Mantel-Cox) test). (G) IgA-coated CD45−EpCAM+ tumor epithelial cells in 10 additional dissociated HGSOC specimens. (H) Expression of pIgR protein in 27 independent HGSOCs; tumor-free Fallopian tube (FT), ovary and omental samples; ovarian tumor cell lines; and K562 leukemia cells and THP1 monocyte cells (negative controls). Positive control, recombinant human pIgR. (I) Left, Representative combined staining of IgA, pIgR, IgG, PCK and DAPI for 274 patients (MCC and NECC cohorts). Bar, 100-μm. Right, top Representative dot plot showing IgA-pIgR co-localized signal among DAPI+ PCK+ cells. Right, bottom, Scattered graph showing number of IgA-pIgR co-localized cells (averaged from duplicated cores) per mm2 of cytokeratin+ surface. (J) IgA-pIgR co-localization in PCK+ tumor islets (average from duplicated cores) is associated with improved outcome in HGSOC (threshold, median; MCC and NECC cohorts). *, $p\leq0.05$; ***, $p\leq0.001$; (log-rank (Mantel-Cox) test).

FIG. 9. (Top, left) Survival outcome associated with the expression of CD19 in 428 annotated HGSOCs in TCGA datasets, and association with the expression levels of CXCL13. (Top, right) Expression level of CXCL13 in the same TCGA datasets is associated with better survival and higher levels of TGFB. Expression values are shown in log 2 transformed normalized gene count. (Other panels, except bottom-right) Higher expression of T-cell-specific markers and T-cell effector molecules in these 428 annotated HGSOCs in TCGA datasets when expression levels of TGFB are higher. Expression values are shown in log 2 transformed normalized gene count. (Bottom, right) Relative abundances of IGHG chains based on TCGA transcriptional analyses. Abundances are shown in log 2 transformed RPKM (Reads Per Kilobase of transcripts) values, which corrects for both gene length and sequencing depth.

Figure 10:
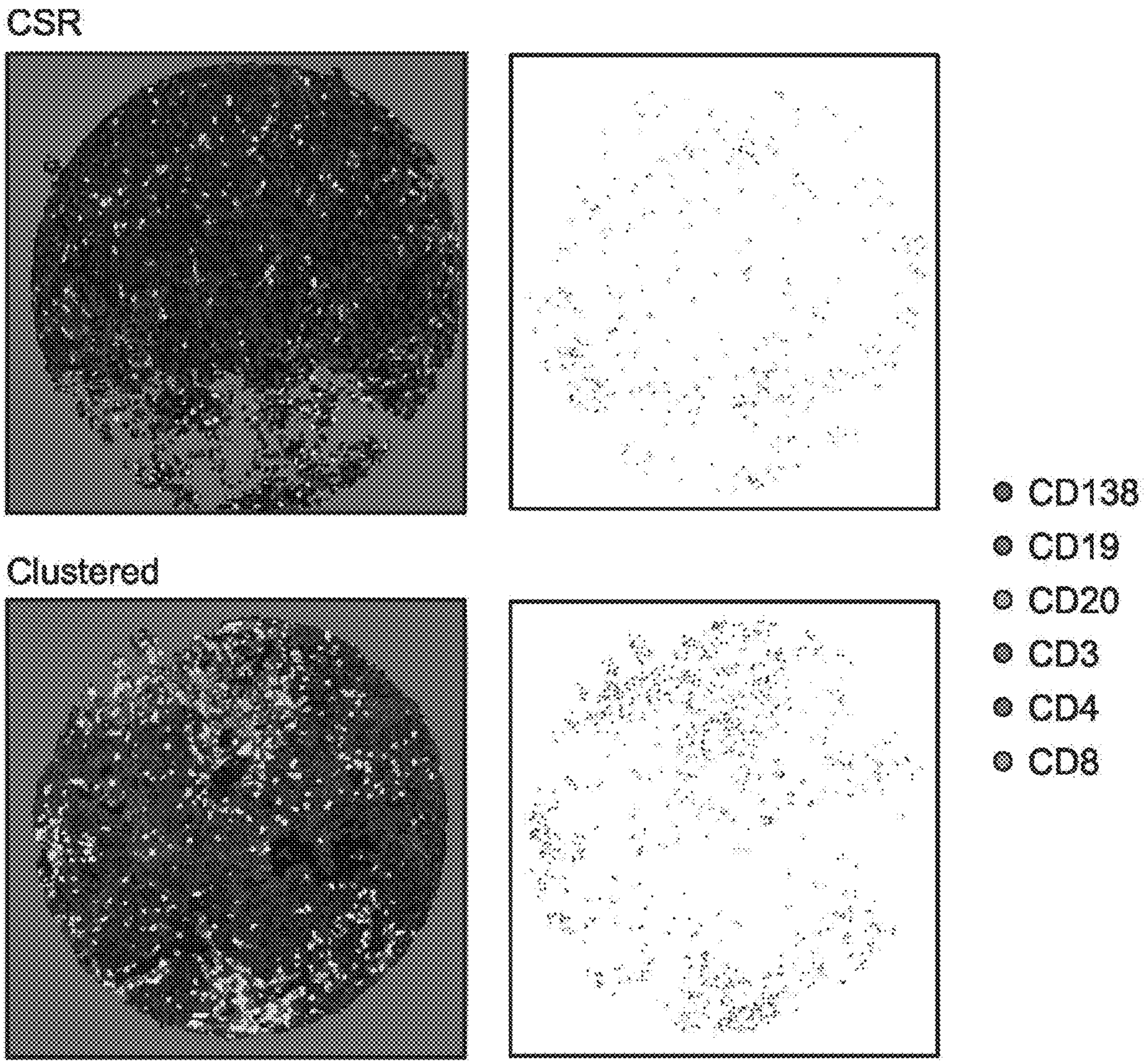

FIG. 10. Example of a core with complete spatial randomness (CSR) between CD8 T-cells and B-cells and a core with significant spatial clustering between CD8 T cells and B cells, showing both multilayered immunofluorescence (left) and phenotype segmented files (right).

Figure 11A:
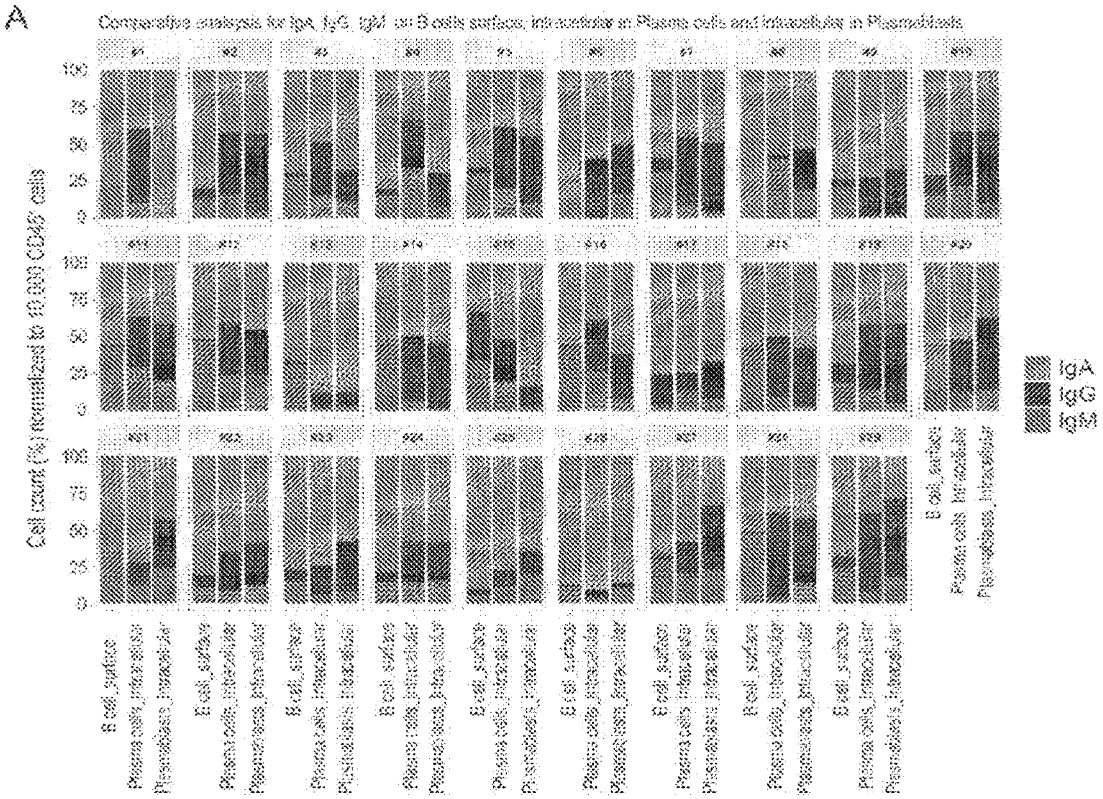
Figure 11B:
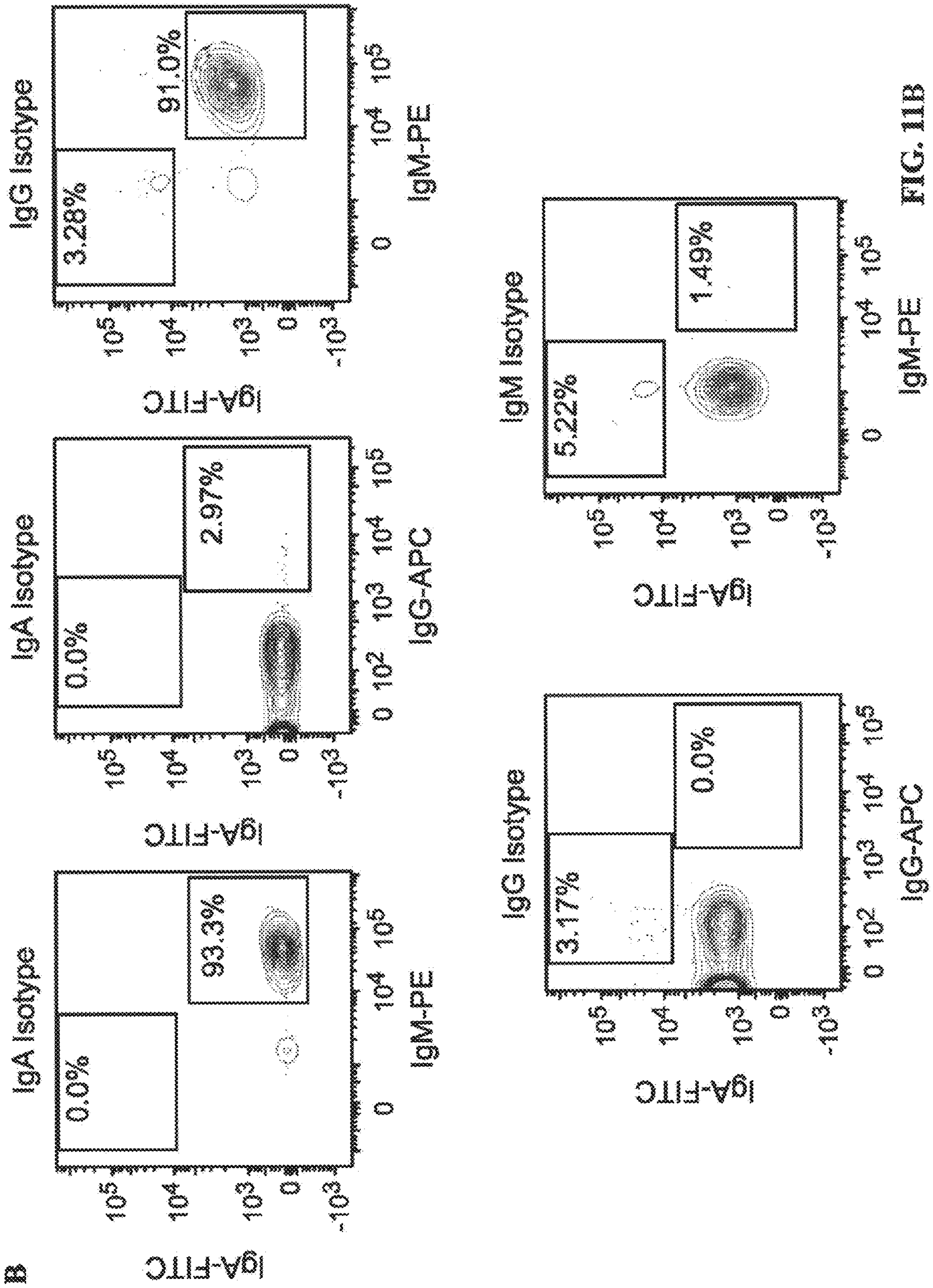

FIG. 11. (A) Bar graphs representing tumor-wise FACS analysis comparison of percentages of each Ig positive cells among total Ig positive B cells (CD45+CD3−CD19+ CD20+), plasma cells (intracellular in CD45+CD3− CD19+/−CD20+CD138+) and plasmablasts (intracellular in CD45+CD3−CD19+CD20−CD38High), normalized to 10,000 viable CD45+ cells. n=29 (B) FACS dot plots from isotype controls for IgA, IgG, IgM antibodies, used to create gates for respective Ig population.

Figure 12:
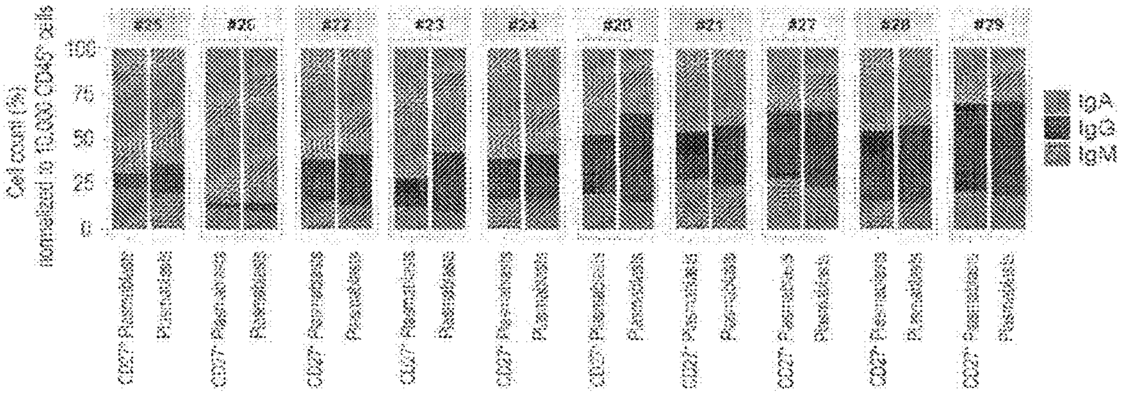
Figure 12:
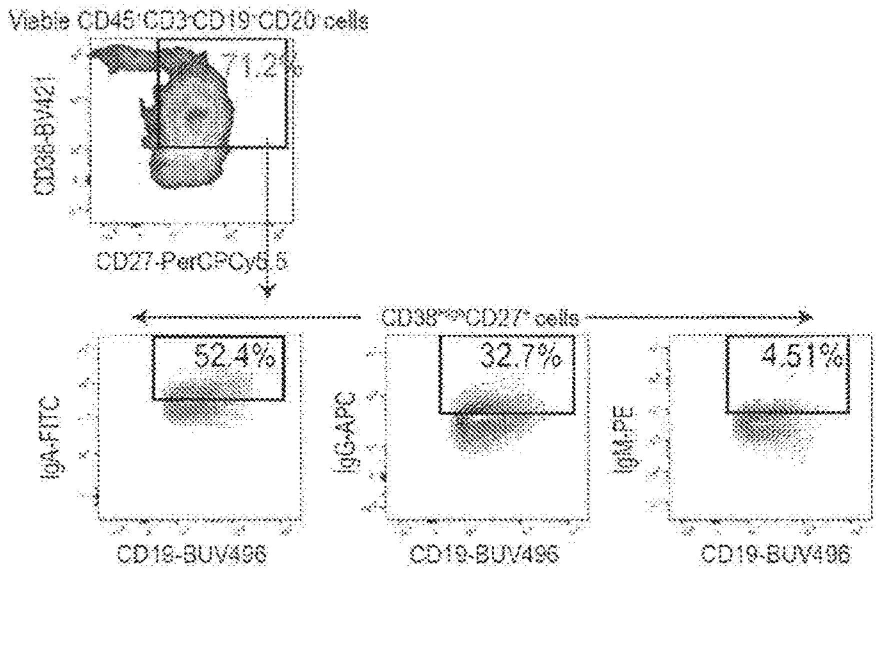

FIG. 12. Bar graphs representing tumor-wise FACS analysis comparison of percentages of each Ig positive cells among total Ig positive plasmablasts (intracellular in CD45+ CD3−CD19+CD20−CD38High) and CD27+ plasmablasts (intracellular in CD45+CD3−CD19+CD20− CD38HighCD27+), normalized to 10,000 viable CD45+ cells. n=10. Representative FACS dot plot showing CD27+ CD38High population among gated viable CD45+CD3− CD19+CD20− cells, and intracellular Ig isotypes in gated CD45+CD3−CD19+CD20−CD38HighCD27+ population of cells.

FIG. 13. Transcytosis of IgA through pIgR+ ovarian cancer cells impairs tumor growth and augments T-cell-mediated cytotoxic killing. (A) Density of IgA-coated cells in PCK+ tumor islets (average of duplicated cores) is associated with improved outcome in HGSOC (threshold, median; MCC and NECC cohorts). *, $p\leq0.05$; **, $p\leq0.01$; (log-rank (Mantel-Cox) test). (B) Representative combined IgA, IgG, and DAPI staining in tumors with high and low density of CD4+ and CD8+ T-cells. Bar, 200-μm. CD4+ (top) and CD8+ (bottom) T-cell accumulation (≥median) is associated with the density of IgA-coated tumor (PCK+) cells. *, $p\leq0.05$; , $p\leq0.01$; (unpaired two-tailed t-tests) (C) Top, Confocal microscopy of fluorescently (APC) labeled whole or pepsinized irrelevant IgA or IgG in pIgR+/pIgR-ablated OVCAR3 cells after 1 hr or 8 hr of incubation. Bottom, Scattered bar graph showing comparison of mean antibody internalization signal in different treatment conditions, where each dot represents quantitation from one cell. , $p\leq0.01$; ***, $p\leq0.001$; (unpaired two-tailed t-tests). (D) Immunoblots showing PIGR co-immunoprecipitates with IgA, but not β-actin (control) using lysates from 5 HGSOCs. (E) OVCAR3 cells were incubated with 0.5 μg/mL of control IgA or IgG for 8 hr in serum-free media in the presence of wortmannin (1 μM), brefeldin-A (1 μg/ml), or vehicle, and supernatants were subjected to Mass Spectrometry. (Left and center) The AA62-77 fragment of pIgR was only found after incubation with IgA (n=3 experiments). (Right) Heatmap of all peptides of the extracellular domain of pIgR (n=3 experiments). BFA, brefeldin-A. WM, wortmannin. (F) Left, Co-immunoprecipitates of supernatants from IgA-treated (0.5 μg/mL) pIgR+ or pIgR-ablated OVCAR3 cells, with or without brefeldin-A (1 μg/ml) or wortmannin (1 μM), blotted for secretory component of pIgR and IgA (Input control). Right, Bar graphs showing LC-MS/MS analysis of the co-immunoprecipitates showing intensities (Log 2) of secretory component of pIgR and IgA (n=2 experiments). (G) Upregulated pathways (GSEA analysis of RNA sequencing) after incubation of OVCAR3 cells with irrelevant IgA (0.5 μg/mL) for 24 hours, compared to IgG (0.5 μg/mL) or vehicle (n=3 experiments). (H) Progressive increase in DUSP5 and concomitant reduction in phospho-ERK1/2 after IgA treatment (8 hr; left) of OVCAR3 cells, but not IgG treatment (right). (I) Dose-dependent cytotoxic killing of NY-transduced OVCAR3 cells by NY-ESO-1-TCR-transduced T-cells is augmented by coincubation with 0.5 μg/mL of IgA, compared to IgG or PBS (left). IgA treatment also augmented the activity of antitumor activity of FSH-targeted chimeric receptor T-cells (right). Representative of 2 independent experiments. *, $p<0.05$; , $p\leq0.01$; *, $p\leq0.001$; (unpaired two-tailed t-tests). (J) Cytotoxic killing of primary CD45-EpCAM+ tumor cells by autologous tumor-infiltrating T-cells (1:1 ratio) is augmented by co-incubation with autologous (tumor derived) or irrelevant IgA (0.5 μg/mL), but not autologous, tumor-derived IgG. Representative of 2 independent experiments. , $p\leq0.01$; *, $p\leq0.001$; NS, not significant (unpaired two-tailed t-tests). (K) RAG1-deficient mice inoculated subcutaneously with 107 OVCAR3 cells received 100 μg/20 g body weight of IgA or control IgG peritumorally at days 7, 11, 15, 19 and 23 after tumor inoculation. Tumor growth curves (left; pooled from 2 independent experiments); tumor weight at day 21 (center); and representative differences in tumor volume (right) are shown. Curves and tumor weights were pooled from 2 independent experiments (10 mice/group, total). *, $p\leq0.05$; (paired two-tailed t-tests).

Figure 14:
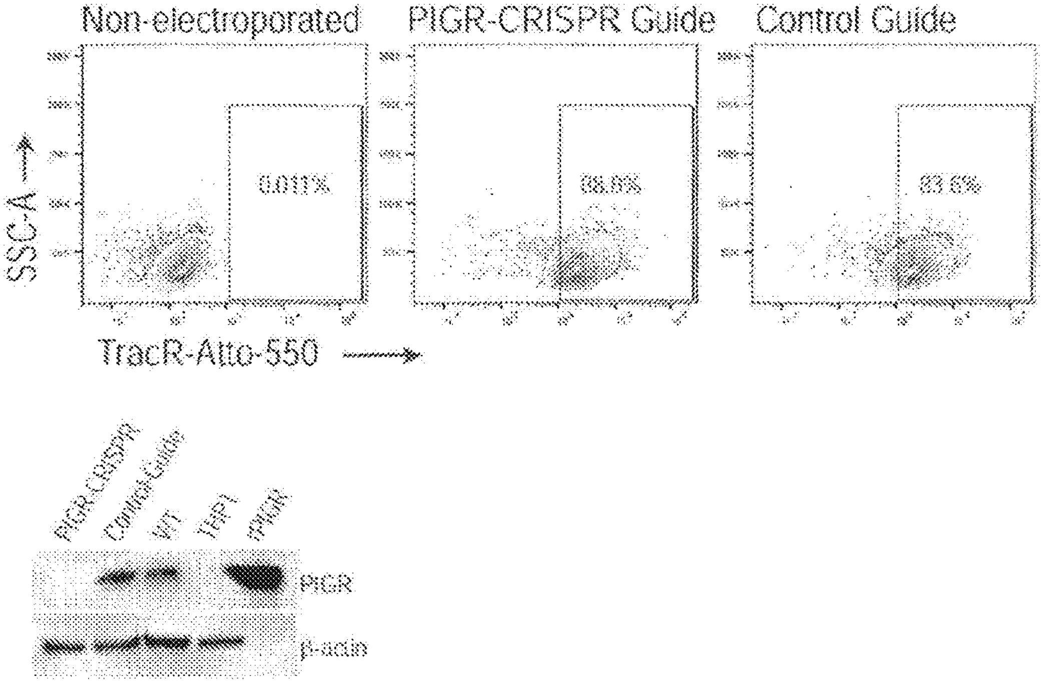

FIG. 14. FACS dot plots showing electroporation efficiency in pIgR-CRISPRGuide (middle) or Control-guide electroporated cells (right), compared to non-electroporated OVCAR3 cells (left). Western blots confirmed pIgR-ablation in OVCAR3 cells. THP1 cells used as negative control and recombinant pIgR (rPIGR) used as positive control. WT represents wildtype (non-electroporated cells).

Figure 15:
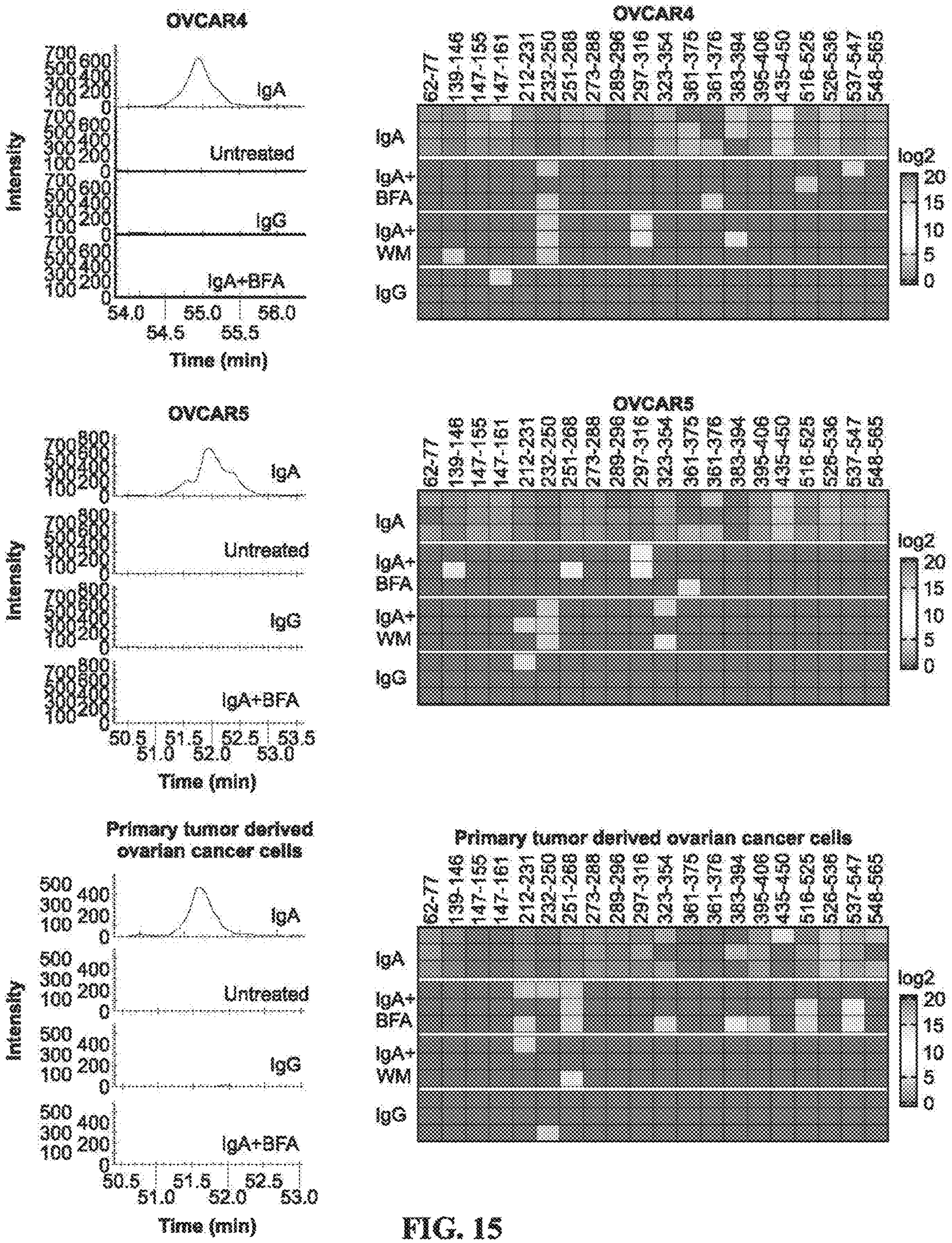

FIG. 15 OVCAR4 (top), OVCAR5 (middle) and primary HGSOC tumor cells (bottom) were incubated with 0.5 g/mL of irrelevant IgA or IgG for 8 hr in serum-free media in the presence of wortmannin (1 μM), brefeldin-A (1 μg/ml), or vehicle, and supernatants were then subjected to Mass Spectrometry. (Left) Heatmap of all peptides of the extracellular domain of pIgR (Right); (n=3 experiments). BFA, brefeldin-A. WM, wortmannin.

FIG. 16 (A) GSEA enrichment plots and (B) Heatmaps using normalized gene expression from RNA sequencing analysis from OVCAR3 cells with irrelevant IgA (0.5 μg/mL), IgG (0.5 μg/mL) or no treatment (in triplicate) for 24 hours (n=3 experiments).

FIG. 17. (A) Dose-dependent cytotoxic killing of OVCAR3 cells FSH targeted chimeric receptor T-cells is augmented by co-incubation with 0.5 μg/mL of irrelevant IgA, αTSPAN7-IgA or αBDNF-IgA compared to IgG, pepsinized-irrelevant IgA or PBS. Data shown are representative of 2 independent experiments. , p≤0.01; (unpaired two-tailed ttests). (B) Cytotoxic killing of autologous CD45- EpCAM+ tumor cells (with corresponding decrease of Annexin Vnegative-PInegative viable cells) by autologous T-cells (added at 1:1 ratio) is augmented by co-incubation with 0.5 μg/mL of autologous IgA or irrelevant IgA but not with autologous IgG, pepsinized autologous/irrelevant IgAs compared to uncoated cells. *, p≤0.001; NS, not significant (unpaired two-tailed t-tests). (C) Cytotoxic killing of pIgR+ OVCAR3 cells, but not pIgR-CRISPRed OVCAR3 cells, by FSH-targeted chimeric receptor T-cells (added at 1:1 ratio) is augmented by co-incubation with 0.5 μg/mL of irrelevant IgA compared to IgGcoated, uncoated cells. ***, p≤0.001; NS, not significant (unpaired two-tailed t-tests).

Figure 18:
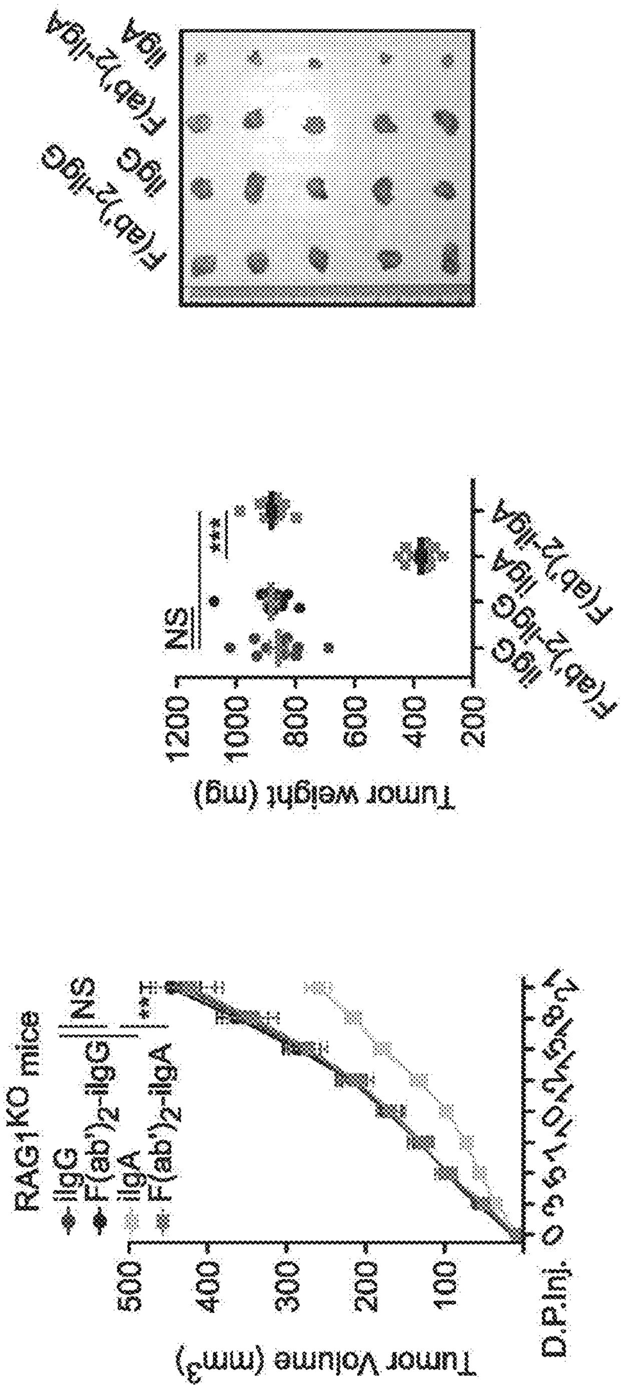

FIG. 18. Tumor growth curves (left), as well as tumor volume (right) and weight (center) in OVCAR3-tumor-bearing RAG1-KO mice receiving full length or pepsinized (Fc-removed) irrelevant IgG or IgA antibodies. Curves and tumor weights were pooled from 2 independent experiments (10 mice/group, total). , p≤0.01; *, p≤0.001; NS, Not significant; (paired two-tailed t-tests).

Figure 19:
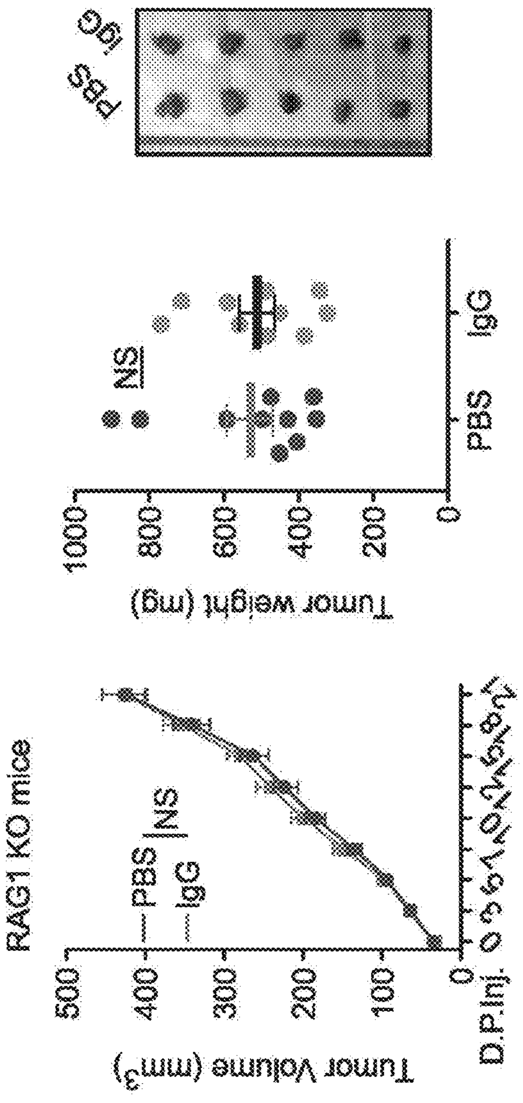

FIG. 19. Tumor growth curves (left), as well as tumor volume (right) and weight (center) in OVCAR3-tumor-bearing RAG1-KO mice receiving irrelevant IgG antibodies or vehicle (PBS). Curves and tumor weights were pooled from 2 independent experiments (10 mice/group, total). NS, Not significant; (paired two-tailed t-tests).

Figures 20A, 20B:
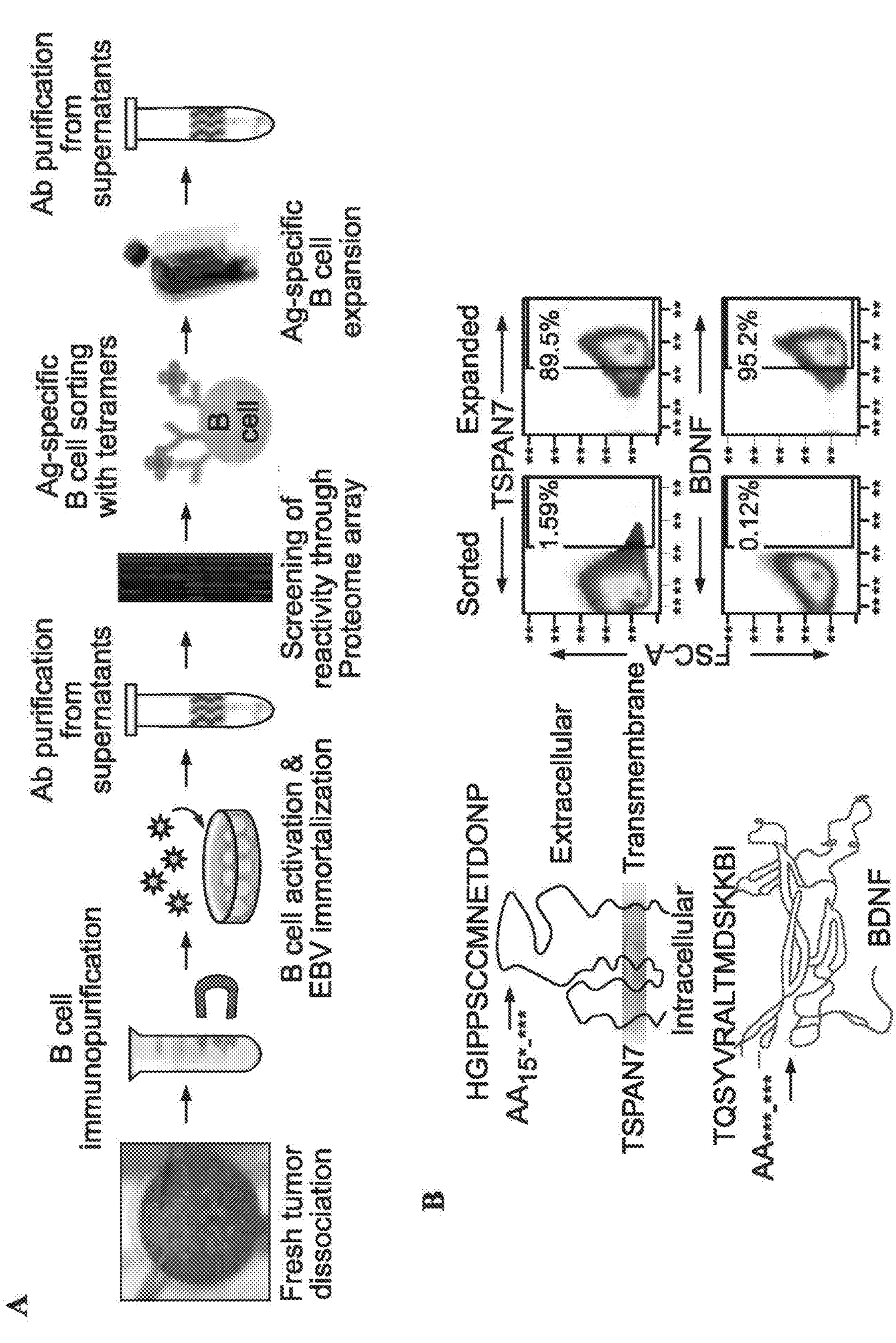
Figure 20:
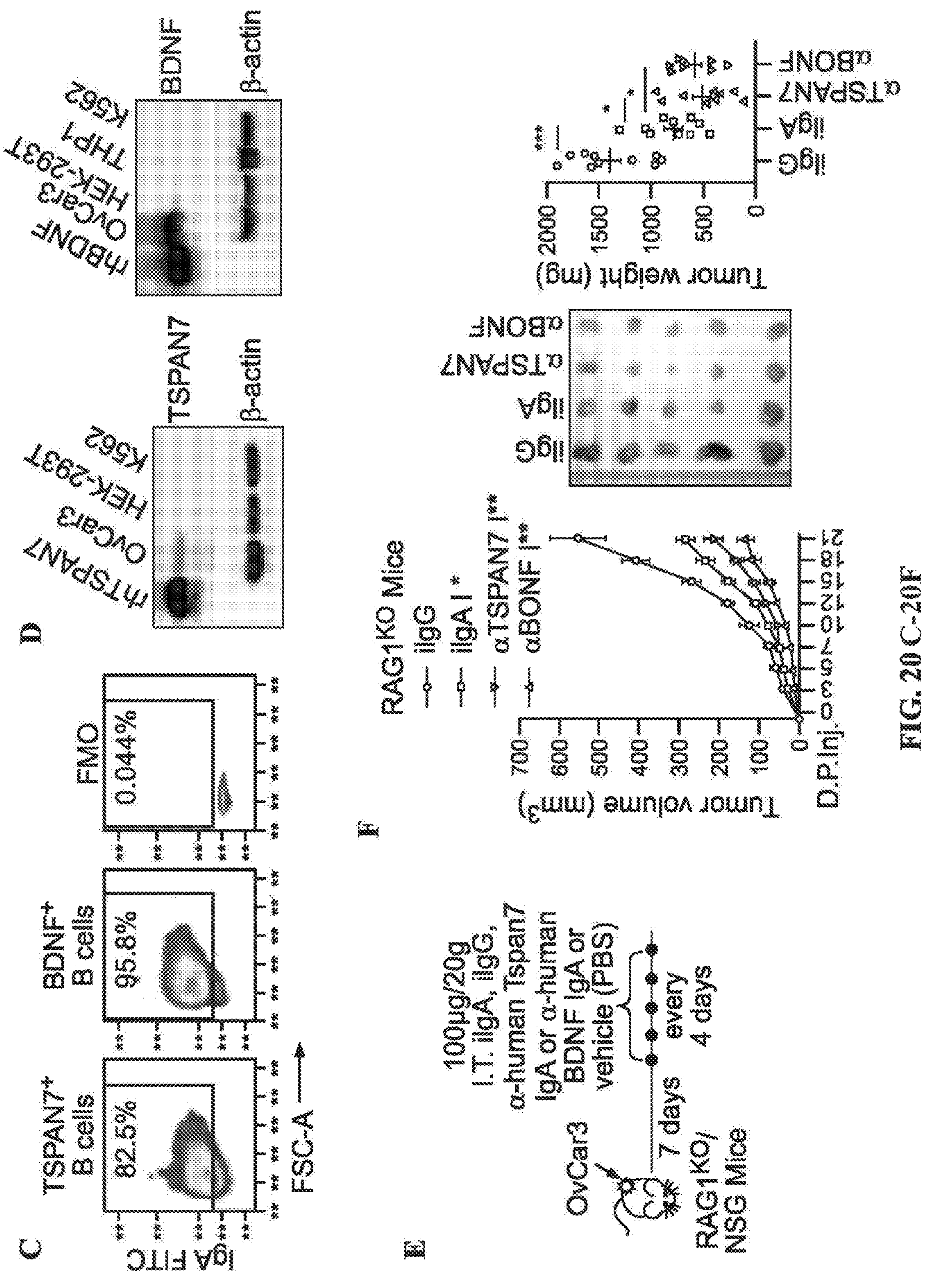
Figure 20G:
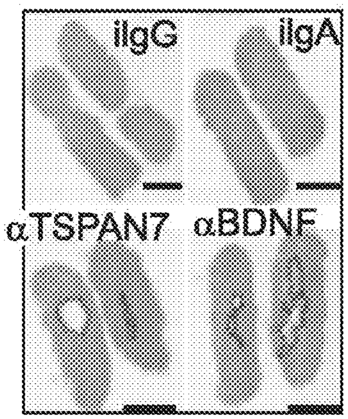

FIG. 20. Tumor antigen-specific IgA produced in the ovarian cancer microenvironment antagonizes ovarian cancer progression. (A) Schematic representation of the optimized protocol for separating, immortalizing, characterizing and selecting tumor-reactive B-cells from HGSOCs. (B) Tetramers spanning the indicated loop in BDNF or the extracellular domain of TSPN7 were used to sort reactive B-cells immortalized from 10 independent HGSOCs. The reactivity of expanded cells was confirmed using the same tetramers. (C) IgA represents the majority of TSPAN7- or BDNF-reactive B-cells sorted from HGSOCs. (D) IgA purified from TSPAN7- and BDNF-reactive immortalized B-cells recognizes the corresponding recombinant proteins in Western-blot analysis, along with endogenous TSPAN7 and BDNF expressed in OVCAR3 cells. HEK-293T, THP1 and K562 cells included as negative controls (E) Schematic of the design of the experiment shown in (F,H). (F) Tumor growth curves (left), as well as tumor volume (center) and weight (right) in tumor-bearing RAG1-KO mice receiving control or tumor derived antibodies. Curves and tumor weights were pooled from 2 independent experiments (10 mice/group, total). *, p≤0.05; , p≤0.01; *, p≤0.001; (paired two-tailed t-tests). (G) Representative images of central necrosis in tumors from mice receiving IgA from tumor-derived B-cells. Bar, 4 mm. (H) Antibodies used in (F) were digested with pepsin to remove their Fc domain and used to treat OVCAR3 tumor-bearing RAG1-KO mice under identical conditions. Growth curves and tumor weight are pooled from 2 independent experiments (10 mice/group, total). *, p≤0.05; , p≤0.01; *, p≤0.001; NS, not significant (paired two-tailed t-tests). (I) Tumor growth curves (left) tumor weight (center) and volume (right) in tumor-bearing NSG mice receiving control or tumor-derived antibodies. Curves and tumor weights pooled from 2 independent experiments (10 mice/group, total). , p≤0.01; *, p≤0.001; NS, not significant (paired two-tailed t-tests). (J) Tumor growth curves (left), tumor weight (center) and volume (right) in tumor-bearing RAG1-KO mice receiving control or tumor-derived antibodies with or without IP injections of α-NK1.1 antibodies or isotype controls. Curves and tumor weights pooled from 2 independent experiments (10 mice/group, total). *, p≤ 0.05; *, p≤0.001; NS, not significant (paired two-tailed t-tests). (K) Scatter bar-graph and representative dot plots showing binding of IgA-antibodies to splenic-CD11b+ cells from tumor-bearing RAG1-KO mice (n=10), after incubation with Fcα/μR (CD351)-neutralizing antibodies or isotype controls. *, p≤0.001; (unpaired two-tailed t-tests). (L) Cytotoxic killing of OVCAR3 tumor cells by splenic myeloid cells from tumor-bearing RAG1-KO mice (1:1 ratio) is augmented by coating the tumor cells with 0.5 μg/mL of tumor-derived αTSPAN7, and inhibited by neutralizing CD351 (n=3). Representative of 2 independent experiments. *, p≤ 0.05; NS, not significant (unpaired two-tailed t-tests). (M) Increased accumulation of CD351+ myeloid cells in xenografts in RAG1-KO mice treated with intra-tumoral α-TSPAN7, compared to irrelevant IgA or vehicle, irrespectively of NK1.1-depletion (n=5). Representative FACS-dot plots show CD351+ cells in viable CD45+CD11b+ cells. *, p≤0.05; **, p≤0.01; NS, not significant (unpaired two-tailed t-tests). (N) Tumor growth curves (left), tumor weight (center) and volume (right) in wild-type pIgR+ (WT) or pIgR-ablated (PIGRCRISPR) OVACR3 tumor-bearing RAG1-KO mice receiving control or tumor-derived antibodies. Tumor growth represented from one experiment, performed twice (5 mice/group); tumor weights are pooled from two experiments (10 mice/group, total). *, p≤0.05; , p≤0.01; *, p≤0.001; NS, not significant (paired two-tailed t-tests).

FIG. 21. (A) Representative TUNEL (ALEXA FLUOR 647™) staining images in xenograft tumors developed in RAG1-KO mice. (B) Estimation of TUNEL-positive cells normalized to tumor area (2 experiments, total n=10, each group). *, p≤0.05; (unpaired two-tailed t-tests) (C) Tumor area quantification (2 experiments, total n=10, each group). ***, p≤0.10-0.001; (unpaired two-tailed t-tests) (D) Quantification of irrelevant IgA and αTSPAN7-IgA antibody uptake in OVACR3-xenografts (2 experiments, total n=10, each group). *, p≤0.05; (unpaired two-tailed t-tests).

Figure 22:
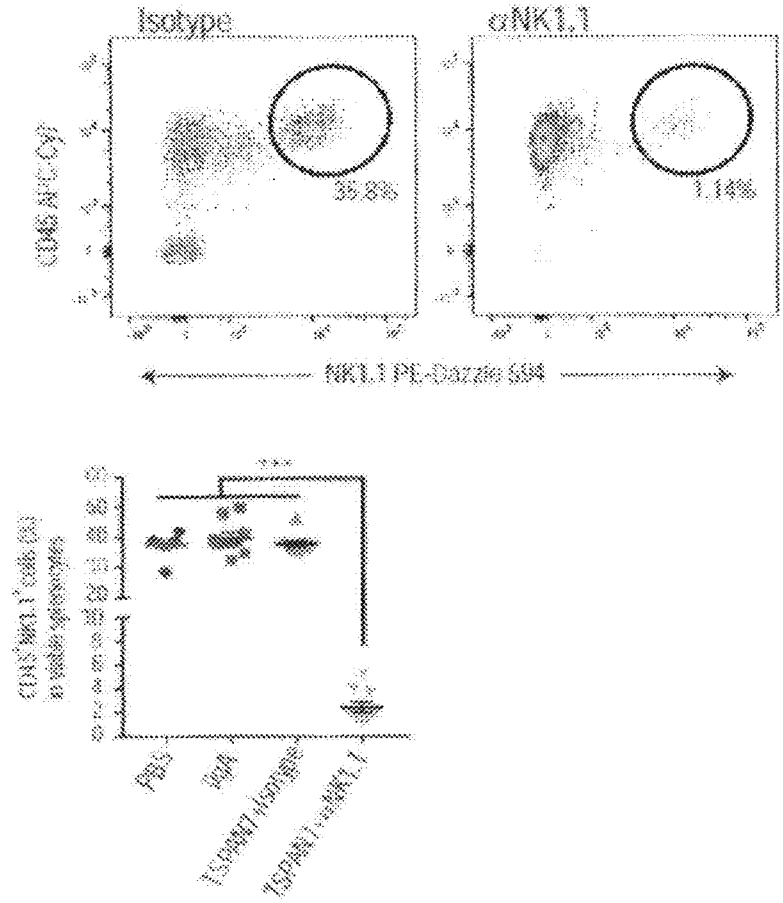

FIG. 22. Dot plots showing FACS analysis of splenocytes for NK1.1 depletion in RAG1-KO mice (top). Scattered plot showing CD45+NK1.1+ cells percentages among viable splenocytes in respective treatment group mice (2 experiments, total n=10, each group) (bottom). ***, p≤0.001; (unpaired two-tailed t-tests).

Figure 23:
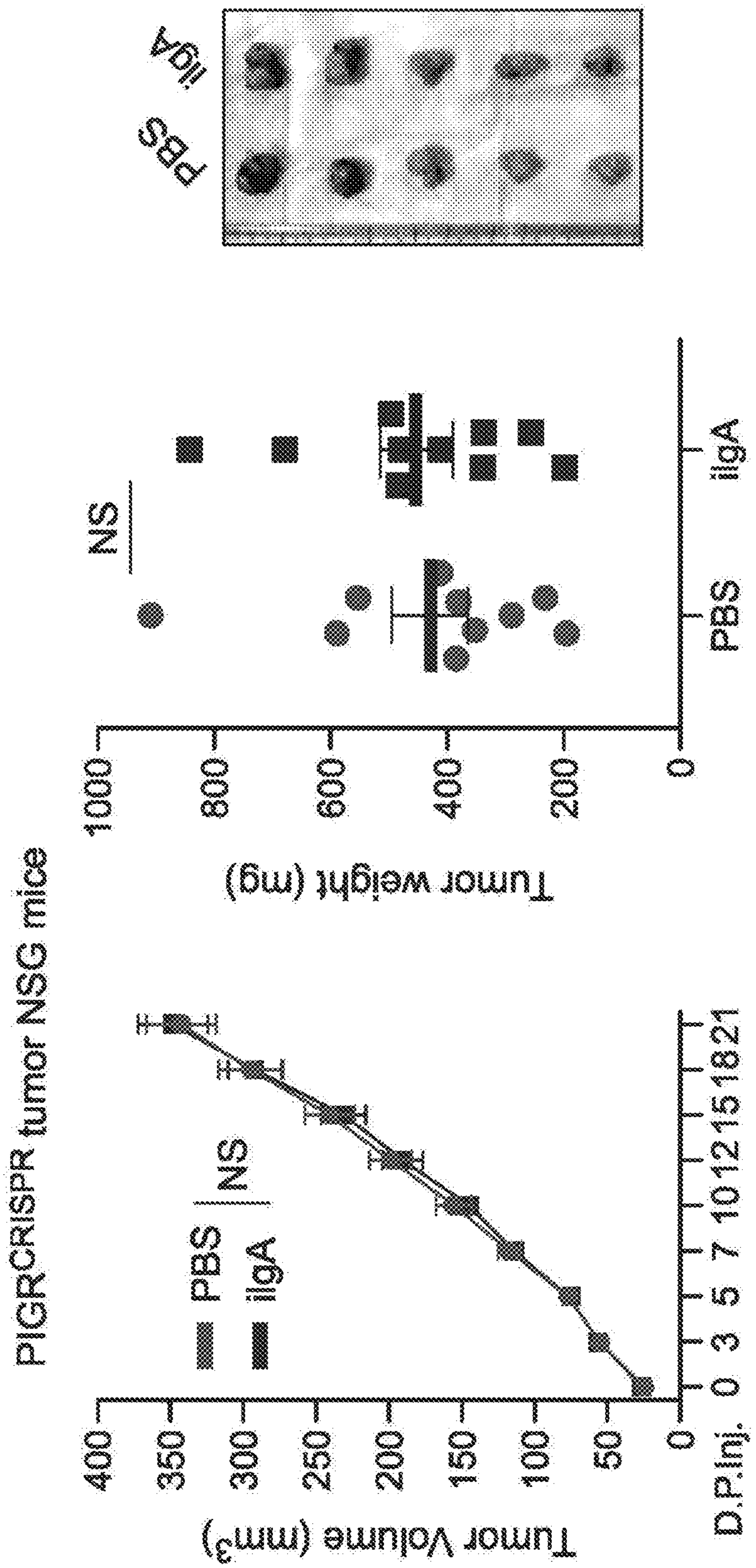

FIG. 23. Tumor growth curves (left), as well as tumor volume (right) and weight (center) in pIgR-CRISPRed-OVCAR3-tumor-bearing NSG mice receiving irrelevant IgA antibodies or vehicle (PBS). Curves and tumor weights were pooled from 2 independent experiments (10 mice/group, total). NS, Not significant; (paired two-tailed t-tests).

FIG. 24. (A) Mean internalized intensity of antibodies (APC) were quantified and scattered bar graph showing comparison of antibody internalization in different treatment conditions where each dot represents quantitation from one cell. ***, p≤0.001; NS, Not significant (unpaired two-tailed t-tests). (B) Pathway analysis of RNA sequencing from OVCAR3 cells treated with irrelevant IgA (0.5 μg/mL), αTSPAN7-IgA (0.5 g/mL), αBDNFIgA or no treatment for 24 hours (n=3 experiments).

FIG. 25. Oligoclonal IgA responses in Tertiary Lymphoid Structures are associated with immune protection in human ovarian cancer. (A) Representative TLS in one of the HGSOCs analyzed. Arrows point to interdigitating T-cells within the B-cell zone. Nearest neighbor analysis-derived scattered graph showing median distance between each T-cell and its nearest B cell in each tumor core of MCC cohort, grouped into tertiary lymphoid structure (TLS)-positive and TLS-negative by visual inspection of proximal B- and T-cell conglomerates. Each dot represents one core, where tumor cores only positive for both the cell types were included in the analysis. **, p≤0.01 (Wilcoxon rank-sum test). (B) Immune cell spatial interaction networks for TLS+ and TLS-tumors from the Moffitt cohort (93 HGSOC patients). Link width indicates the strength of the interaction, while color shows both the strength and direction of the interaction. Values less than 1 indicate repulsion, while values greater than 1 indicate attraction. In TLS+ samples, CD4+ T-cells, CD8+ T-cells, and CD20+ B-cells are strongly interacting, but less so in TLS-samples. (C) The presence of TLS, identified in 21% of HGSOCs in the Moffitt cohort, is associated with improved outcome. *, p≤0.05; (log-rank (Mantel-Cox) test) (D) The presence of TLS is associated with denser infiltrates of CD19+ B-cells (left), CD3+CD4+ (center) and CD3+CD8+ T-cells (right), in this cohort. ***, p≤0.001; (unpaired two-tailed t-tests) (E) Representative IGHV repertoire of laser-captured microdissected TLS from 4 different human HGSOCs (left). CDR3 sequences of 80% of the IGHV sequences in each TLS (center). Representative IGHV repertoire of the whole tumor (right). (F) Representative combined staining of IgA/IgG/IgM, CD3 and CD20 in 6 different TLS. Bar, 75-μm. (G) Left, Volcano plot comparing gene expression between TLS-proximal (<500 μm) and distant cancer cells. Right, Pathway analysis showing important pathways that are upregulated in the TLS-proximal cancer cells, not in distant ones (n=4).

FIG. 26. (Top) Example of laser-captured microdissection of a TLS in OCT sections from an independent cohort of 40 HGSOC patients. (Bottom) Representative IGHV repertoire of 3 additional laser-captured microdissected TLS from different human HGSOCs, along with the IGHV repertoire of the corresponding whole tumor.

Figure 27:
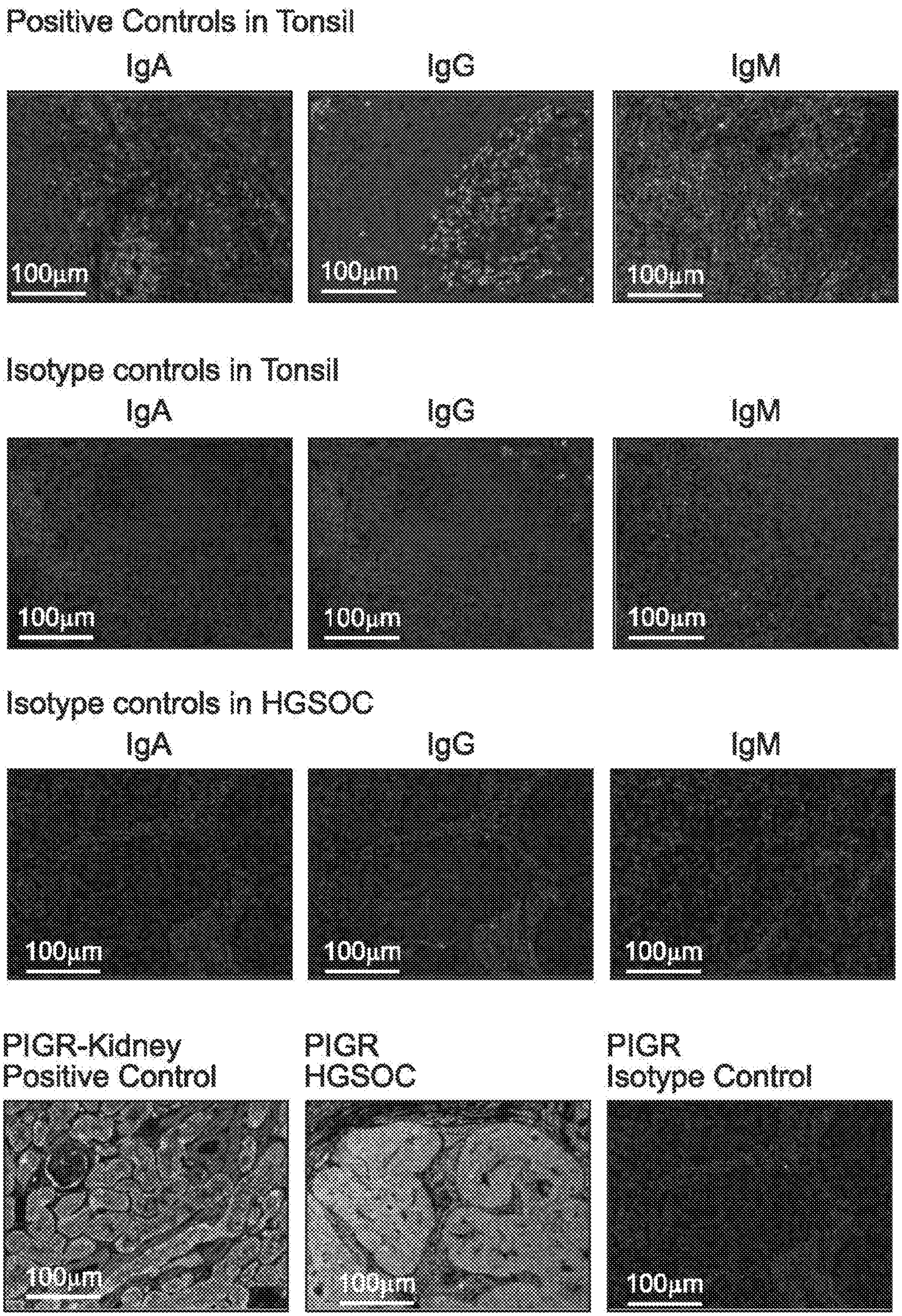

FIG. 27. Antibody optimization: Immunofluorescence staining of tonsil tissue sections with anti-human IgA, IgG, IgM antibodies and respective isotype controls; HGSOC tissue sections were stained with isotype controls for IgA, IgG, IgM; Healthy kidney section and HGSOC section stained with anti-human pIgR antibody and respective isotype control.

Figure 28:
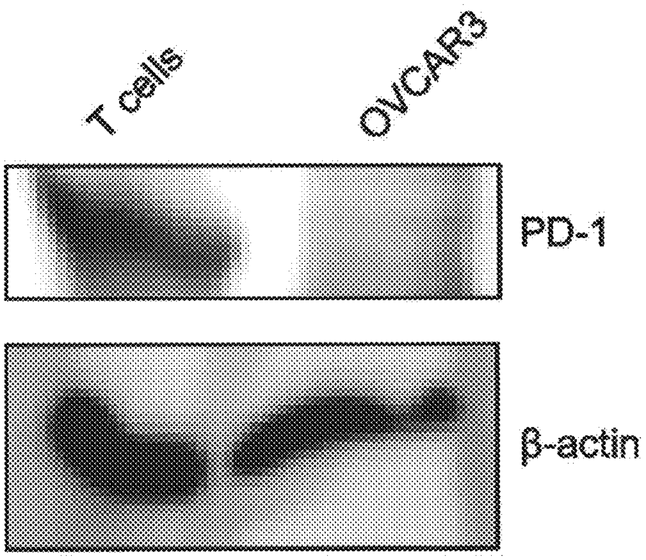

FIG. 28 shows a western blot showing positive staining of PD-1 by our IgA using activated T cells, but not OVCAR3 tumor cells.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purposes. A control can be "positive" or "negative."

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

A "decrease" can refer to any change that results in a smaller gene expression, protein expression, amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The terms "prevent," "preventing," "prevention," and grammatical variations thereof as used herein, refer to a method of partially or completely delaying or precluding the onset or recurrence of a disease and/or one or more of its attendant symptoms or barring a subject from acquiring or reacquiring a disease or reducing a subject's risk of acquiring or reacquiring a disease or one or more of its attendant symptoms.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular anti-PD1 antibody is disclosed and discussed and a number of modifications that can be made to a number of molecules including the anti-PD1 antibody are discussed, specifically contemplated is each and every combination and permutation of an anti-PD1 antibody and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

T cells play an essential role in the anti-cancer immune response. T cell activation depends on the initial antigen-specific signal, presented via the antigen-loaded major histocompatibility complex (MHC) to the T cell receptor, and on activation of the costimulatory molecule CD28 by binding of CD80/86. T cells also express coinhibitory molecules that are capable of downregulating the immune response. One major coinhibitory receptor is programmed death 1 (PD1).

Shown herein is that both IgA and IgG produced at tumor beds exert significant immune pressure against ovarian cancer progression by: 1) Targeting extracellular and/or intracellular antigens at endosomal compartments (IgA) (for example, mutant KRas or mutant PI3K). and 2) neutralizing tumor-promoting cell surface or secreted molecules (IgG and IgA). Accordingly, the characterization of B cells immortalized from human ovarian carcinomas identifies novel therapeutic targets as well as novel immunotherapeutic tools. This reasoning for this is based on several findings: First, unexpectedly, it was found that most B cells in human ovarian carcinomas are producing IgA that coats the surface of polymeric IgA Receptor (pIgR)+ tumor cells in ~50% of tumors. Second, a protocol for sorting, activating and immortalizing B cells from freshly dissociated ovarian carcinomas was optimized. B cells from 8 different patients producing high titers of IgA and IgG have been immortalized so far, with 80% effectiveness. Third, novel arrays that contain >80% of the human proteome (e.g., from CDI) now allow the characterization of the specificities of tumor-derived antibodies.

The terms "PD1", "PD1" and "Programmed cell death protein 1" refer to a member of the CD28 superfamily that delivers negative signals upon interaction with its two ligands, PD1 or PD-L2. PD1 and its ligands are broadly expressed and exert a wider range of immunoregulatory roles in T cells activation and tolerance compared with other CD28 members. PD1 was isolated as a gene up-regulated in a T cell hybridoma undergoing apoptosis and was named program death 1. PD1 has two ligands, programmed death ligand-1 (PD-L1) and PD-L2, of which PD-L1 is most widely expressed. PD-L1, also known as CD274, Programmed Cell Death 1 Ligand 1 (PDCD1LG1 or PD1) or B7-H1, is a type I transmembrane glycoprotein composed of IgC- and IgV-type extracellular domains, which binds to PD1.

Binding of PD-L1 to PD1 transduces an inhibitory signal to the T cell, resulting in inhibition of T cell proliferation, reduced secretion of effector cytokines, and potentially exhaustion. By up-regulating PD1 expression levels, tumor cells are capable of escaping immune recognition and attack. PD1 is expressed on a wide variety of tumors, including breast cancer, gastric cancer, renal cell cancer, ovarian cancer, non-small lung cancer, melanoma, and hematological cancers. In general, PD-L1 and PD1 have been demonstrated to be poor prognostic factors as high expression levels are associated with poor outcome of cancer patients. Preclinical studies with anti-PD1 and anti-PD-L1 antibodies have shown promising anti-tumor effects and have led to the initiation of several clinical investigations. Early clinical trials demonstrated objective and durable (>1 year) responses in patients with treatment-refractory, advanced melanoma, renal cell carcinoma, non-small cell lung cancer, and ovarian cancer. Because of these impressive results, phase II/III studies are currently further exploring the therapeutic efficacy of these agents. Due to the impressive efficacy in melanoma patients, the FDA has recently granted accelerated approval of pembrolizumab (anti-PD1 antibody) for the treatment of patients with advanced or unresectable melanoma following progression on prior therapies. Nevertheless, only about 30% of patients see successful outcomes with the presently available anti-PD1 antibodies. Thus, new more effective and more universal anti-PD1/PDL-1 antibodies, bi-specific antibodies and immunotoxins are needed.

Shown herein is that both IgA and IgG produced at tumor beds exert significant immune pressure against ovarian cancer progression by: 1) Targeting intracellular antigens at endosomal compartments (IgA); and 2) neutralizing tumor-promoting cell surface or secreted molecules (IgG). Accordingly, the characterization of B cells immortalized from human ovarian carcinomas identifies novel therapeutic targets as well as novel immunotherapeutic tools. This reasoning for this is based on several findings: First, unexpectedly, it was found that most B cells in human ovarian carcinomas are producing IgA that coats the surface of pIgR+ tumor cells in ~50% of tumors. Second, a protocol for sorting, activating and immortalizing B cells from freshly dissociated ovarian carcinomas was optimized. B cells from 8 different patients producing high titers of IgA and IgG have been immortalized so far, with 80% effectiveness. Third, novel arrays that contain >80% of the human proteome (e.g., from CDI) now allow the characterization of the specificities of tumor-derived antibodies. Thus, the present disclosure relates to an anti-PD1 antibodies and immunotoxins for use in a method of treating, inhibiting, decreasing, reducing, ameliorating, and/or preventing a tumor, preferably a PD1-positive tumor, in a patient. Herein is shown that labelled anti-PD1 antibodies are targeted specifically to tumors expressing PD1. Anti-PD1 antibodies coupled to a toxin can therefore be used in therapy in order to target and kill tumor cells.

As used herein, the term ‘immunotoxin” has its general meaning in the art. By “immunotoxin”, it is meant a chimeric protein made of an antibody or modified antibody or antibody fragment (also called in the present application “antibody”), attached to a fragment of a toxin. The antibody of the immunotoxin is covalently attached to the fragment of a toxin. Preferably, the fragment of the toxin is linked by a linker to the antibody or fragment thereof. Said linker is preferably chosen from 4-mercaptovaleric acid and 6-maleimidocaproic acid.

The term “anti-PD1 immunotoxin” refers to an antibody-drug conjugate (ADC) wherein the antibody moiety is an anti-PD1 antibody and wherein said anti-PD1 antibody is linked to a toxin. Such a toxin could be a native or engineered toxin, and may have been de-immunized to reduce immunogenicity. Upon binding to PD1 on its target cells, the immunotoxin enters the cells and kills the target cells. As used herein, the term “antibody” has its general meaning in the art. The term “anti-PD1 antibody” refers to an antibody that binds specifically to PD1. Preferably, said antibody does not bind to PD-L2.

In one aspect, the disclosed anti-PD1 antibodies could be fused to other binding molecules to create bi-specific antibody molecules. Such molecules could utilize the PD1 binding component to target to PD1 positive tumors, and could be linked to antibodies to LAG-3, TGF-β, OX40, ICOS, LIGHT, and a variety of other T cell surface antigens.

Binding Molecules

As used herein the term “binding molecule” refers to an intact immunoglobulin including monoclonal antibodies, polyclonal antibodies, chimeric antibodies, humanized or human antibodies, as well as antibodies fragments and functional variants including antigen-binding and/or variable domain comprising fragment of an immunoglobulin that competes with the intact immunoglobulin for specific binding to the binding partner of the immunoglobulin, e.g. PD1.

In one aspect, the disclosed PD1 binding molecules can comprise an anti-PD1 antibody (for example, an anti-PD1 antibody). The term “antibodies” is used herein in a broad sense and includes both polyclonal and monoclonal antibodies. As used herein, the term “antibody” encompasses, but is not limited to, whole immunoglobulin (i.e., an intact antibody) of any class. In addition to intact immunoglobulin molecules, also included in the term “antibodies” are fragments or polymers of those immunoglobulin molecules, and human or humanized versions of immunoglobulin molecules or fragments thereof.

Native antibodies are usually heterotetrameric glycoproteins, composed of two identical light (L) chains and two identical heavy (H) chains. The disclosed PD1 binding molecules whether monoclonal antibodies, polyclonal antibodies, chimeric antibodies, humanized or human antibodies, as well as antibodies fragments and functional variants can comprise all or a portion of light and heavy chains.

In a complete antibody, typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant (C(H)) domains. Each light chain has a variable domain at one end (V(L)) and a constant (C(L)) domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively. Thus, in one aspect, disclosed herein are PD1 binding molecules (such as for example, an isolated PD1 binding molecules comprising a heavy chain variable domain comprising a CDR3 as set forth in SEQ ID NO: 5), wherein the binding molecule is an antibody and the antibody has an isotype of IgA. In one aspect, the IgA antibody can include any of the PD1 molecules disclosed herein including ones comprising a variable heavy chain domain as set forth in SEQ ID NO: 1 and a variable light chain domain as set forth in SEQ ID NO: 2.

The term "variable" is used herein to describe certain domains of the heavy and light chains that differ in sequence among antibodies and are used in the binding and specificity of each particular antibody for its particular antigen. However, the variability is not usually evenly distributed through the variable domains of antibodies. The more highly conserved portions of the variable domains are called the framework (FR). The variable domains of native heavy and light chains each comprise four FR regions, largely adopting a β-sheet configuration, connected by three complementarity determining regions (CDRs), which form loops connecting, and in some cases forming part of, the β-sheet structure. The variability is typically concentrated in the CDRs or hypervariable regions both in the light chain and the heavy chain variable domains.

The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The term "complementary determining regions" as used herein means sequences within the variable regions of binding molecules, such as immunoglobulins, that generate the antigen binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of post-translational modifications of proteins.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically.

The constant domains are not involved directly in binding an antibody to an antigen, but exhibit various effector functions, such as participation of the antibody in antibody-dependent cellular toxicity.

In one aspect, disclosed herein are isolated PD1 binding molecules comprising a heavy chain variable domain comprising a Complementary Determining Region (CDR) 3 (CDR3) as set forth in SEQ ID NO: 5. In one aspect, the one or more heavy chain variable domain CDRs can comprise one or both CDRs as set forth in SEQ ID NO: 3 and SEQ ID NO: 4 (for example a binding molecule comprising a heavy chain variable domain comprises the CDRs as set forth in SEQ ID NO: 5 and SEQ ID NO: 3, SEQ ID NO: 5 and SEQ ID NO: 4, or SEQ ID NO: 3, SEQ ID NO: 4, and SEQ ID NO: 5). In one aspect, the isolated binding molecule can comprise the variable heavy chain domain as set forth in SEQ ID NO: 1.

It is understood and herein contemplated that the disclosed complimentary determining regions of the heavy chain variable domains in the disclosed PD1 binding molecules can be contiguous or separated by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids. Thus, disclosed herein are PD1 binding molecules comprising heavy chain variable domains comprising at least two CDRs wherein the first CDR is separated from the second CDR by 10, 11, 12, 13, 14, 15, 16, 17, 18, 19, or 20 amino acids. and wherein the second CDR and the third CDR are separated by 25, 26, 27, 28, 29, 30, 31, 32, 33, 34, 35, 36, 37, 38, 39, or 40 amino acids.

It is understood and herein contemplated that the PD1 binding molecules can further comprise a light chain variable domain in addition to a heavy chain variable domain. In one aspect disclosed herein are isolated PD1 binding molecules of any preceding aspect, wherein the binding molecule further comprises a light chain variable domain comprising at least one CDR as set forth in SEQ ID NO: 6, SEQ ID NO: 7, or SEQ ID NO: 8 (such as, for example, a carriable light chain domain comprising the CDRs as set forth in SEQ ID NO: 6 and SEQ ID NO: 7; SEQ ID NO: 6 and SEQ ID NO: 8; SEQ ID NO: 7 and SEQ ID NO: 8; or SEQ ID NO: 6, SEQ ID NO: 7, and SEQ ID NO: 8). In one aspect, the isolated binding molecule can comprise the variable light chain domain as set forth in SEQ ID NO: 2 (for example a PD1 binding molecule comprising a variable heavy chain domain as set forth in SEQ ID NO: 1 and a variable light chain domain as set forth in SEQ ID NO: 2).

It is understood and herein contemplated that the disclosed complimentary determining regions of the light chain variable domains in the disclosed PD1 binding molecules can be contiguous or separated by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids. Thus, disclosed herein are PD1 binding molecules comprising light chain variable domains comprising at least two CDRs wherein the first CDR is separated from the second CDR by 10, 11, 12, 13, 14, 15, 16, 17, 18, 19, or 20 amino acids. and wherein the second CDR and the third CDR are separated by 25, 26, 27, 28, 29, 30, 31, 32, 33, 34, 35, 36, 37, 38, 39, or 40 amino acids.

As noted above the disclosed PD1 binding molecules (including, but not limited to neutralizing PD1 binding molecules such as, for example, neutralizing anti-PD1 antibodies) can also be fragments of antibodies. As used herein, the term "antibody or fragments thereof" encompasses chimeric antibodies and hybrid antibodies, with dual or multiple antigen or epitope specificities, and fragments, such as F(ab')2, Fab', Fab, Fv, sFv, dAb, complementarity determining region (CDR) fragments, single-chain antibodies (scFv), bivalent single-chain antibodies, diabodies or other bi-specific antibodies, triabodies, tetrabodies, (poly) peptides that contain at least a fragment of an immunoglobulin that is sufficient to confer specific antigen binding to the (poly) peptide, etc., including hybrid fragments. Thus, fragments of the antibodies that retain the ability to bind their specific antigens are provided. For example, fragments of antibodies which maintain PD1 binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies). Conjugated antibodies or fragments refer to antibodies or fragments that are operatively linked or otherwise physically or functionally associated with an effector moiety or tag, such as inter alia a toxic substance, a radioactive substance, fluorescent substance, a liposome, or an enzyme as described, for example, in U.S. Pat. No. 4,704,692, the contents of which are hereby incorporated by reference.

Regardless of structure, the antigen-binding fragments disclosed herein can bind with the same antigen that is recognized by the intact immunoglobulin. An antigen-binding fragment can comprise a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least 200 contiguous amino acid residues, or at least contiguous 250 amino acid residues of the amino acid sequence of the binding molecule.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

The term "functional variant", as used herein, refers to a binding molecule that comprises a nucleotide and/or amino acid sequence that is altered by one or more nucleotides and/or amino acids compared to the nucleotide and/or amino acid sequences of the parent binding molecule and that is still capable of competing for binding to the binding partner, e.g. PD1 (including PD1), with the parent binding molecule. In other words, the modifications in the amino acid and/or nucleotide sequence of the parent binding molecule do not significantly affect or alter the binding characteristics of the binding molecule encoded by the nucleotide sequence or containing the amino acid sequence, i.e. the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may comprise natural as well as non-natural nucleotides and amino acids.

As disclosed herein, the binding molecules, antibodies, fragments, and variants are able to specifically bind to an antigenic target, such as, for example, PD1. The term "specifically binding", as used herein, in reference to the interaction of a binding molecule, e.g. an antibody, and its binding partner, e.g. an antigen, means that the interaction is dependent upon the presence of a particular structure, e.g. an antigenic determinant or epitope, on the binding partner. In other words, the antibody preferentially binds or recognizes the binding partner even when the binding partner is present in a mixture of other molecules. The binding may be mediated by covalent or non-covalent interactions or a combination of both. In yet other words, the term "specifically binding" means immunospecifically binding to an antigen or a fragment thereof and not immunospecifically binding to other antigens. A binding molecule that immunospecifically binds to an antigen may bind to other peptides or polypeptides with lower affinity as determined by, e.g., radioimmunoassays (RIA), enzyme-linked immunosorbent assays (ELISA), BIAcore, or other assays known in the art. Binding molecules or fragments thereof that immunospecifically bind to an antigen may be cross-reactive with related antigens. Preferably, binding molecules or fragments thereof that immunospecifically bind to an antigen do not cross-react with other antigens.

In one aspect, the disclosed antibodies or binding molecules disclosed herein can be human antibodies or human binding molecules. The term "human", when applied to binding molecules as defined herein, refers to molecules that are either directly derived from a human or based upon a human sequence. When a binding molecule is derived from or based on a human sequence and subsequently modified, it is still to be considered human as used throughout the specification. In other words, the term human, when applied to binding molecules is intended to include binding molecules having variable and constant regions derived from human germline immunoglobulin sequences based on variable or constant regions either or not occurring in a human or human lymphocyte or in modified form. Thus, the human binding molecules may include amino acid residues not encoded by human germline immunoglobulin sequences, comprise substitutions and/or deletions (e.g., mutations introduced by for instance random or site-specific mutagenesis in vitro or by somatic mutation in vivo). “Based on” as used herein refers to the situation that a nucleic acid sequence may be exactly copied from a template, or with minor mutations, such as by error-prone PCR methods, or synthetically made matching the template exactly or with minor modifications. Semisynthetic molecules based on human sequences are also considered to be human as used herein.

Optionally, the antibodies are generated in other species and “humanized” for administration in humans. Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature,* 321:522-525 (1986); Riechmann et al., *Nature,* 332:323-327 (1988); and Presta, *Curr. Op. Struct. Biol.,* 2:593-596 (1992)).

Methods for humanizing non-human antibodies are well known in the art. Generally, a humanized antibody has one or more amino acid residues introduced into it from a source that is non-human. These non-human amino acid residues are often referred to as “import” residues, which are typically taken from an “import” variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody. Accordingly, such “humanized” antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. 90. The choice of human variable domains, both light and heavy, to be used in making the humanized antibodies is very important in order to reduce antigenicity. According to the “best-fit” method, the sequence of the variable domain of a rodent antibody is screened against the entire library of known human variable domain sequences. The human sequence which is closest to that of the rodent is then accepted as the human framework (FR) for the humanized antibody (Sims et al., *J. Immunol.,* 151:2296 (1993) and Chothia et al., *J. Mol. Biol.,* 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993)).

In some aspect, it can be important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679, published 3 Mar. 1994).

Disclosed are hybridoma cells that produces the monoclonal antibody. The term “monoclonal antibody” as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include “chimeric” antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816,567 and Morrison et al., *Proc. Natl. Acad. Sci. USA,* 81:6851-6855 (1984)).

Monoclonal antibodies may be prepared using hybridoma methods, such as those described by Kohler and Milstein, *Nature,* 256:495 (1975) or Harlow and Lane. *Antibodies, A Laboratory Manual*. Cold Spring Harbor Publications, New York, (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. Preferably, the immunizing agent comprises PD1. Traditionally, the generation of monoclonal antibodies has depended on the availability of purified protein or peptides for use as the immunogen. More recently DNA based immunizations have shown promise as a way to elicit strong immune responses and generate monoclonal antibodies. In this approach, DNA-based immunization can be used, wherein DNA encoding a portion of PD1 expressed as a fusion protein with human IgG1 is injected into the host animal according to methods known in the art (e.g., Kilpatrick K E, et al. Gene gun delivered DNA-based immunizations mediate rapid production of murine monoclonal antibodies to the Flt-3 receptor. *Hybridoma.* 1998 December; 17 (6): 569-76; Kilpatrick K E et al. High-affinity monoclonal antibodies to PED/PEA-15 generated using 5 microg of DNA. *Hybridoma.* 2000 August; 19 (4): 297-302, which are incorporated herein by referenced in full for the methods of antibody production) and as described in the examples.

An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing domains of an anti-PD1 antibody as fusion proteins. The antigen is produced by inserting a gene fragment in-frame between the signal sequence and the mature protein domain of the anti-PD1 antibody nucleotide sequence. This results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, *J. Immunol.,* 133:3001 (1984); Brodeur et al., "Monoclonal Antibody Production Techniques and Applications" Marcel Dekker, Inc., New York, (1987) pp. 51-63). The culture medium in which the hybridoma cells are cultured can then be assayed for the presence of monoclonal antibodies directed against PD1. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane Antibodies, *A Laboratory Manual* Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The term "isolated", when applied to binding molecules as defined herein, refers to binding molecules that are substantially free of other proteins or polypeptides, particularly free of other binding molecules having different antigenic specificities, and are also substantially free of other cellular or tissue material and/or chemical precursors or other chemicals. For example, when the binding molecules are recombinantly produced, they are preferably substantially free of culture medium, and when the binding molecules are produced by chemical synthesis, they are preferably substantially free of chemical precursors or other chemicals, i.e., they are separated from chemical precursors or other chemicals which are involved in the synthesis of the protein. Preferably, substantially free means that the binding molecule will typically comprise about 50%, 60%, 70%, 80% or 90% W/W of a sample, more usually about 95%, and preferably will be over 99% pure.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Optionally, such a non-immunoglobulin polypeptide is substituted for the constant domains of an antibody or substituted for the variable domains of one antigen-combining site of an antibody to create a chimeric bivalent antibody comprising one antigen-combining site having specificity for PD1 (including PD1) and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, *Antibodies, A Laboratory Manual*, Cold Spring Harbor Publications, New York, (1988). Papain digestion of antibodies typically produces two identical antigen binding fragments, called Fab fragments, each with a single antigen binding site, and a residual Fc fragment.

Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

Alternatively, the disclosed antibodies can be made utilizing transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J (H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., *Proc. Natl. Acad. Sci. USA,* 90:2551-255 (1993); Jakobovits et al., *Nature,* 362:255-258 (1993); Bruggemann et al., *Year in Immuno.,* 7:33 (1993)). Human antibodies can also be produced in phage display libraries (Hoogenboom et al., *J. Mol. Biol.,* 227:381 (1991); Marks et al., *J. Mol. Biol.,* 222:581 (1991)). The techniques of Cote et al. and Boerner et al. are also available for the preparation of human monoclonal antibodies (Cole et al., *Monoclonal Antibodies and Cancer Therapy, Alan R. Liss*, p. 77 (1985); Boerner et al., *J. Immunol.,* 147 (1): 86-95 (1991)).

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, CA). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) *Synthetic Peptides: A User Guide.* W.H. Freeman and Co., N.Y. (1992); Bodansky M and Trost B., Ed. (1993) *Principles of Peptide Synthesis.* Springer-Verlag Inc., NY. Alternatively, the peptide or polypeptide is independently synthesized in vivo as described above. Once isolated, these independent peptides or polypeptides may be linked to form an antibody or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry,* 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini M et al. (1992) *FEBS Lett.* 307:97-101; Clark-Lewis I et al., *J. Biol. Chem.,* 269:16075 (1994); Clark-Lewis I et al., *Biochemistry,* 30:3128 (1991); Rajarathnam K et al., *Biochemistry* 33:6623-30 (1994)).

Alternatively, unprotected peptide segments are chemically linked where the bond formed between the peptide segments as a result of the chemical ligation is an unnatural (non-peptide) bond (Schnolzer, M et al. *Science,* 256:221 (1992)). This technique has been used to synthesize analogs of protein domains as well as large amounts of relatively pure proteins with full biological activity (deLisle Milton R C et al., *Techniques in Protein Chemistry IV. Academic Press*, New York, pp. 257-267 (1992)).

Also disclosed are fragments of antibodies which have bioactivity. The polypeptide fragments can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with PD1. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. *Nucl. Acids Res.* 10:6487-500 (1982).

A variety of immunoassay formats may be used to select antibodies that selectively bind with a particular protein, variant, or fragment. For example, solid-phase ELISA immunoassays are routinely used to select antibodies selectively immunoreactive with a protein, protein variant, or fragment thereof. See Harlow and Lane. *Antibodies, A Laboratory Manual*. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., *Anal. Biochem.,* 107:220 (1980).

Also provided is an antibody reagent kit comprising containers of the monoclonal antibody or fragment thereof and one or more reagents for detecting binding of the anti-PD1 antibody or fragment thereof to the PD1 molecule. The reagents can include, for example, fluorescent tags, enzymatic tags, or other tags. The reagents can also include secondary or tertiary antibodies or reagents for enzymatic reactions, wherein the enzymatic reactions produce a product that can be visualized.

1. Homology/Identity

It is understood that one way to define any known variants and derivatives or those that might arise, of the disclosed genes and proteins herein is through defining the variants and derivatives in terms of homology to specific known sequences. For example, Table 1 sets forth a particular sequence of an PD1 heavy chain variable domain. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2:482 (1981), by the homology alignment algorithm of Needleman and Wunsch, *J. MoL Biol.* 48:443 (1970), by the search for similarity method of Pearson and Lipman, *Proc. Natl. Acad. Sci. U.S.A.* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

2. Peptides a) Protein Variants

As discussed herein there are numerous variants of the PD1 binding molecules and PD1 binding CDRs and heavy and light chain variable regions disclosed herein that are known and herein contemplated. In addition, to the known functional strain variants there are derivatives of the PD1 binding molecules and PD1 binding CDRs and heavy and light chain variable regions which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. As used herein, “insertions” refer to a change in an amino acid or nucleotide sequence resulting in the addition of one or more amino acid or nucleotide residues, respectively, as compared to the parent, often the naturally occurring, molecule. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Table 2 and are referred to as conservative substitutions.

TABLE 1

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 2

Amino Acid Substitutions

| Original Residue | Exemplary Conservative Substitutions, others are known in the art. |
|---|---|
| Ala | Ser |
| Arg | Lys; Gln |
| Asn | Gln; His |

TABLE 2-continued

Amino Acid Substitutions

| Original Residue | Exemplary Conservative Substitutions, others are known in the art. |
|---|---|
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

The replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NOs: 1 and 2. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2:482 (1981), by the homology alignment algorithm of Needleman and Wunsch, *J. MoL Biol.* 48:443 (1970), by the search for similarity method of Pearson and Lipman, *Proc. Natl. Acad. Sci. U.S.A.* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. In addition, for example, a disclosed conservative derivative of SEQ ID NOs: 1, 2, 3, 4, 5, 6, 7, 8, 9, 10, 11, 12, 13, or 14 such as the substitution of an isoleucine (I) at for a valine (V). It is understood that for this mutation all of the nucleic acid sequences that encode this particular derivative of the SEQ ID NOs: 1, 2, 3, 4, 5, 6, 7, 8, 9, 10, 11, 12, 13, or 14, are also disclosed.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH═CH— (cis and trans), —$COCH_2$—, —CH(OH) $CH_2$—, and —$CHH_2SO$— (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, Peptide Backbone Modifications (general review); Morley, *Trends Pharm Sci* (1980) pp. 463-468; Hudson, D. et al., *Int J Pept Prot Res* 14:177-185 (1979) (—$CH_2NH$—, $CH_2CH_2$—); Spatola et al. *Life Sci* 38:1243-1249 (1986) (—CH $H_2$—S); Hann *J. Chem. Soc Perkin Trans.* I 307-314 (1982) (—CH—CH—, cis and trans); Almquist et al. *J. Med. Chem.* 23:1392-1398 (1980) (—$COCH_2$—); Jennings-White et al. *Tetrahedron Lett* 23:2533 (1982) (—$COCH_2$—); Szelke et al. European Appln, EP 45665 CA (1982): 97:39405 (1982) (—CH(OH) $CH_2$—); Holladay et al. *Tetrahedron. Lett* 24:4401-4404 (1983) (—C(OH) $CH_2$—); and Hruby *Life Sci* 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations.

In one aspect, the disclosed PD1 binding molecules may further comprise a label. As used herein, a label can include a fluorescent dye, a member of a binding pair, such as biotin/streptavidin, a metal (e.g., gold), radioactive substituent, or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs-AutoFluorescent Protein-(Quantum Biotechnologies) see sgGFP, sgBFP; ALEXA FLUOR 350™; ALEXA FLUOR 430™; ALEXA FLUOR 488™; ALEXA FLUOR 532™; ALEXA FLUOR 546™; ALEXA FLUOR 568™; ALEXA FLUOR 594™; ALEXA FLUOR 633™; ALEXA FLUOR 647™; ALEXA FLUOR 660™; ALEXA FLUOR 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); CASCADE BLUE®; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.18; Cy3.5™; Cy3™; Cy5.18; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18 (5)); DIDS; Dihydorhodamine 123 (DHR); Dil (DilC18 (3)); I Dinitrophenol; DiO (DiOC18 (3)); DiR; DiR (DilC18 (7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; FURA RED™ (high pH); FURA RED™/Fluo-3; Fura-2; Fura-2/BCECF; Genacryl Brilliant Red B; Genacryl Brilliant Yellow 10GF; Genacryl Pink 3G; Genacryl Yellow 5GF; GeneBLAzer®; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (Fluoro-Gold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; Laser-Pro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; LYSOTRACKER™ Blue; LYSOTRACKER™ Blue-White; LYSOTRACKER™ Green; LYSOTRACKER™ Red; LYSOTRACKER™ Yellow; LYSOSENSOR™ Blue; LYSOSENSOR™ Green; LYSOSENSOR™ Yellow/Blue; Mag Green; Magdala Red (Phloxin B); Mag-FURA RED™; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; MITOTRACKER™ Green FM; MITOTRACKER™ Orange; MITOTRACKER™ Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; OREGON GREEN™; OREGON GREEN™ 488; OREGON GREEN™ 500; OREGON GREEN™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO™ 11; SYTO™ 12; SYTO™ 13; SYTO™ 14; SYTO™ 15; SYTO™ 16; SYTO™ 17; SYTO™ 18; SYTO™ 20; SYTO™ 21; SYTO™ 22; SYTO™ 23; SYTO™ 24; SYTO™ 25; SYTO™ 40; SYTO™ 41; SYTO™ 42; SYTO™ 43; SYTO™ 44; SYTO™ 45; SYTO™ 59; SYTO™ 60; SYTO™ 61; SYTO™ 62; SYTO™ 63; SYTO™ 64; SYTO™ 80; SYTO™ 81; SYTO™ 82; SYTO™ 83; SYTO™ 84; SYTO™ 85; SYTOX™ Blue; SYTOX™ Green; SYTOX™ Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodamineIsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; SYBR™ Green; Thiazole orange (interchelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in the apset include, but are not limited to, Tc-99m, Re-186, Ga-68, Re-188, Y-90, Sm-153, Bi-212, Cu-67, Cu-64, and Cu-62. Radiolabeling techniques such as these are routinely used in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

3. Pharmaceutical Carriers/Delivery of Pharmaceutical Products

As described above, the compositions can also be administered in vivo in a pharmaceutically acceptable carrier (also referred to herein as a pharmaceutically acceptable excipient). By "pharmaceutically acceptable" is meant a material that is not biologically or otherwise inert, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. Thus, in one aspect, disclosed herein are pharmaceutical compositions comprising any of the PD1 binding molecules disclosed herein.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and Mckenzie, *Immunolog. Reviews,* 129:57-80, (1992); and Roffler, et al., *Biochem. Pharmacol,* 42:2062-2065, (1991)). Vehicles such as “stealth” and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer’s solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer’s dextrose, dextrose and sodium chloride, lactated Ringer’s, or fixed oils. Intravenous vehicles include fluid and nutrient replenishers, electrolyte replenishers (such as those based on Ringer’s dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

4. Therapeutic Uses and Methods of Treatment

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 μg/kg to up to 100 mg/kg of body weight or more per day, depending on the factors mentioned above.

In one aspect, it is understood and herein contemplated that any of the herein disclosed PD1 binding molecules (including, but not limited to neutralizing PD1 binding molecules such as, for example, neutralizing anti-PD1 antibodies) can be used to treat, prevent, inhibit, or reduce any disease where uncontrolled cellular proliferation occurs such as cancers and metastasis. A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon cancer, rectal cancer, prostatic cancer, or pancreatic cancer.

In one aspect, disclosed herein are methods of treating, preventing, inhibiting, decreasing, ameliorating, and/or reducing a cancer and/or metastasis in a subject comprising administering to the subject any of the PD1 binding molecules disclosed herein. For example, in one aspect, disclosed herein are methods of treating, preventing, inhibiting, decreasing, ameliorating, and/or reducing a cancer and/or metastasis in a subject comprising administering to the subject an isolated PD1 binding molecule comprising a heavy chain variable domain comprising a CDR3 as set forth in SEQ ID NO: 5. Thus, for example, the methods of treating, preventing, inhibiting, decreasing, ameliorating, and/or reducing a cancer and/or metastasis in a subject can comprise administering to the subject a PD1 binding molecule comprising a heavy chain variable domain comprising a CDR3 as set forth in SEQ ID NO: 5 further comprising one or both CDRs as set forth in SEQ ID NO: 3 and SEQ ID NO: 4 (for example a binding molecule comprising a heavy chain variable domain comprises the CDRs as set forth in SEQ ID NO: 5 and SEQ ID NO: 3, SEQ ID NO: 5 and SEQ ID NO: 4, or SEQ ID NO: 3, SEQ ID NO: 4, and SEQ ID NO: 5). In one aspect, the isolated binding molecule can comprise the variable heavy chain domain as set forth in SEQ ID NO: 1.

In one aspect, disclosed herein are methods of treating, preventing, inhibiting, decreasing, ameliorating, and/or reducing a cancer and/or metastasis in a subject comprising administering to the subject an isolated PD1 binding molecule comprising a heavy chain variable domain comprising a CDR3 as set forth in SEQ ID NO: 5 can further comprise a light chain variable domain comprising one or more Complementary Determining Regions (CDR) s as set forth in SEQ ID NO: 6, SEQ ID NO: 7, or SEQ ID NO: 8 (such as, for example, a carriable light chain domain comprising the CDRs as set forth in SEQ ID NO: 6 and SEQ ID NO: 7; SEQ ID NO: 6 and SEQ ID NO: 8; SEQ ID NO: 7 and SEQ ID NO: 8; or SEQ ID NO: 6, SEQ ID NO: 7, and SEQ ID NO: 8). In one aspect, the isolated binding molecule can comprise the variable light chain domain as set forth in SEQ ID NO: 2 (for example a PD1 binding molecule comprising a variable heavy chain domain as set forth in SEQ ID NO: 1 and a variable light chain domain as set forth in SEQ ID NO: 2).

As used herein the terms "treatment," "treat," or "treating" refers to a method of reducing one or more of the effects of a disease or condition (such as, for example an inflammatory condition or a cancer) in the subject. Thus in the disclosed method, treatment can refer to a 10%, 20%, 30%, 40%, 50%, 60%, 70%, 80%, 90%, or 100% reduction in the severity of an established infection or a symptom of the infection. For example, a method for treating an inflammatory condition or cancer is considered to be a treatment if there is a 10% reduction in one or more symptoms of the condition or cancer in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the condition or disease or symptoms of the condition or disease. It is understood and herein contemplated that treatments as discussed herein can be prophylactic or therapeutic. Accordingly, in one aspect are methods of treating, reducing, ameliorating, inhibiting, or decreasing the severity of an inflammatory disease or condition in a subject comprising administering to the subject an PD1 binding molecule. Also disclosed are methods of preventing or reducing the onset of an inflammatory disease or condition in a subject comprising administering to the subject an PD1 binding molecule.

As used herein, the terms prevent, preventing, and prevention of an infection, refers to an action, for example, administration of a therapeutic agent (e.g., a composition disclosed herein), that occurs before or at about the same time a subject begins to show one or more symptoms of the infection, which inhibits or delays onset or exacerbation or delays recurrence of one or more symptoms of the infection. As used herein, references to decreasing, reducing, or inhibiting include a change of 10%, 20%, 30%, 40%, 50%, 60%, 70%, 80%, 90% or greater relative to a control level. For example, the disclosed methods are considered to be a prevention if there is about a 10% reduction in onset, exacerbation or recurrence of inflammatory condition or a disease, or symptoms of an inflammatory condition or a disease in a subject when compared to control subjects that did not receive an PD1 binding molecule for decreasing the inflammatory condition or disease.

It is understood and herein contemplated that the disclosed methods of treating, preventing, inhibiting, ameliorating, and/or reducing a cancer and/or metastasis in a subject comprising administering any of the PD1 binding molecules disclosed herein (including, but not limited to neutralizing PD1 binding molecules such as, for example, neutralizing anti-PD1 antibodies) can further comprise the administration of any anti-cancer agent that would further aid in the reduction, inhibition, treatment, and/or elimination of the cancer or metastasis (such as, for example, gemcitabine). Anti-cancer agents that can be used in the disclosed bioresponsive hydrogels or as an additional therapeutic agent in addition to the disclosed pharmaceutical compositions, and/or bioresponsive hydrogel matrixes for the methods of reducing, inhibiting, treating, ameliorating, decreasing, preventing, and/or eliminating a cancer and/or metastasis in a subject disclosed herein can comprise any anti-cancer agent known in the art, the including, but not limited to Abemaciclib, Abiraterone Acetate, Abitrexate (Methotrexate), ABRAXANE® (Paclitaxel Albumin-stabilized Nanoparticle Formulation), ABVD, ABVE, ABVE-PC, AC, AC-T, ADCETRIS® (Brentuximab Vedotin), ADE, Ado-Trastuzumab Emtansine, Adriamycin (Doxorubicin Hydrochloride), Afatinib Dimaleate, AFINITOR® (Everolimus), AKYNZEO® (Netupitant and Palonosetron Hydrochloride), ALDARA® (Imiquimod), Aldesleukin, ALECENSA® (Alectinib), Alectinib, Alemtuzumab, Alimta (Pemetrexed Disodium), ALIQOPA® (Copanlisib Hydrochloride), ALKERAN® for Injection (Melphalan Hydrochloride), ALKERAN® Tablets (Melphalan), ALOXI® (Palonosetron Hydrochloride), ALUNBRIG® (Brigatinib), Ambochlorin (Chlorambucil), Amboclorin Chlorambucil), Amifostine, Aminolevulinic Acid, Anastrozole, Aprepitant, AREDIA® (Pamidronate Disodium), ARIMIDEX® (Anastrozole), AROMASIN® (Exemestane), ARRANON® (Nelarabine), Arsenic Trioxide, ARZERRA® (Ofatumumab), Asparaginase *Erwinia chrysanthemi*, Atezolizumab, AVASTIN® (Bevacizumab), Avelumab, Axitinib, Azacitidine, BAVENCIO® (Avelumab), BEACOPP, Becenum (Carmustine), BELEODAQ® (Belinostat), Belinostat, Bendamustine Hydrochloride, BEP, BESPONSA® (Inotuzumab Ozogamicin), Bevacizumab, Bexarotene, BEXXAR® (Tositumomab and Iodine I 131 Tositumomab), Bicalutamide, BiCNU (Carmustine), Bleomycin, Blinatumomab, BLINCYTO® (Blinatumomab), Bortezomib, BOSULIF® (Bosutinib), Bosutinib, Brentuximab Vedotin, Brigatinib, BuMel, Busulfan, BUSULFEX® (Busulfan), Cabazitaxel, CABOMETYX® (Cabozantinib-S-Malate), Cabozantinib-S-Malate, CAF, CAMPATH® (Alemtuzumab), CAMPTOSAR®, (Irinotecan Hydrochloride), Capecitabine, CAPOX, CARAC® (Fluorouracil—Topical), Carboplatin, CARBOPLATIN-TAXOL, Carfilzomib, CARMUBRIS® (Carmustine), Carmustine, Carmustine Implant, CASODEX® (Bicalutamide), CEM, Ceritinib, CERUBIDINE® (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, CLAFEN® (Cyclophosphamide), Clofarabine, Clofarex (Clofarabine), CLOLAR® (Clofarabine), CMF, Cobimetinib, COMETRIQ™ (Cabozantinib-S-Malate), Copanlisib Hydrochloride, COPDAC, COPP, COPP-ABV, COSMEGEN® (Dactinomycin), COTELLIC® (Cobimetinib), Crizotinib, CVP, Cyclophosphamide, Cyfos (Ifosfamide), CYRAMZA® (Ramucirumab), Cytarabine, Cytarabine Liposome, CYTOSAR®-U (Cytarabine), CYTOXAN® (Cyclophosphamide), Dabrafenib, Dacarbazine, DACOGEN® (Decitabine), Dactinomycin, Daratumumab, DARZALEX® (Daratumumab), Dasatinib, Daunorubicin Hydrochloride, Daunorubicin Hydrochloride and Cytarabine Liposome, Decitabine, Defibrotide Sodium, DEFITELIO® (Defibrotide Sodium), Degarelix, Denileukin Diftitox, Denosumab, DEPOCYT® (Cytarabine Liposome), Dexamethasone, Dexrazoxane Hydrochloride, Dinutuximab, Docetaxel, DOXIL® (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, EFUDEX® (Fluorouracil—Topical), ELITEK® (Rasburicase), ELLENCE® (Epirubicin Hydrochloride), Elotuzumab, ELOXATIN® (Oxaliplatin), Eltrombopag Olamine, EMEND® (Aprepitant), EMPLICITI® (Elotuzumab), Enasidenib Mesylate, Enzalutamide, Epirubicin Hydrochloride, EPOCH, ERBITUX® (Cetuximab), Eribulin Mesylate, ERIVEDGE (Vismodegib), Erlotinib Hydrochloride, ERWINAZE® (Asparaginase *Erwinia chrysanthemi*), ETHYOL® (Amifostine), ETOPOPHOS® (Etoposide Phosphate), Etoposide, Etoposide Phosphate, EVACET® (Doxorubicin Hydrochloride Liposome), Everolimus, EVISTA®, (Raloxifene Hydrochloride), EVOMELA® (Melphalan Hydrochloride), Exemestane, 5-FU (Fluorouracil Injection), 5-FU (Fluorouracil—Topical), FARESTON® (Toremifene), FARYDAK® (Panobinostat), FASLODEX® (Fulvestrant), FEC, FEMARA® (Letrozole), Filgrastim, FLUDARA® (Fludarabine Phosphate), Fludarabine Phosphate, FLUOROPLEX® (Fluorouracil-Topical), Fluorouracil Injection, Fluorouracil—Topical, Flutamide, FOLEX® (Methotrexate), FOLEX® PFS (Methotrexate), FOLFIRI, FOLFIRI-BEVACIZUMAB, FOLFIRI-CETUXIMAB, FOLFIRINOX, FOLFOX, FOLOTYN® (Pralatrexate), FU-LV, Fulvestrant, GARDASIL® (Recombinant HPV Quadrivalent Vaccine), GARDASIL® 9 (Recombinant HPV Nonavalent Vaccine), GAZYVA® (Obinutuzumab), Gefitinib, Gemcitabine Hydrochloride, GEMCITABINE-CISPLATIN, GEMCITABINE-OXALIPLATIN, Gemtuzumab Ozogamicin, GEMZAR® (Gemcitabine Hydrochloride), GILOTRIF® (Afatinib Dimaleate), GLEEVEC® (Imatinib Mesylate), GLIADEL® (Carmustine Implant), GLIADEL® wafer (Carmustine Implant), Glucarpidase, Goserelin Acetate, HALAVEN® (Eribulin Mesylate), HEMANGEOL® (Propranolol Hydrochloride), HERCEPTIN® (Trastuzumab), HPV Bivalent Vaccine, Recombinant, HPV Nonavalent Vaccine, Recombinant, HPV Quadrivalent Vaccine, Recombinant, HYCAMTIN® (Topotecan Hydrochloride), HYDREA® (Hydroxyurea), Hydroxyurea, Hyper-CVAD, IBRANCE® (Palbociclib), Ibritumomab Tiuxetan, Ibrutinib, ICE, ICLUSIG® (Ponatinib Hydrochloride), IDAMYCIN® (Idarubicin Hydrochloride), Idarubicin Hydrochloride, Idelalisib, IDHIFA® (Enasidenib Mesylate), Ifex (Ifosfamide), Ifosfamide, Ifosfamidum (Ifosfamide), IL-2 (Aldesleukin), Imatinib Mesylate, IMBRUVICA® (Ibrutinib), IMFINZI® (Durvalumab), Imiquimod, IMLYGIC® (Talimogene Laherparepvec), INLYTA® (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, IRESSA® (Gefitinib), Irinotecan Hydrochloride, Irinotecan Hydrochloride Liposome, ISTODAX® (Romidepsin), Ixabepilone, Ixazomib Citrate, IXEMPRA® (Ixabepilone), JAKAFI® (Ruxolitinib Phosphate), JEB, JEVTANA® (Cabazitaxel), KADCYLA® (Ado-Trastuzumab Emtansine), Keoxifene (Raloxifene Hydrochloride), KEPIVANCE® (Palifermin), KEYTRUDA® (Pembrolizumab), KISQALI® (Ribociclib), KYMRIAH® (Tisagenlecleucel), KYPROLIS® (Carfilzomib), Lanreotide Acetate, Lapatinib Ditosylate, LARTRUVO™ (Olaratumab), Lenalidomide, Lenvatinib Mesylate, LENVIMA® (Lenvatinib Mesylate), Letrozole, Leucovorin Calcium, LEUKERAN® (Chlorambucil), Leuprolide Acetate, LEUSTATIN® (Cladribine), LEVULAN® (Aminolevulinic Acid), Linfolizin (Chlorambucil), LIPODOX® (Doxorubicin Hydrochloride Liposome), Lomustine, LONSURF® (Trifluridine and Tipiracil Hydrochloride), LUPRON® (Leuprolide Acetate), LUPRON® Depot (Leuprolide Acetate), LUPRON® Depot-Ped (Leuprolide Acetate), LYNPARZA® (Olaparib), MARQIBO® (Vincristine Sulfate Liposome), MATULANE® (Procarbazine Hydrochloride), Mechlorethamine Hydrochloride, Megestrol Acetate, MEKINIST® (Trametinib), Melphalan, Melphalan Hydrochloride, Mercaptopurine, Mesna, MESNEX® (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, MITOZYTREX™ (Mitomycin C), MOPP, MOZOBIL® (Plerixafor), MUSTARGEN® (Mechlorethamine Hydrochloride), MUTAMYCIN® (Mitomycin C), MYLERAN® (Busulfan), Mylosar (Azacitidine), MYLOTARG™ (Gemtuzumab Ozogamicin), Nanoparticle Paclitaxel (Paclitaxel Albumin-stabilized Nanoparticle Formulation), NAVELBINE® (Vinorelbine Tartrate), Necitumumab, Nelarabine, Neosar (Cyclophosphamide), Neratinib Maleate, NERLYNX® (Neratinib Maleate), Netupitant and Palonosetron Hydrochloride, NEULASTA® (Pegfilgrastim), NEUPOGEN® (Filgrastim), NEXAVAR® (Sorafenib Tosylate), NILANDRON® (Nilutamide), Nilotinib, Nilutamide, NINLARO® (Ixazomib Citrate), Niraparib Tosylate Monohydrate, Nivolumab, NOLVADEX® (Tamoxifen Citrate), NPLATE® (Romiplostim), Obinutuzumab, ODOMZO® (Sonidegib), OEPA, Ofatumumab, OFF, Olaparib, Olaratumab, Omacetaxine Mepesuccinate, ONCASPAR® (Pegaspargase), Ondansetron Hydrochloride, ONIVYDE® (Irinotecan Hydrochloride Liposome), ONTAK® (Denileukin Diftitox), OPDIVO® (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), PARAPLATIN® (Carboplatin), Pazopanib Hydrochloride, PCV, PEB, Pegaspargase, Pegfilgrastim, Peginterferon Alfa-2b, PEGINTRON® (Peginterferon Alfa-2b), Pembrolizumab, Pemetrexed Disodium, PERJETA® (Pertuzumab), Pertuzumab, PLATINOL® (Cisplatin), PLATINOL®-AQ (Cisplatin), Plerixafor, Pomalidomide, POMALYST® (Pomalidomide), Ponatinib Hydrochloride, PORTRAZZA® (Necitumumab), Pralatrexate, Prednisone, Procarbazine Hydrochloride, PROLEUKIN® (Aldesleukin), PROLIA® (Denosumab), PROMACTA® (Eltrombopag Olamine), Propranolol Hydrochloride, PROVENGE® (Sipuleucel-T), PURINETHOL® (Mercaptopurine), PURIXAN® (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, RELISTOR® (Methylnaltrexone Bromide), R-EPOCH, REVLIMID® (Lenalidomide), RHEUMATREX® (Methotrexate), Ribociclib, R-ICE, RITUXAN® (Rituximab), RITUXAN HYCELA® (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), RUBRACA® (Rucaparib Camsylate), Rucaparib Camsylate, Ruxolitinib Phosphate, RYDAPT® (Midostaurin), SCLEROSOL® Intrapleural Aerosol (Talc), Siltuximab, Sipuleucel-T, SOMATULINE® Depot (Lanreotide Acetate), Sonidegib, Sorafenib Tosylate, SPRYCEL® (Dasatinib), STANFORD V, Sterile Talc Powder (Talc), STERITALC® (Talc), STIVARGA® (Regorafenib), Sunitinib Malate, SUTENT® (Sunitinib Malate), SYLATRON™ (Peginterferon Alfa-2b), SYLVANT® (Siltuximab), SYNRIBO® (Omacetaxine Mepesuccinate), TABLOID® (Thioguanine), TAC, TAFINLAR® (Dabrafenib), TAGRISSO® (Osimertinib), Talc, Talimogene Laherparepvec, Tamoxifen Citrate, Tarabine PFS (Cytarabine), TARCEVA® (Erlotinib Hydrochloride), TARGRETIN® (Bexarotene), TASIGNA® (Nilotinib), TAXOL® (Paclitaxel), TAXOTERE® (Docetaxel), TECENTRIQ® (Atezolizumab), TEMODAR® (Temozolomide), Temozolomide, Temsirolimus, Thalidomide, THALOMID® (Thalidomide), Thioguanine, Thiotepa, Tisagenlecleucel, TOLAK® (Fluorouracil—Topical), Topotecan Hydrochloride, Toremifene, TORISEL® (Temsirolimus), Tositumomab and Iodine I 131 Tositumomab, TOTECT® (Dexrazoxane Hydrochloride), TPF, Trabectedin, Trametinib, Trastuzumab, TREANDA® (Bendamustine Hydrochloride), Trifluridine and Tipiracil Hydrochloride, TRISENOX® (Arsenic Trioxide), TYKERB® (Lapatinib Ditosylate), UNITUXIN® (Dinutuximab), Uridine Triacetate, VAC, Vandetanib, VAMP, VARUBI® (Rolapitant Hydrochloride), VECTIBIX® (Panitumumab), VeIP, VELBAN® (Vinblastine Sulfate), VELCADE® (Bortezomib), Velsar (Vinblastine Sulfate), Vemurafenib, VENCLEXTA® (Venetoclax), Venetoclax, VERZENIO® (Abemaciclib), VIADUR® (Leuprolide Acetate), VIDAZA® (Azacitidine), Vinblastine Sulfate, VINCASAR PFS® (Vincristine Sulfate), Vincristine Sulfate, Vincristine Sulfate Liposome, Vinorelbine Tartrate, VIP, Vismodegib, VISTOGARD® (Uridine Triacetate), VORAXAZE® (Glucarpidase), Vorinostat, VOTRIENT® (Pazopanib Hydrochloride), VYXEOS® (Daunorubicin Hydrochloride and Cytarabine Liposome), Wellcovorin (Leucovorin Calcium), XALKORI® (Crizotinib), XELODA® (Capecitabine), XELIRI, XELOX, XGEVA® (Denosumab), XOFIGO® (Radium 223 Dichloride), XTANDI® (Enzalutamide), YERVOY® (Ipilimumab), YONDELIS® (Trabectedin), ZALTRAP® (Ziv-Aflibercept), ZARXIO® (Filgrastim), Zejula (Niraparib Tosylate Monohydrate), ZELBORAF® (Vemurafenib), ZEVALIN® (Ibritumomab Tiuxetan), ZINECARD® (Dexrazoxane Hydrochloride), Ziv-Aflibercept, ZOFRAN® (Ondansetron Hydrochloride), ZOLADEX® (Goserelin Acetate), Zoledronic Acid, ZOLINZA® (Vorinostat), ZOMETA® (Zoledronic Acid), ZYDELIG® (Idelalisib), ZYKADIA® (Ceritinib), and/or ZYTIGA® (Abiraterone Acetate).

C. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Despite the dismaying outcome of ovarian cancer patients, immune cells in the ovarian carcinoma microenvironment spontaneously exert clinically relevant pressure against malignant progression. Shown herein are a characteristic Th1 signature, multiple immunosuppressive mechanisms and T cells reacting against ovarian cancer antigens, further supporting that many ovarian cancers are truly immunogenic. However, checkpoint inhibitors show no better than 15% effectiveness in ovarian cancer patients. This is probably because T cells do not operate in isolation; ovarian tumors infiltrated by CD8 T cells often contain many $CD19^+$ B cells. Although regulatory B cells have been identified in different malignancies, recent studies demonstrate that only ovarian tumors containing both $CD8^+$ and $CD20^+$ lymphocytes identify patients with better outcomes. Overall, the role of B cells in ovarian cancer and their crosstalk with T cells remains poorly understood. Herein the protective role that B cells is described, through the production of antibodies and by influencing T cell activity, can exert against malignant progression.

Within tumor beds, T and B cells often co-localize in aggregates of different mass. In some specimens, these lymphocyte subsets interact to form highly organized structures resembling lymph nodes, termed tertiary lymphoid structures (TLS). TLS are characterized by discrete T-cell zone containing CD4 and CD8 T cells, and high endothelial venules (HEV), which are adjacent to prominent B-cell follicles, including germinal centers with interdigitating networks of follicular DCs. These characteristics are reminiscent of TLS developing in noncancerous conditions such as autoimmunity and transplantation, where TLS are associated with tissue damage. Critically, the presence of TLS is associated with better outcomes in more than 10 different types of cancer, suggesting that optimal anti-tumor immunity requires a mix of T cell and antibody-mediated responses. Recent studies in ovarian cancer patients indicate that favorable CD8 TIL responses are associated with the presence of TLS structures, which are present in 15-20% of ovarian carcinoma specimens.

Although the evidence supporting a protective role for TLS in at least breast and ovarian cancer is overwhelming, the role of B cells in different cancers remains controversial. Thus, B cells appear to play a tumor-promoting role in pancreatic cancer, while inflammation-induced $IgA^+$ cells counteracts anti-liver cancer immunity. Herein is dissected the relative contribution of B cells producing different classes of Igs, which have different roles in protective immunity. Equally important, most antibodies produced at tumor beds recognize intracellular proteins. However, antibodies that recognize proteins on the cell membrane or tumor-promoting cytokines have been also identified in cancer patients. These humoral responses are associated with better outcomes and can be boosted by checkpoint inhibitors or vaccines. Even antibodies that recognize intracellular tumor antigens can still promote tumor cell killing through ADCC and/or complement activation. Besides understanding how TLS can be assembled at metastatic or irresectable tumor beds, herein protective antibodies spontaneously produced in ovarian cancer patients which could be used for novel anti-cancer interventions are characterized.

Serous ovarian carcinomas originate from the fimbriated epithelium at the end of the Fallopian tube. Although the role of secretory IgA is best understood in the gut, transcytosis of polymeric IgA (transcellular transport across the interior of epithelial cells) also operates in the cervix and fallopian tubes. Accordingly, herein is shown that >50% of serous ovarian carcinomas retain expression of PIGR, the Fc receptor that captures extracellular polymeric IgA to be actively transported through the cell to external secretions. These tumor cells are coated with IgA produced at tumor beds, and that. This is important because, unlike IgG, IgA can neutralize and drive the excretion of pathogens intracellularly at endosomal compartments. This opens the tantalizing possibility of targeting intracellular tumor-promoting molecules in $PIGR^+$ malignancies using IgA. Thus, receptor tyrosine kinase signaling occurs also at endosomes, where mutation-specific IgAs can interfere with MAPK or PI3K. In fact, AKT is actively inhibited by phosphatases specifically at endosomal compartments, while up to 15% of total K-Ras is found in endosomes, independent of its activation state. Thus, IgAs that recognize oncogenic intracellular molecules is a priority. Additionally, IgA enhances the sensitivity of tumor cells to T cell mediated killing.

Example 1: Human Ovarian Cancers Contain Plasmablasts and Plasma Cells

As aforementioned, 15-20% of ovarian carcinomas contain TLS, which are associated with better prognosis. Here, 5 fresh human stage III/IV serous ovarian carcinomas were dissociated and analyzed for the proportions of $CD45^+CD3^+CD4^+CXCR5^+ICOS^+PD1^{high}BCL6^+$ T follicular helper (TFH) cells and $CD45^+C19^+CD20^-CD3^-CD138^-CD38^+$ plasmoblasts. As illustrated by FIG. 1A, a distinctive population of plasmoblasts (>0.2% of hematopoietic cells) was found in 3 out of 5 samples. Those trend to correspond to tumors with higher proportions of TFH cells (r=0.99; FIG. 1B). These results indicate that antibody-producing plasmoblasts are commonly infiltrating ovarian cancers.

Example 2: IgA-Producing B Cells Dominate the Humoral Response in Human Serous Ovarian Carcinomas To determine what antibodies are primarily generated by B cells at ovarian cancer beds, 15 additional fresh human stage III/IV serous ovarian carcinomas were dissociated and stained live individual cells for the presence of all possible antibodies. As shown in FIG. 2, unexpectedly, it was found that the majority of tumor-associated B cells produce IgA, followed by IgG and IgM. Interestingly, it was also found that a significant fraction of CD45-cells (primarily tumor cells in the dissociation protocol) are also coated by IgA. Accordingly, expression of the polymeric IgA receptor (PIGR) was confirmed in OVCAR3 and SKOV3 ovarian cancer cell lines by Western blot. To elucidate the proportion of human ovarian cancers with tumor cells coated by IgA, next 97 serous advanced ovarian carcinomas and 4 control healthy ovaries were stained for PIGR and IgA expression. As shown in FIG. 3, >50% of human tumors expressed PIGR and were coated by IgA, opening new avenues for immunotherapeutic interventions in ovarian cancer patients. Most importantly, patients with PIGR/IgA$^+$ showed a significant survival benefit, indicating that IgA produced at tumor beds can have a protective effect against ovarian cancer progression. Similar results were also observed in patients with plasma cells/plasmablasts. In addition, patients with more B cells in the tumor microenvironment (TME) also show accumulation of CD4 and CD8 T cells.

Example 3: Optimization of a Protocol for Immortalizing Ovarian Cancer-Derived B Cells To characterize the specificities of the antibodies produced by B cells at tumor beds, a protocol for the separation of CD19$^+$ B cells from solid ovarian tumors and EBV-based immortalization was optimized (summary and an example shown in FIG. 4). A combination of CD40 agonists and IL-21 resulted in activating conditions with the highest immortalization rate for magnetically immune-purified B cells (80% so far). B cells sorted from 8 ovarian tumors (4 with confirmed TLS and 4 where TLS were not identified in the sections analyzed) have already been immortalized. Of note, although the majority of B cells in the TME are coated with IgA, immortalized tumor-derived B cells also produced IgG at titers similar to IgA, indicating that B cell activation can select IgG producers. Nevertheless, the method also allow IgA titers recovered from cultured polyclonal B cells in the 0.7-37 μg/mL range, along with IgG, to identify tumor reactivity.

Example 4: Define the Specificities of IgA and IgG Produced at TLS$^+$ Versus TLS-Human Ovarian Cancer Beds The optimized protocol can be used to separate, activate and immortalize B cells from freshly dissociated advanced serous ovarian carcinomas from patients with TLS or from TLS tumors. Freshly resected stage III/IV ovarian carcinomas from naïve patients are routinely obtained through an IRB approved protocol. Tissues are mechanically dissociated and cryopreserved, with viabilities ranging from 20-75% when aliquots are thawed. Viable immune cells from human ovarian cancers were used for a variety of functional assays in the past. For this study, B cells can be purified from every dissociated ovarian carcinoma arriving in the lab. B cells can be immediately activated with CD40 agonists plus IL-21 or commercially available B cell expansion kits (i.e., from R&D) and immortalized using EBV. Immortalized B cells can be routinely cryopreserved to generate a library of tumor-derived B cells from >50 specimens, including other human malignancies different from ovarian cancer. In parallel, OCT blocks can be generated for histological analysis and identification of TLS through IHC analysis, using CD19 and CD3 antibodies. Before cryopreservation, IgA and IgG can be purified from immortalized B cells with resins that selectively capture IgG and, in parallel, IgA (both from Thermo). At least 8 ovarian carcinomas with conglomerates of B and T cells compatible with TLS can be identified through IHC and an equal number of samples where TLS are not identified in at least 2 sections. IgG and IgA can be independently quantified (Sigma) and sent to CDI Laboratories for determination of their specificities using HuProt proteome arrays, which contain >80% of the human proteome. A summary of the procedure is summarized in FIG. 5.

Example 5: IgA Transcytosis and Tumor Antigen Recognition Govern Antitumor Immunity in Ovarian Cancer Ovarian cancer is an immunogenic disease in which the pre-established immunoreactive landscape determines the patient's outcome. However, as monotherapies immune checkpoint inhibitors that augment T-cell activity have only very modest response rates in patients with advanced disease. Recent studies have suggested that plasma cell and memory B-cell infiltrates, including those in Tertiary Lymphoid Structures (TLS7), are associated with T-cell cytolytic activity at ovarian cancer beds, resulting in superior outcome. While these studies suggest that humoral responses can potentiate T-cell immune surveillance, the roles of different antibody isotypes in malignant progression are controversial.

Figures 6A, 6B:
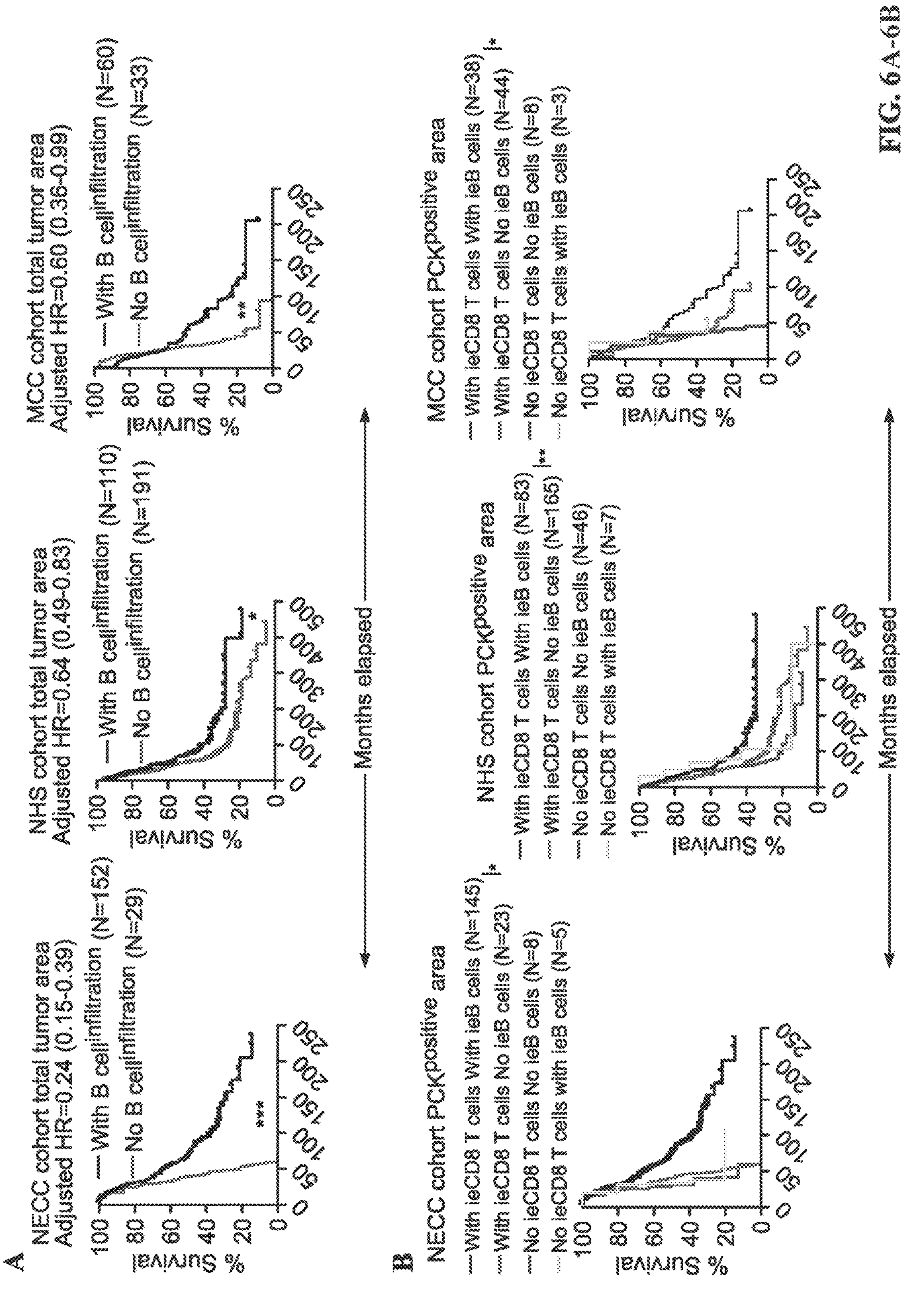

To characterize the role of B-cells in ovarian cancer, we first stained a panel of 575 annotated HGSOCs from three independent cohorts with T- and B-cell markers. Confirming the overall protective role of humoral responses in ovarian cancer, CD19+ B-cell infiltrates were identified in ~50% of tumors and these connote a superior outcome in all three cohorts (FIG. 6A), and positively correlate with T-cell infiltrates (FIG. 7A). Notably, intra-epithelial T-cells only predict improved survival when B-cells co-infiltrate tumor islets (FIG. 8A and FIG. 6B). Similar positive associations between CD19 expression and improved survival were manifest in TCGA datasets (FIG. 9), and were associated with increased production of anti-tumor TNF-α and IL-18, and with downregulation of immunoregulatory IL-10. Further, spatial analysis of immunostained HGSOCs revealed that tumor-infiltrating T-cells significantly clustered in areas of B-cell and plasma cell infiltration (FIG. 8C, left and FIG. 10), over a wide range of distances (FIG. 8C, right).

Figure 8D:
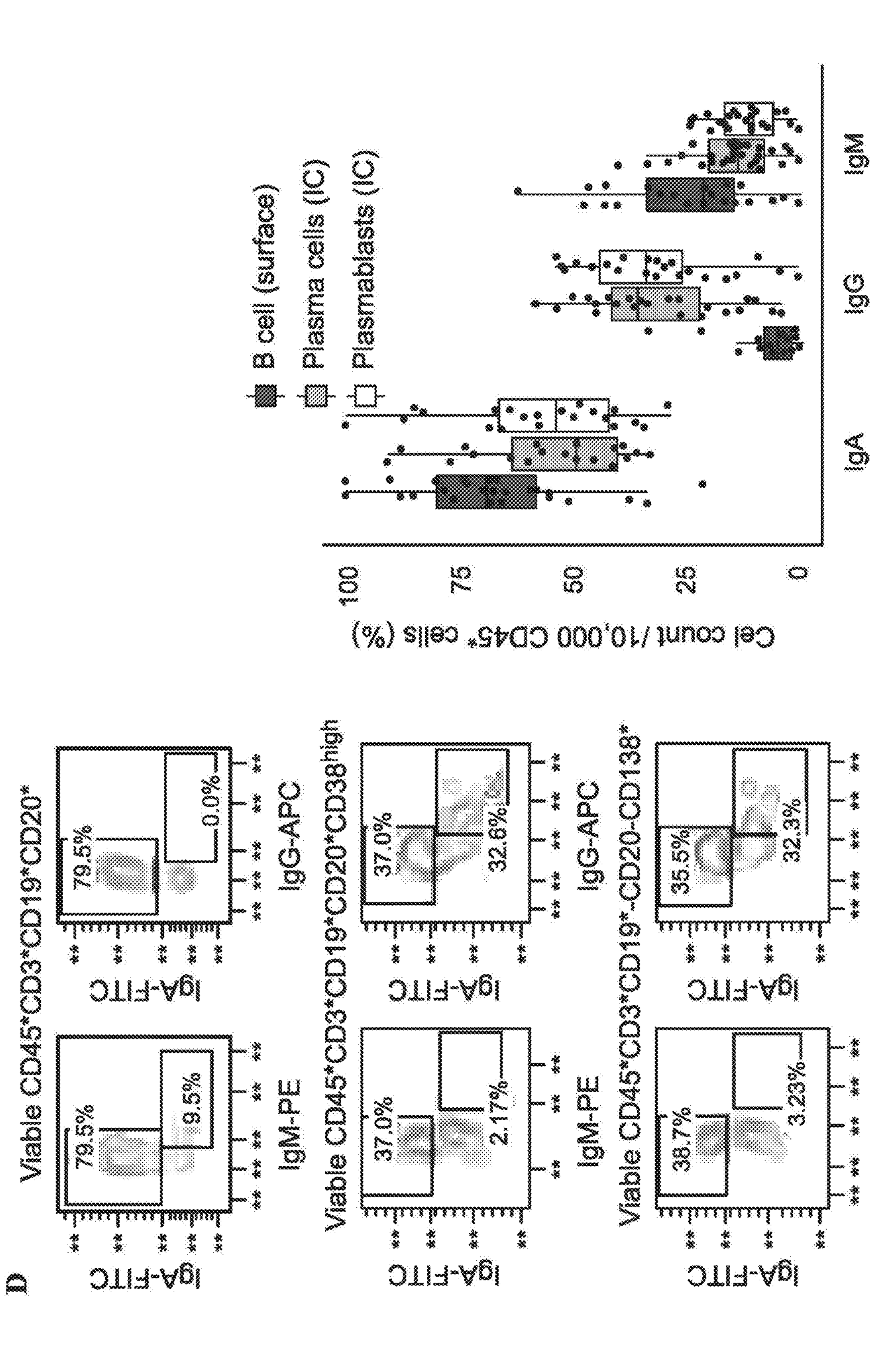
Figure 8E:
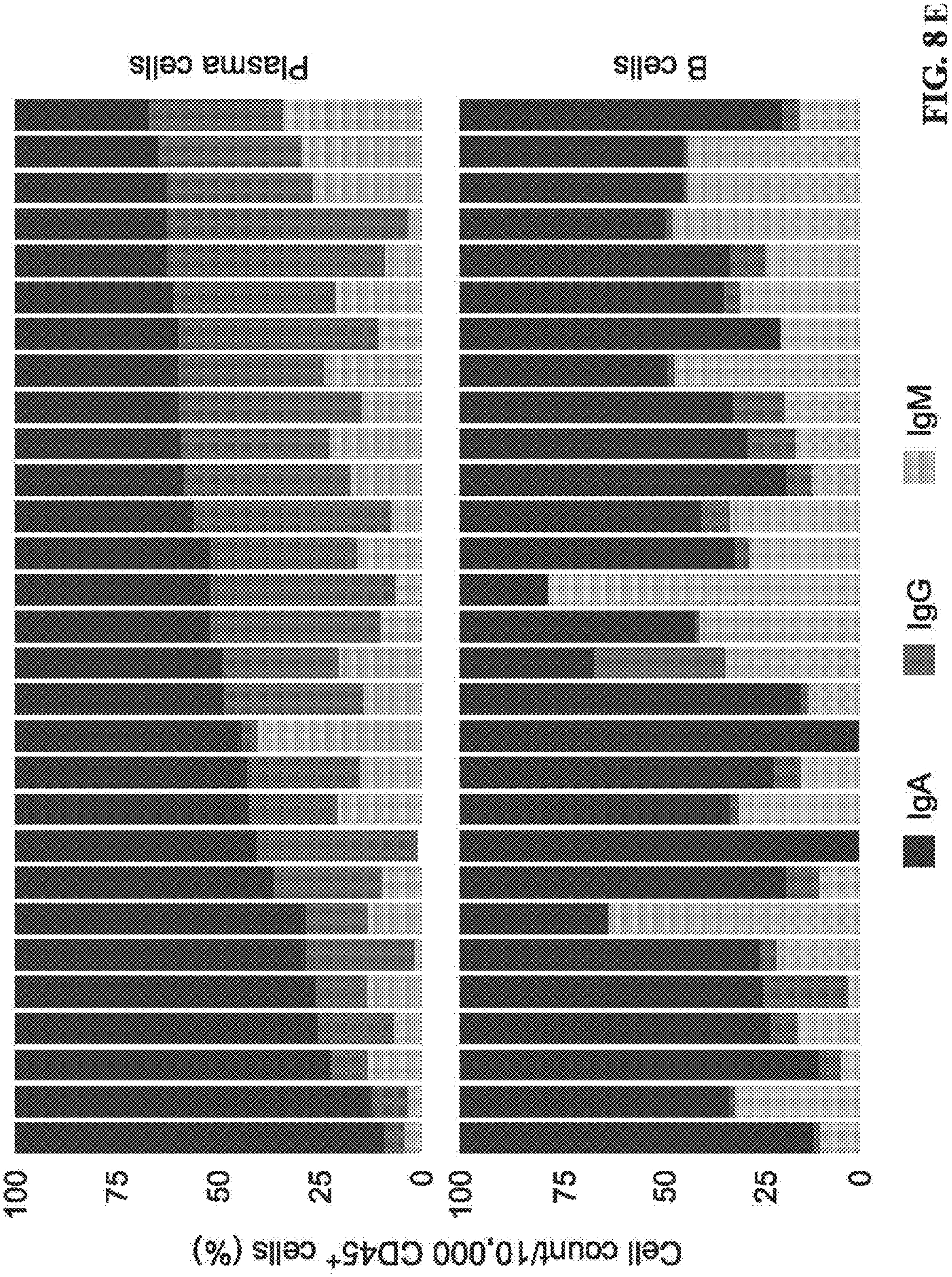

To characterize the isotypes produced by these B-lymphocytes, viable single-cell suspensions from 29 freshly dissociated HGSOCs were analyzed. Intracellular staining of plasma cells and CD19+CD20−CD38highCD27+ cells (defined as plasmablasts;) revealed dominant production of class-switched IgA, followed by IgG, which is consistent with TCGA mRNA expression (FIG. 8D-8E and FIGS. 9, 11 & 12) and surface staining of B-cells (FIG. 8D-8E and FIG. 11A).

CD138+ plasma cell infiltrates were associated with superior outcome in all three cohorts (FIG. 8F), were identified in 80% of dissociated tumors in >1% of total leukocytes, and also correlated with intratumoral T-cells (FIGS. 7B & 7C).

Figures 6C, 6D:
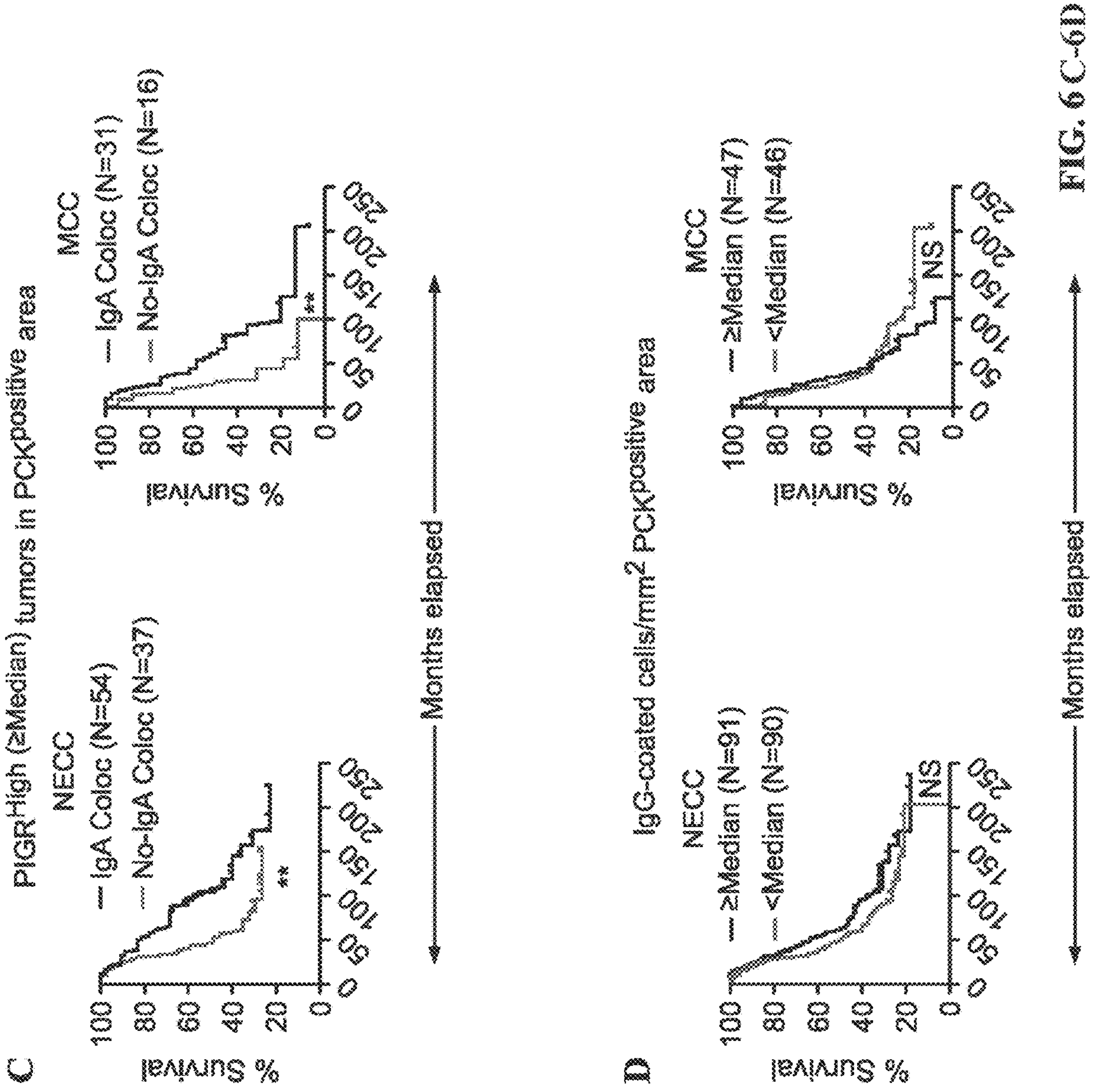
Figures 8F, 8G, 8H:
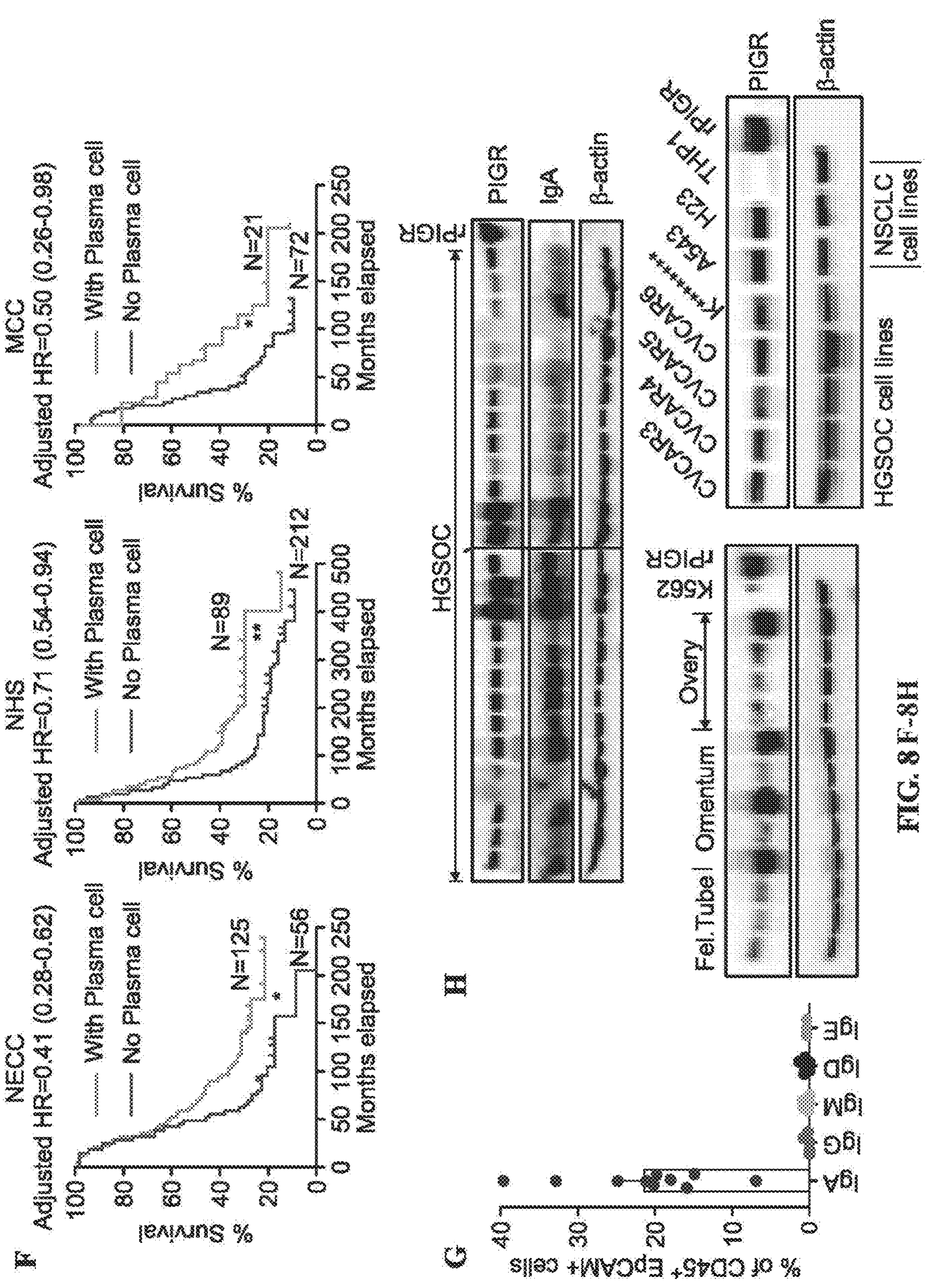
Figure 8I:
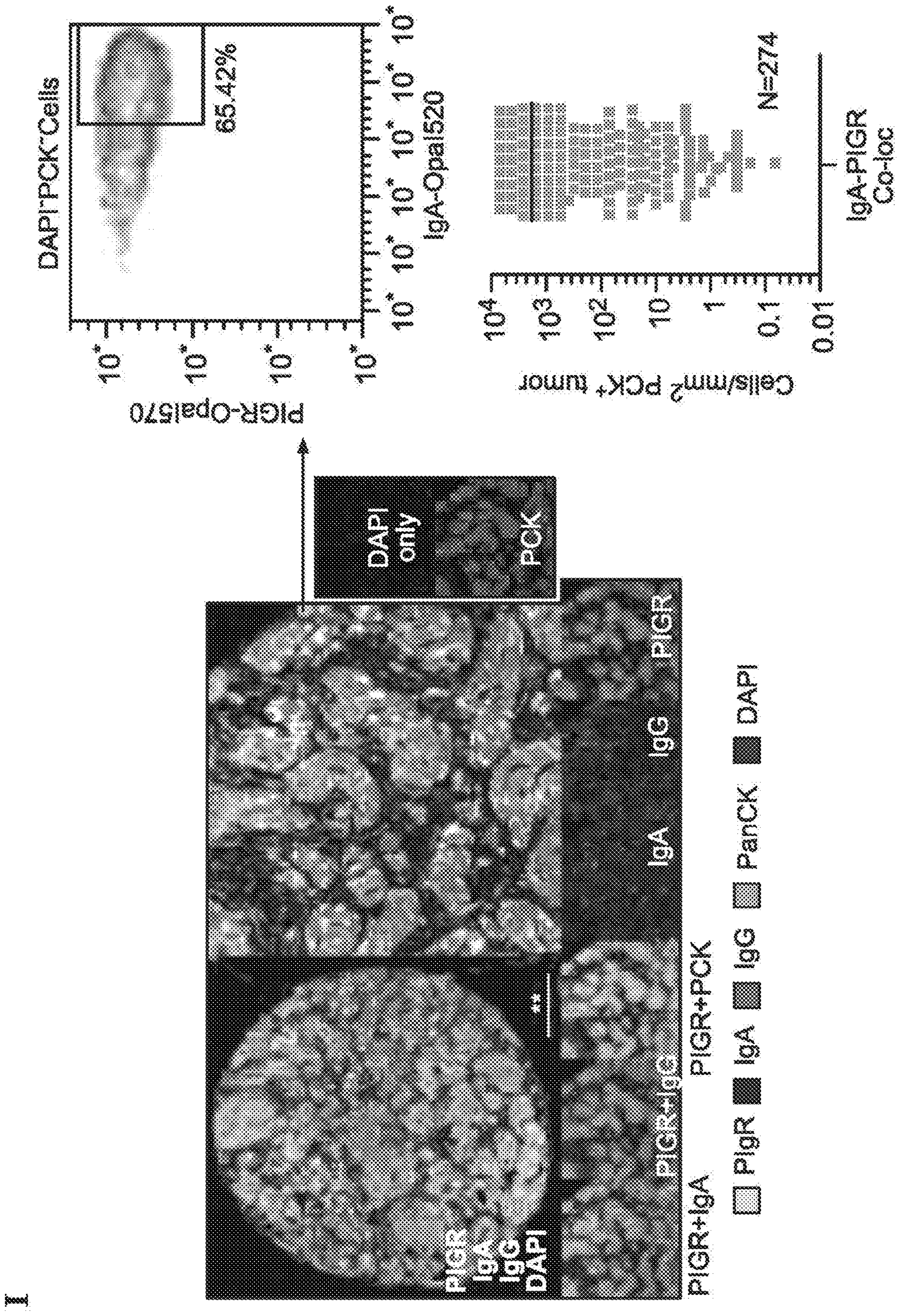
Figure 8J:
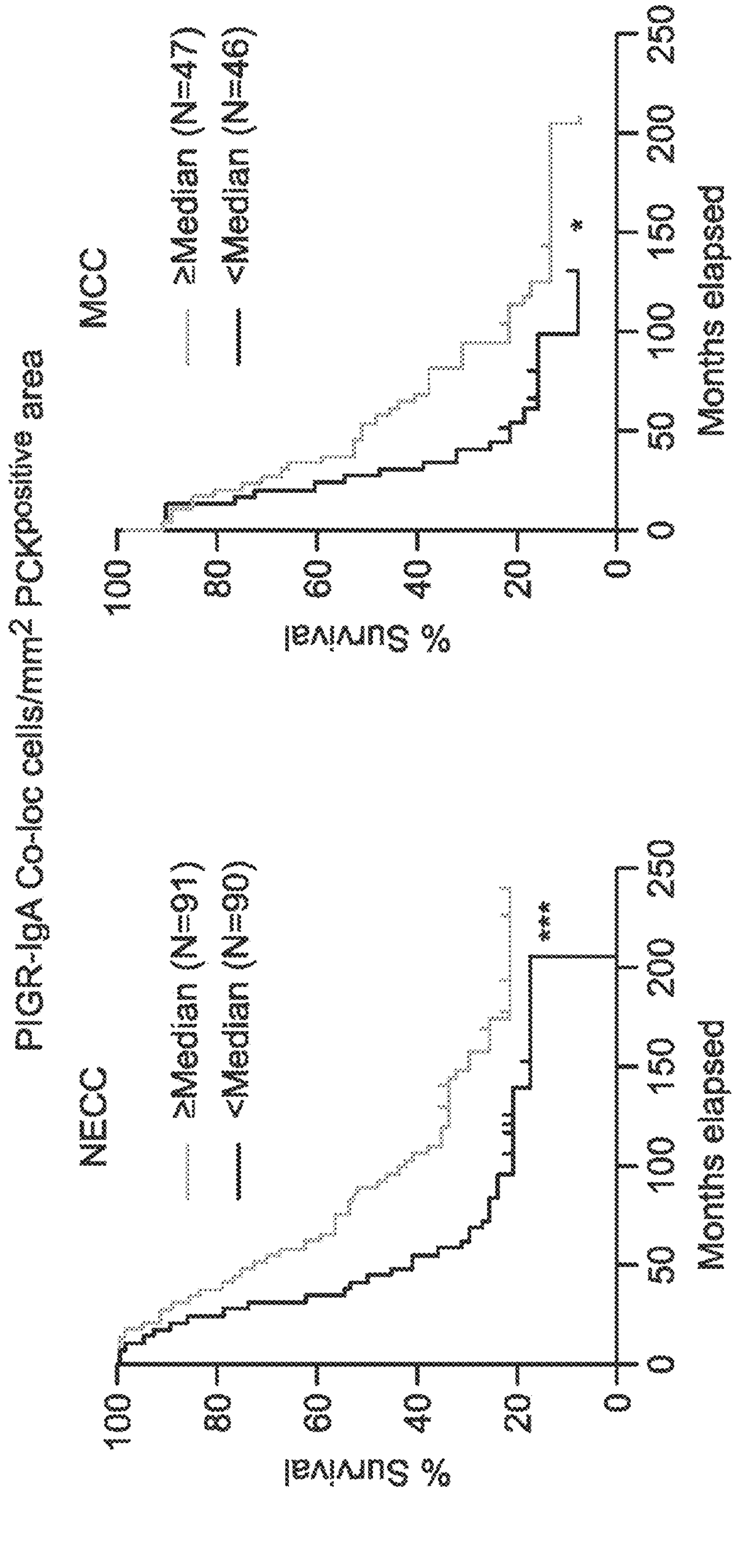
Figures 13A, 13B:
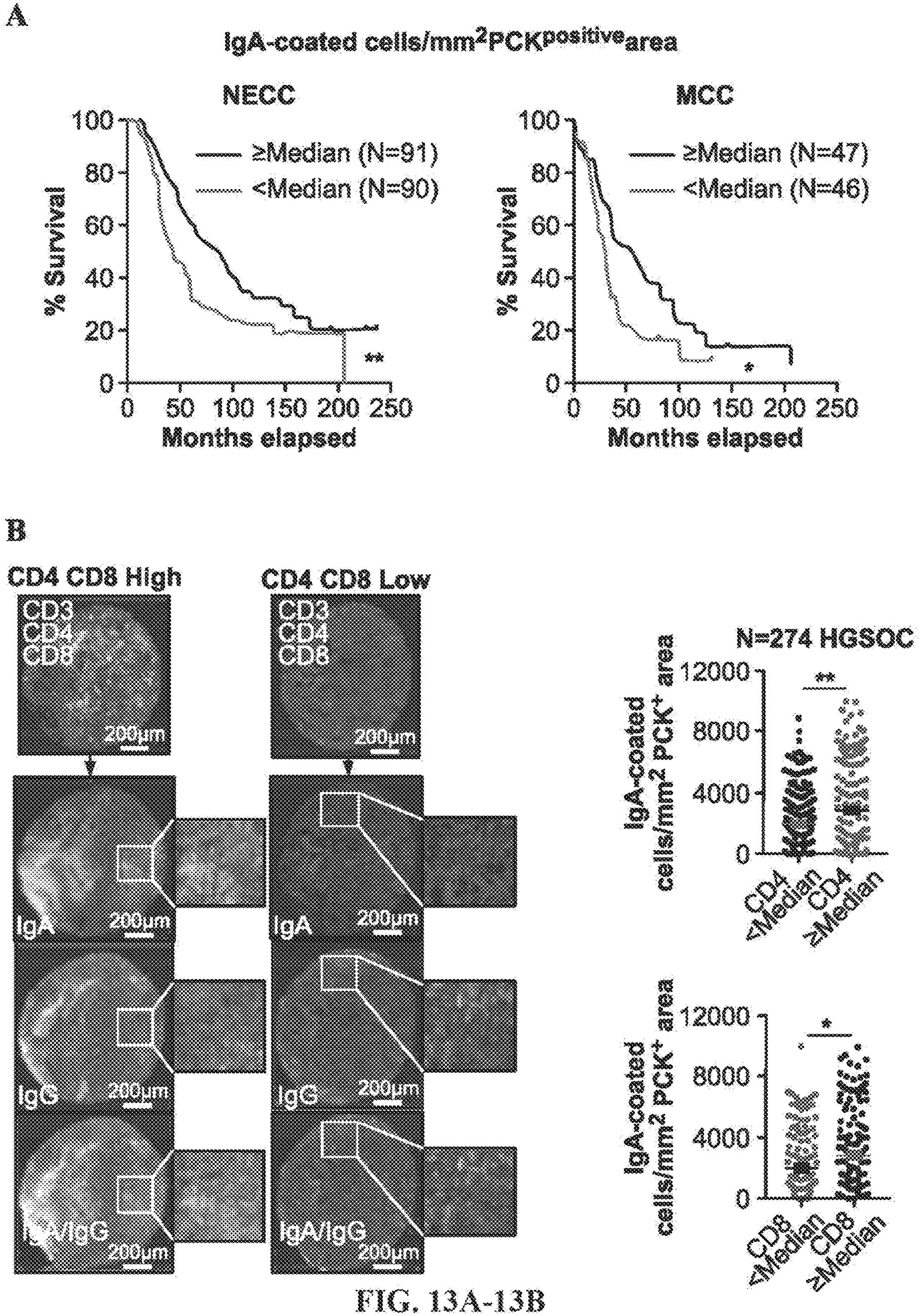

Unexpectedly, CD45-EpCAM+ tumor cells were also coated by IgA in all dissociated HGSOCs evaluated (FIG. 8G). Accordingly, we found universal expression of the polymeric IgA Receptor (pIgR) in HGSOC, as well as in tumor-free Fallopian tube, ovarian and omental tissue (but not in THP1 or K562 leukemia cells; FIG. 8H). Consequently, IgA and pIgR co-localize at tumor beds within the cytokeratin+ tumor islets in 274 HGSOCs analyzed (FIG. 8I), and IgA:pIgR co-localization, but not pIgR-overexpression alone, is associated with superior outcomes (FIG. 8J and FIG. 6C). Importantly, coating of tumor cells by IgA, but not IgG, connotes superior outcome (FIG. 13A and FIG. 6D), and is associated with increased intra-epithelial CD8+ and CD4+ T-cells (FIG. 13B).

Figure 13C:
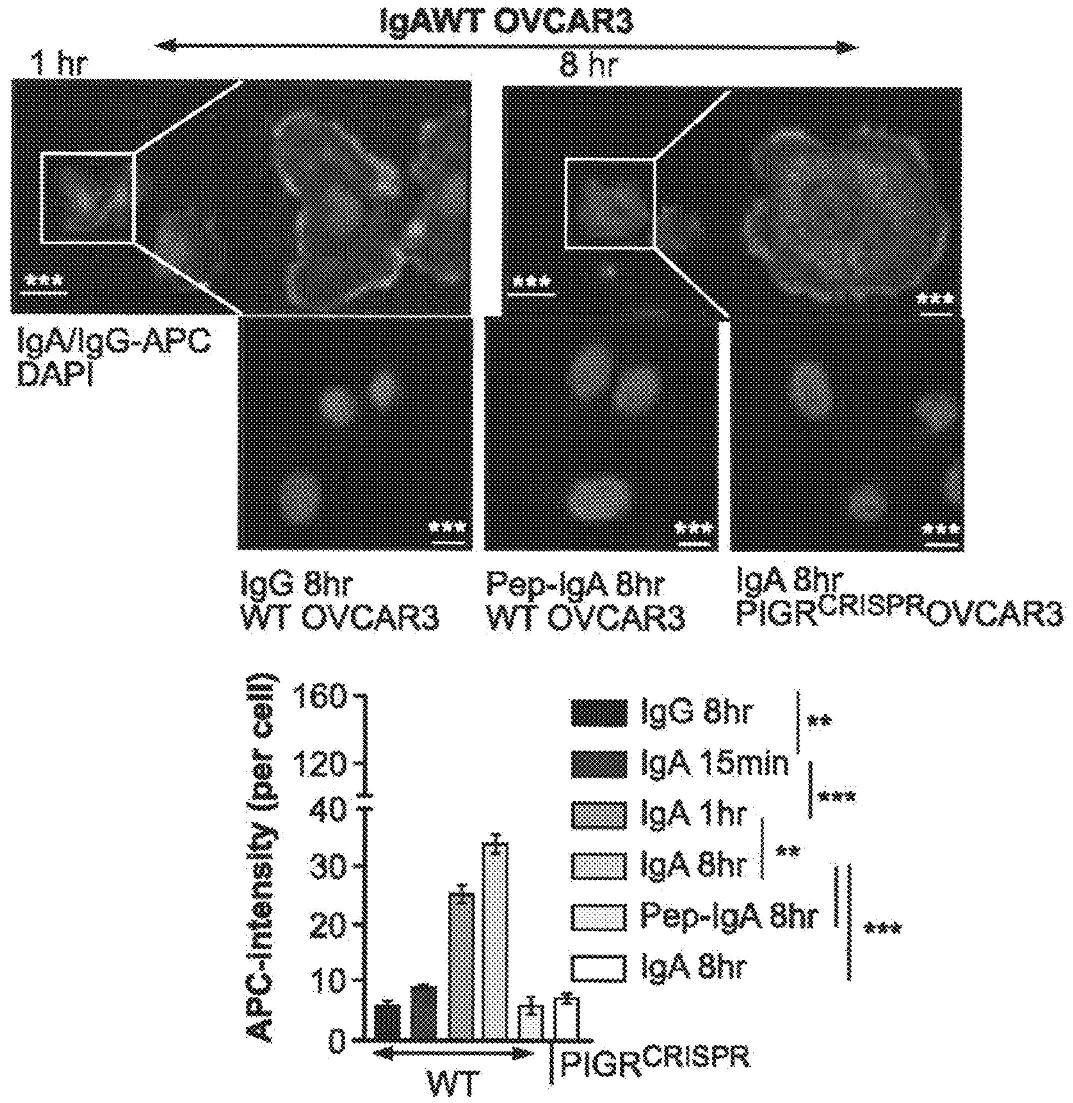
Figure 13D:
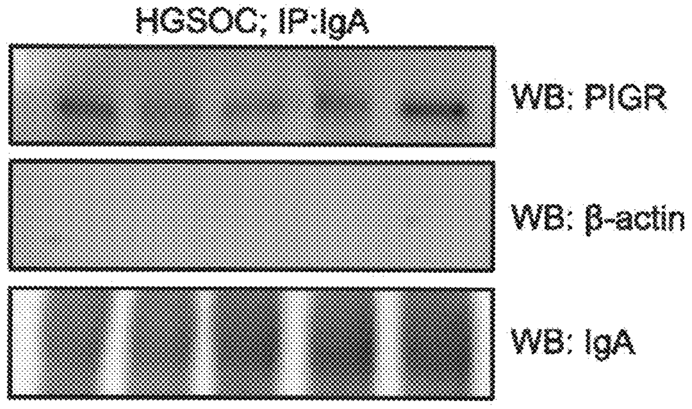
Figure 13E:
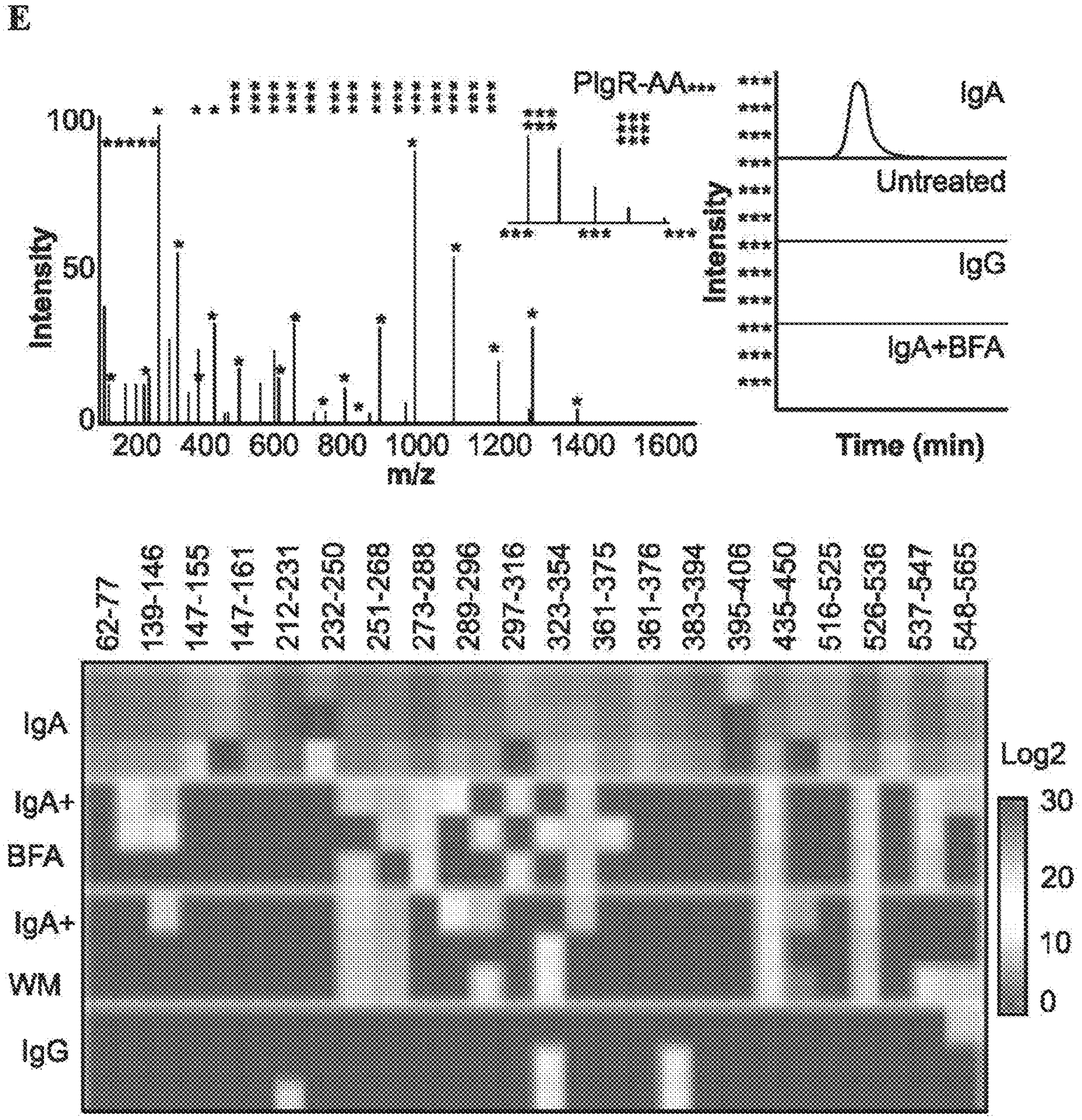
Figure 13F:
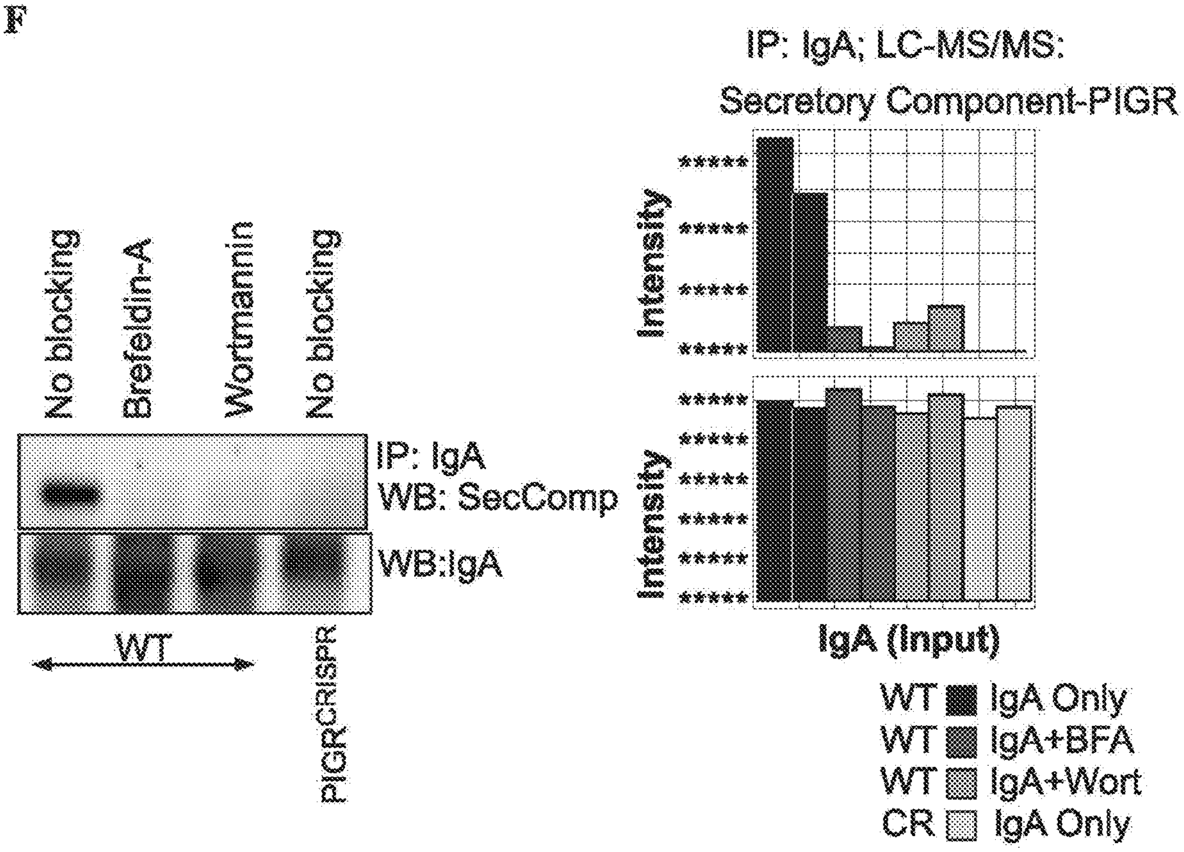
Figure 13G:
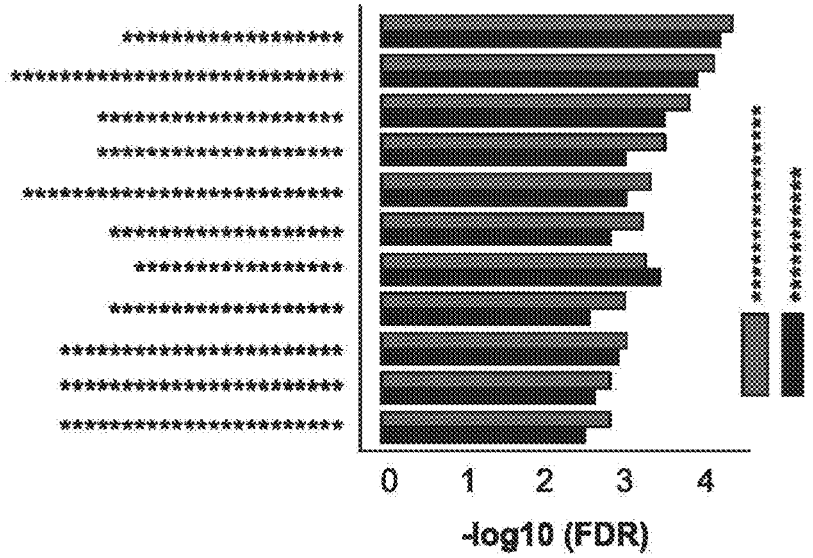

To determine whether the IgA:pIgR interactions elicit transcytosis through tumor cells, we first incubated pIgR+ OVCAR3 ovarian cancer cells with fluorescently-labeled non-antigen specific IgA or IgG (FIG. 13C). Confocal microscopy confirmed that IgA was selectively internalized and deposited on the cell surface within 8 hr (FIG. 13C). Internalization was abrogated upon pepsin-mediated Fc removal or CRISPR-mediated pIgR ablation (FIG. 13C and FIG. 14), and co-immunoprecipitation analyses of IgA and pIgR confirmed their physical interaction in human HGSOC (FIG. 13D). Supporting that IgA indeed transcytoses through tumor cells, multiple peptides of the secretory component were detected in supernatants of OVCAR3, OVCAR4, OVCAR5 or primary ovarian cancer cells incubated with IgA, but not when these cells were co-incubated with the transcytosis inhibitors wortmannin and brefeldin-A, or when cells were incubated with IgG (FIG. 13E, FIG. 15). Finally, IgA co-immunoprecipitated with the secretory component in OVCAR3-supernatants, and this was again abolished by transcytosis inhibitors or pIgR ablation in tumor cells (FIG. 13F).

Figure 13H:
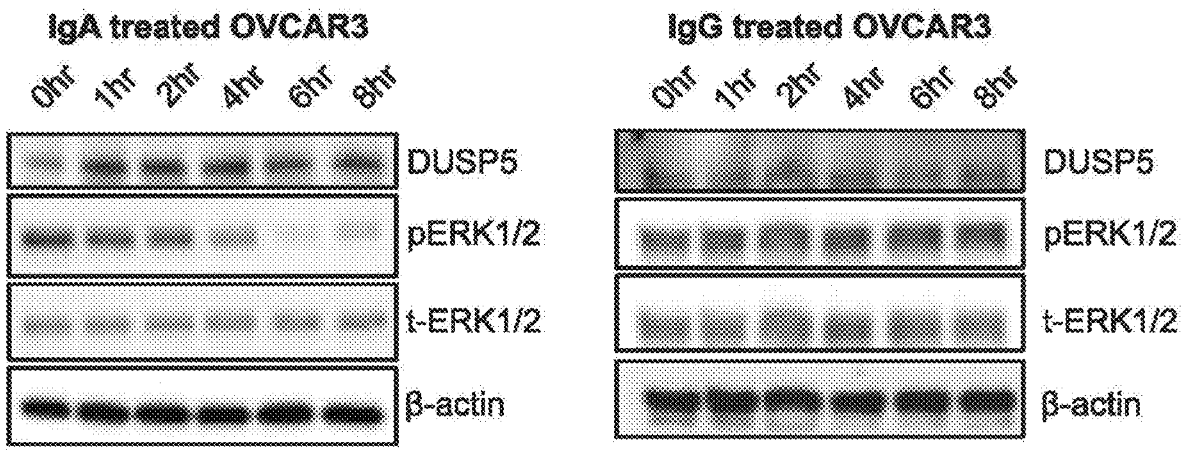
Figure 16B:
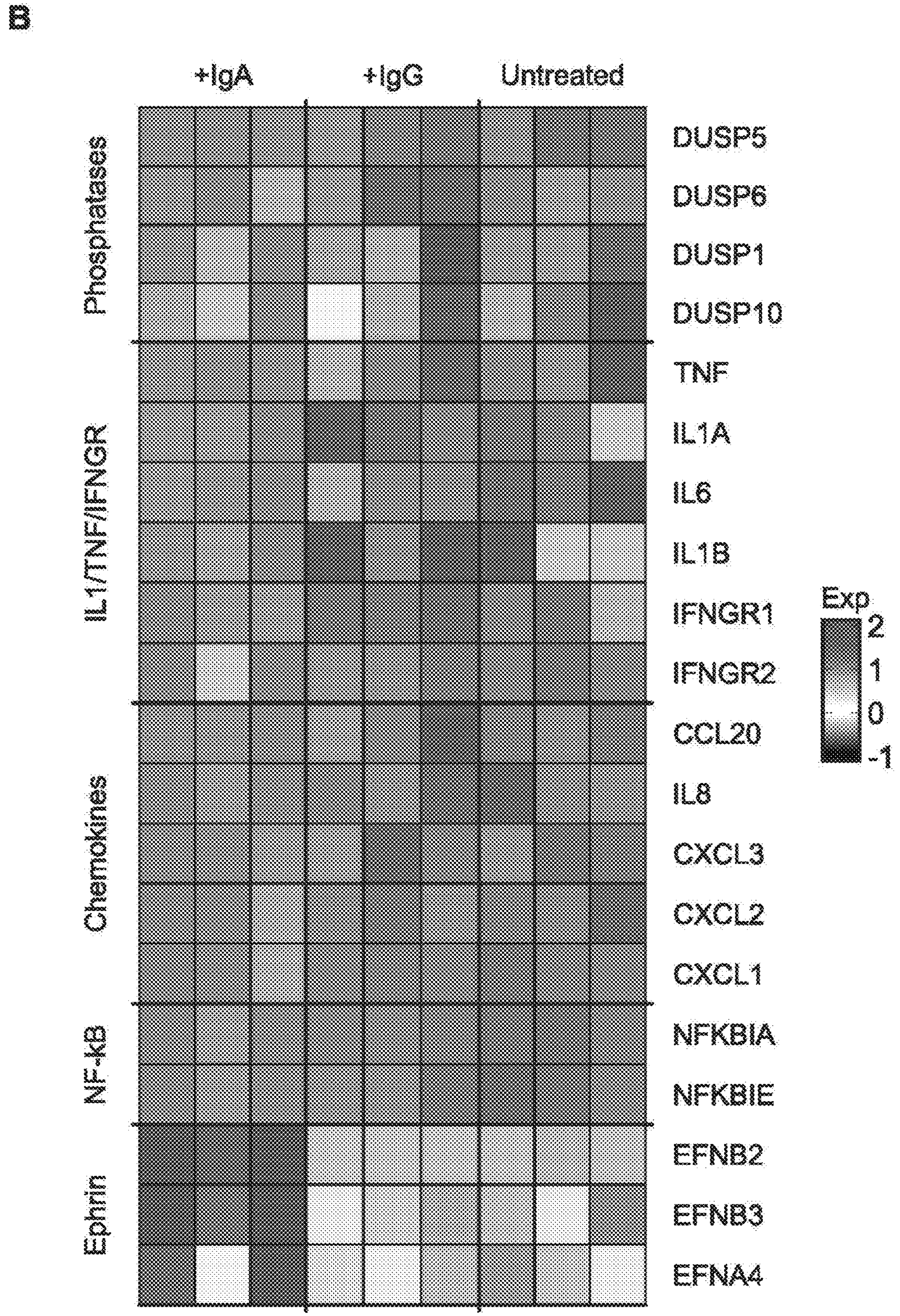

Notably, IgA transcytosis induced broad transcriptional changes in inflammatory pathways in tumor cells, including upregulation of INF-γ receptors (FIG. 13G and FIGS. 16A & 16B), and downregulation of tumor-promoting Ephrins (FIG. 16B). In addition, multiple DUSP phosphatases, known to counteract phosphorylation events downstream of the RAS pathway, were simultaneously elevated upon incubation with non-antigen-specific IgA (but not IgG), at both mRNA (FIG. 16B) and protein levels (FIG. 13H). Finally, increases in DUSP5 were associated with impaired MEK-ERK signaling, as demonstrated by reduced levels of phospho-ERK1/2 (FIG. 13H).

Figure 13I:
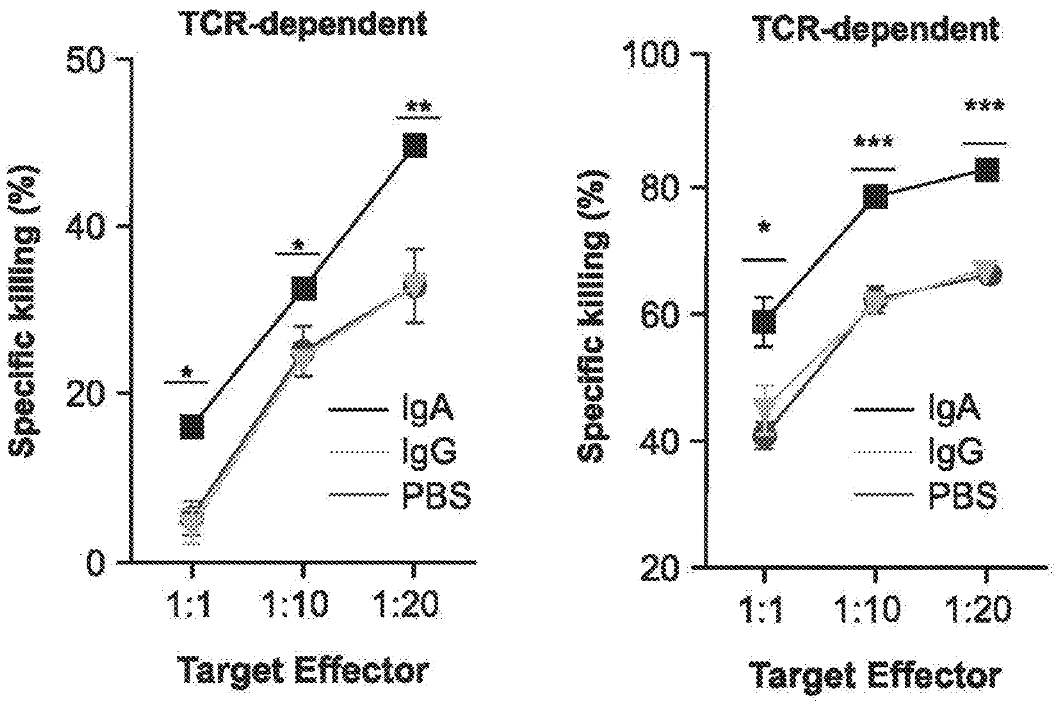
Figure 13J:
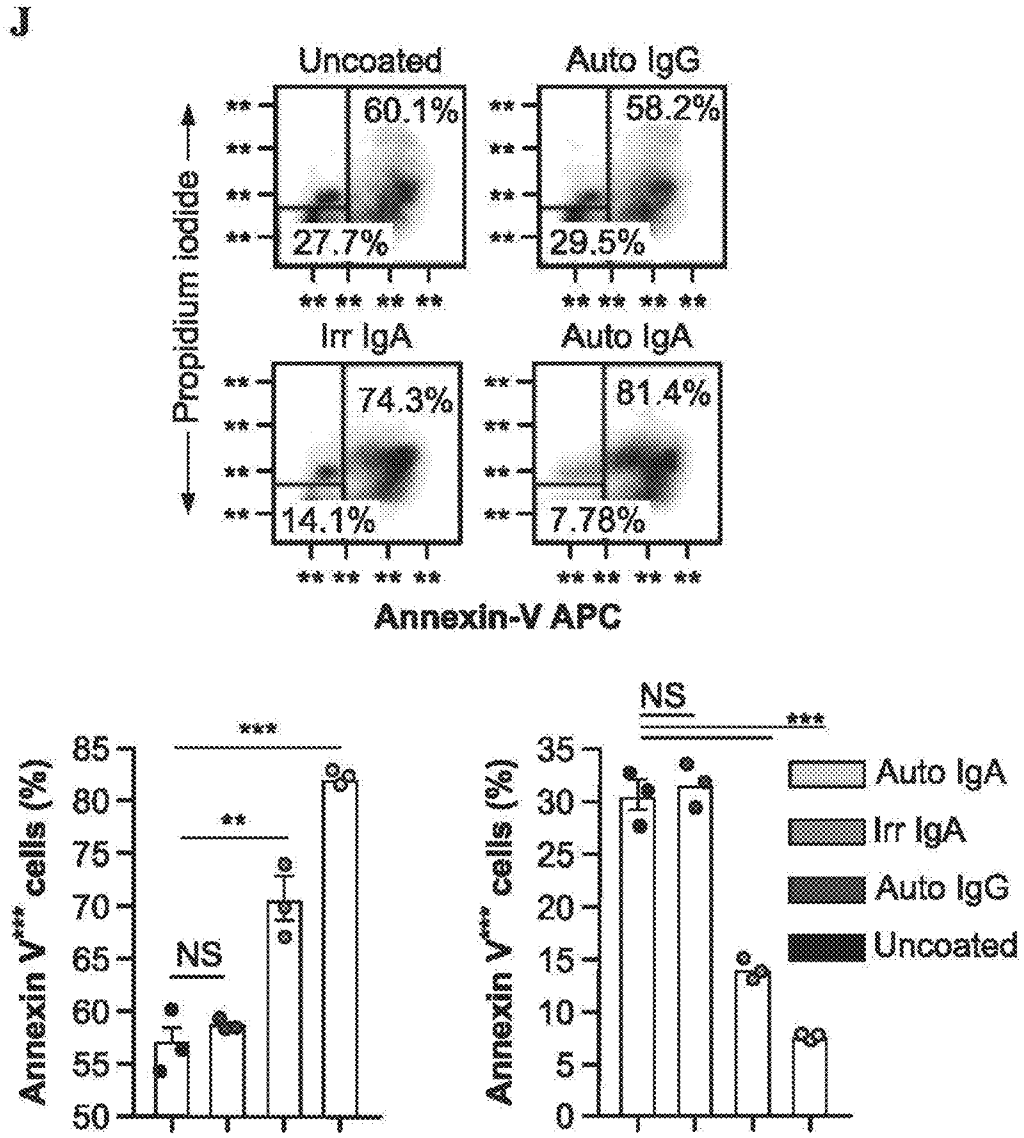
Figure 13K:
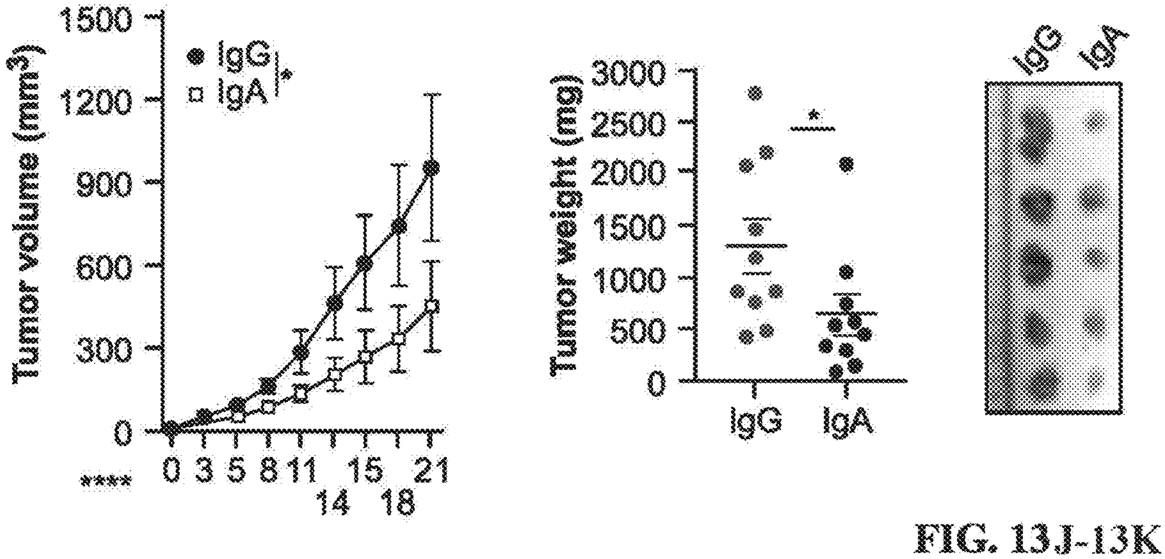
Figure 17A:
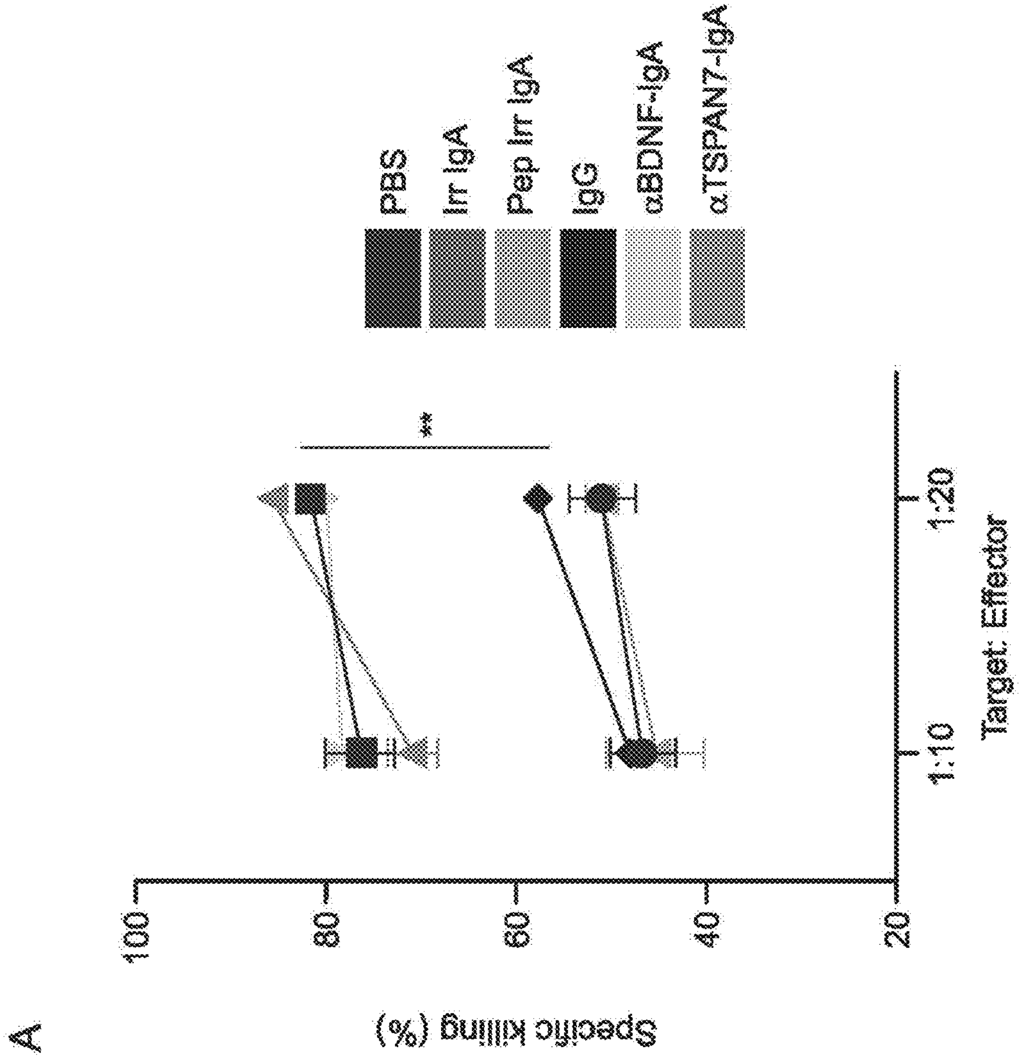
Figure 17B:
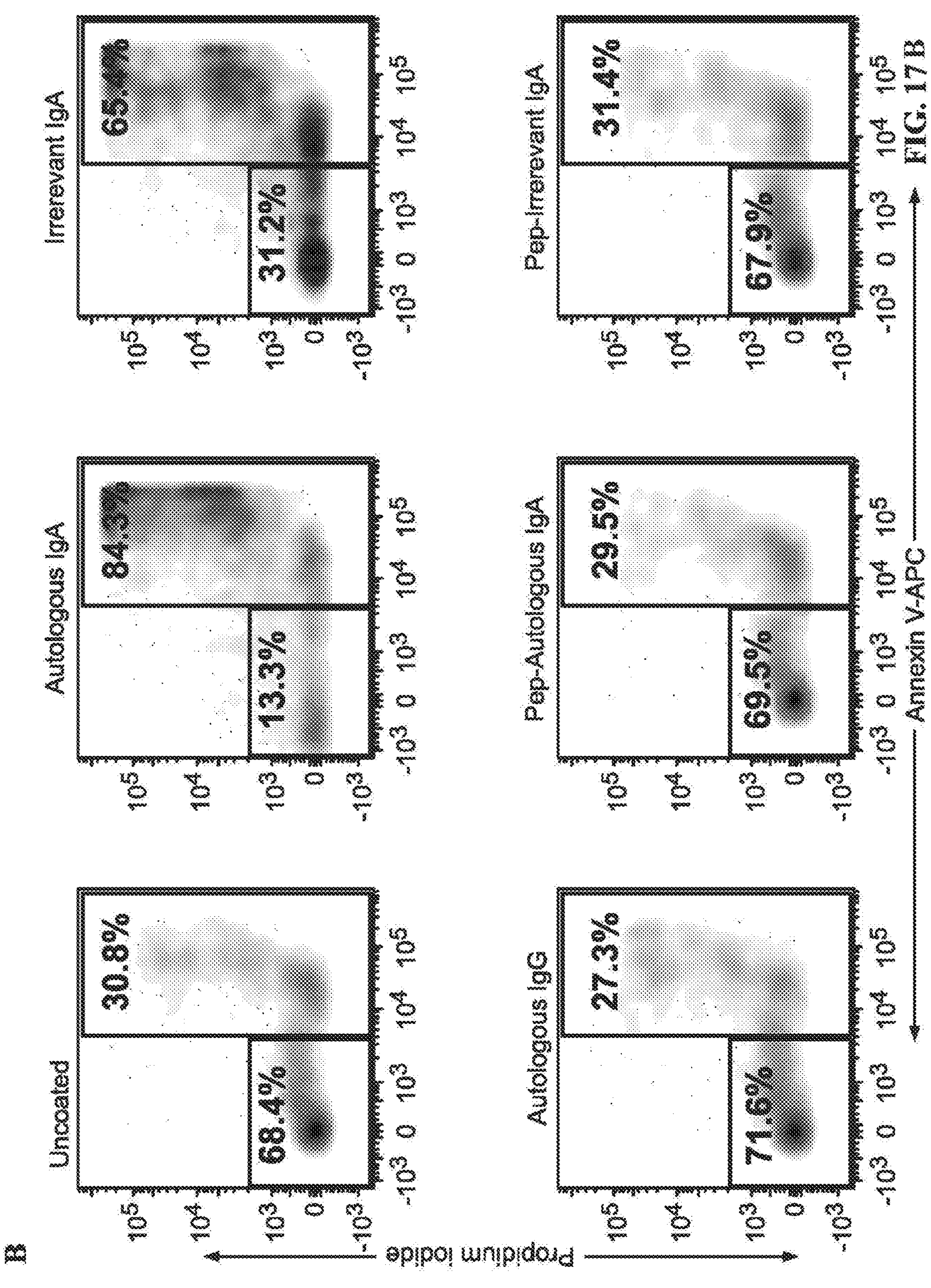
Figure 17C:
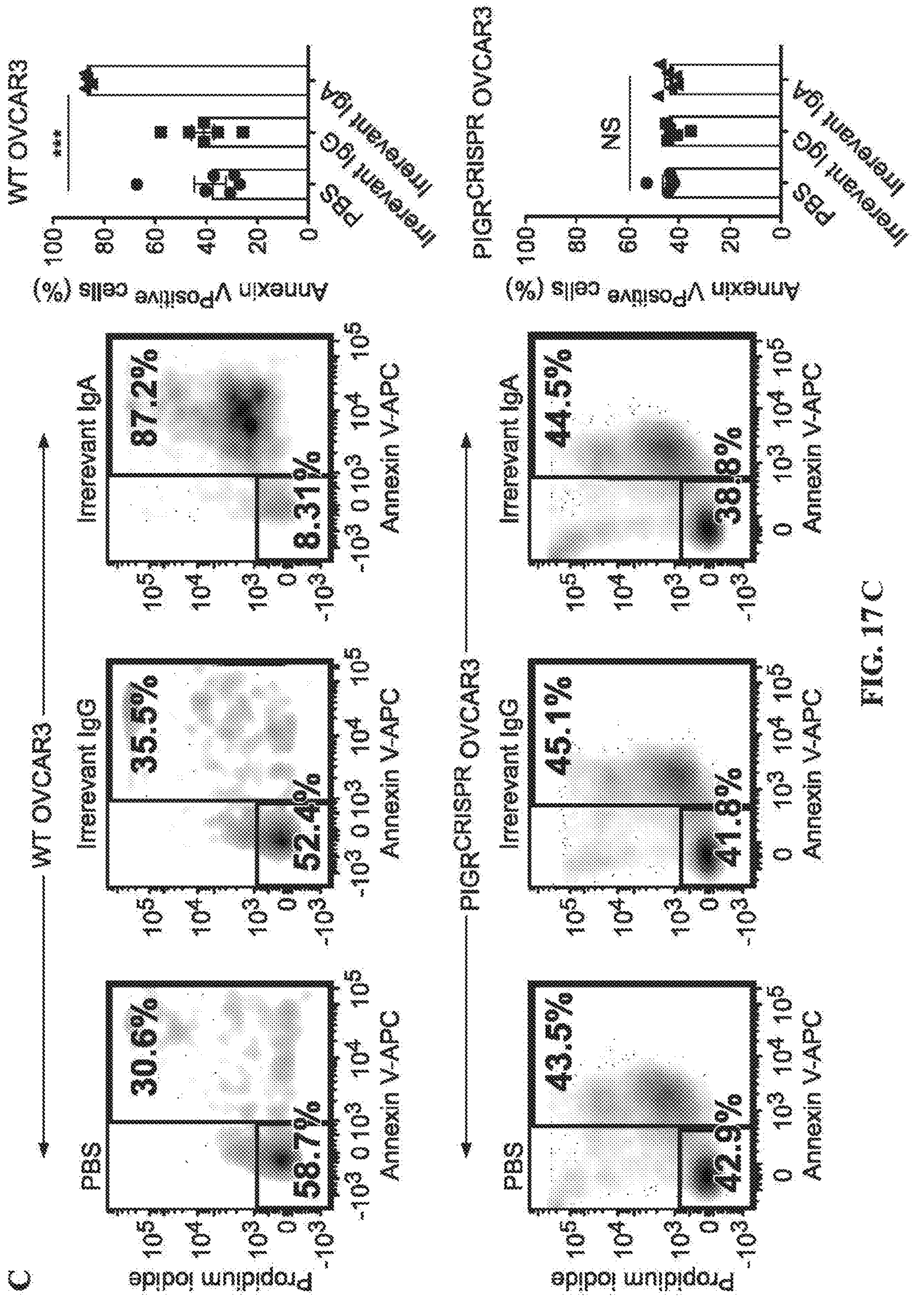

To define the functional relevance of phenotypic changes induced by IgA transcytosis in ovarian cancer cells, we expressed the cancer testis antigen NY-ESO-1 in HLA-A2+ FSHR+ OVCAR3 HGSOC cells, as well as an HLA A2-restricted TCR in human T-cells that recognizes SLLMWITQC, corresponding to 157-165NY-ESO-112. Remarkably, the dose-dependent cytotoxic activity of tumor-antigen-redirected T-cells was enhanced upon incubation with irrelevant IgA, compared to control IgG or vehicle (FIG. 13I, left). These effects were independent of changes in MHC-I expression, as the cytotoxic activity of human T-cells engineered to express an FSH-targeted chimeric receptor, which recognizes FSHR in OVCAR3 cells independently of MHC-I, was enhanced to a similar extent (FIG. 13I, right). Comparable IgA-dependent sensitization of tumor cells to T-cell-mediated killing was identified using expanded tumor-infiltrating lymphocytes and autologous tumor cells from different patients (FIG. 13J), and a similar enhancement was observed using different tumor antigen-specific IgAs (FIG. 17A). Increased T-cell cytotoxicity required IgA-Fc:pIgR interaction, because it was abolished using pepsinized antibodies or pIgR-ablated OVCAR3 cells (FIGS. 17B & 17C). Accordingly, treatment with non-antigen-specific IgA significantly delayed OVCAR3 tumor growth in Rag1-deficient tumor-bearing mice, compared to control IgG or pepsinized IgA (FIG. 13K and FIG. 18). Suppression of tumor growth was not due to any tumor-promoting effect of IgG, as tumor-bearing mice treated with PBS or pepsin-treated (F(ab')2) Ig fragments grew at the same rate as their control IgG-treated counterparts (FIGS. 18 and 19).

Figure 20H:
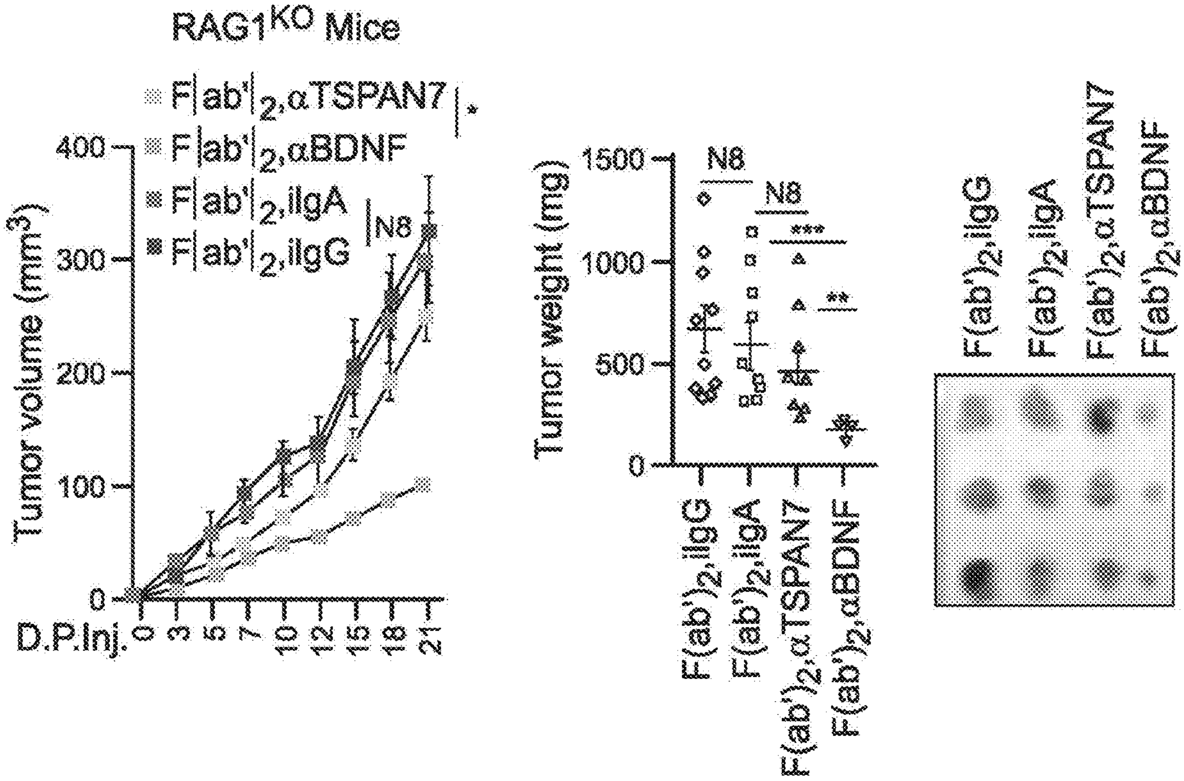
Figures 20I, 20J:
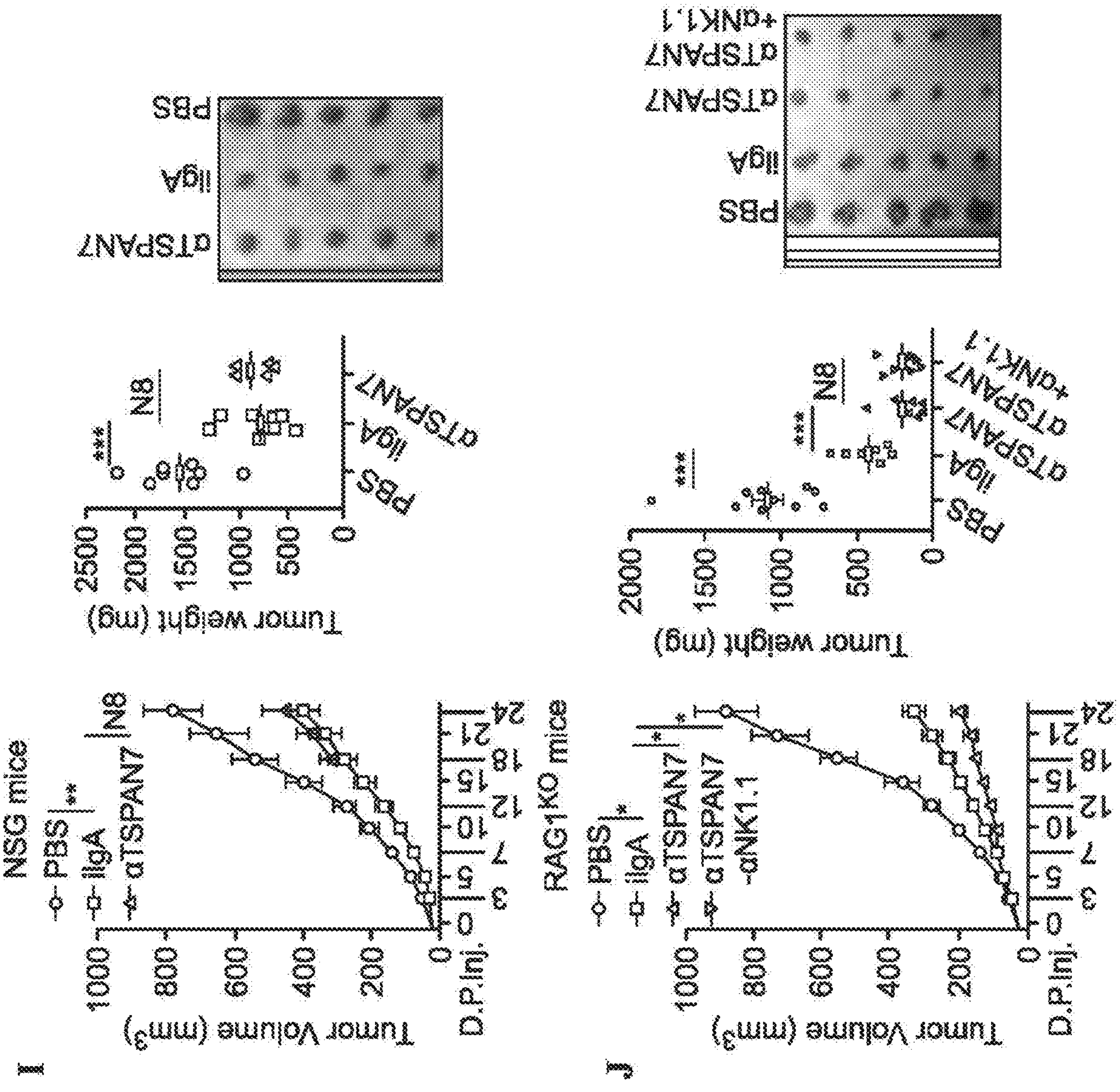
Figures 20K, 20L:
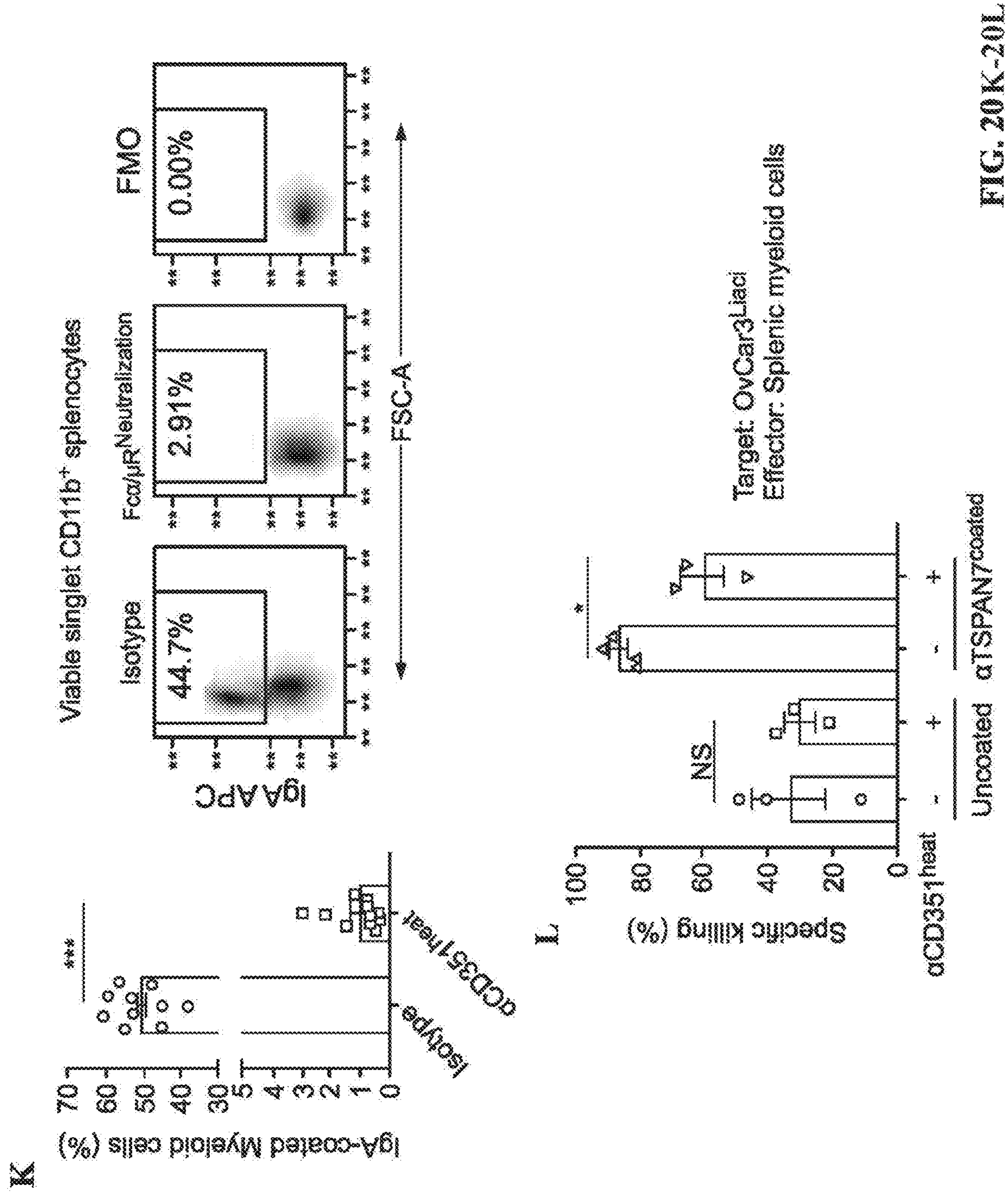
Figures 20M, 20N:
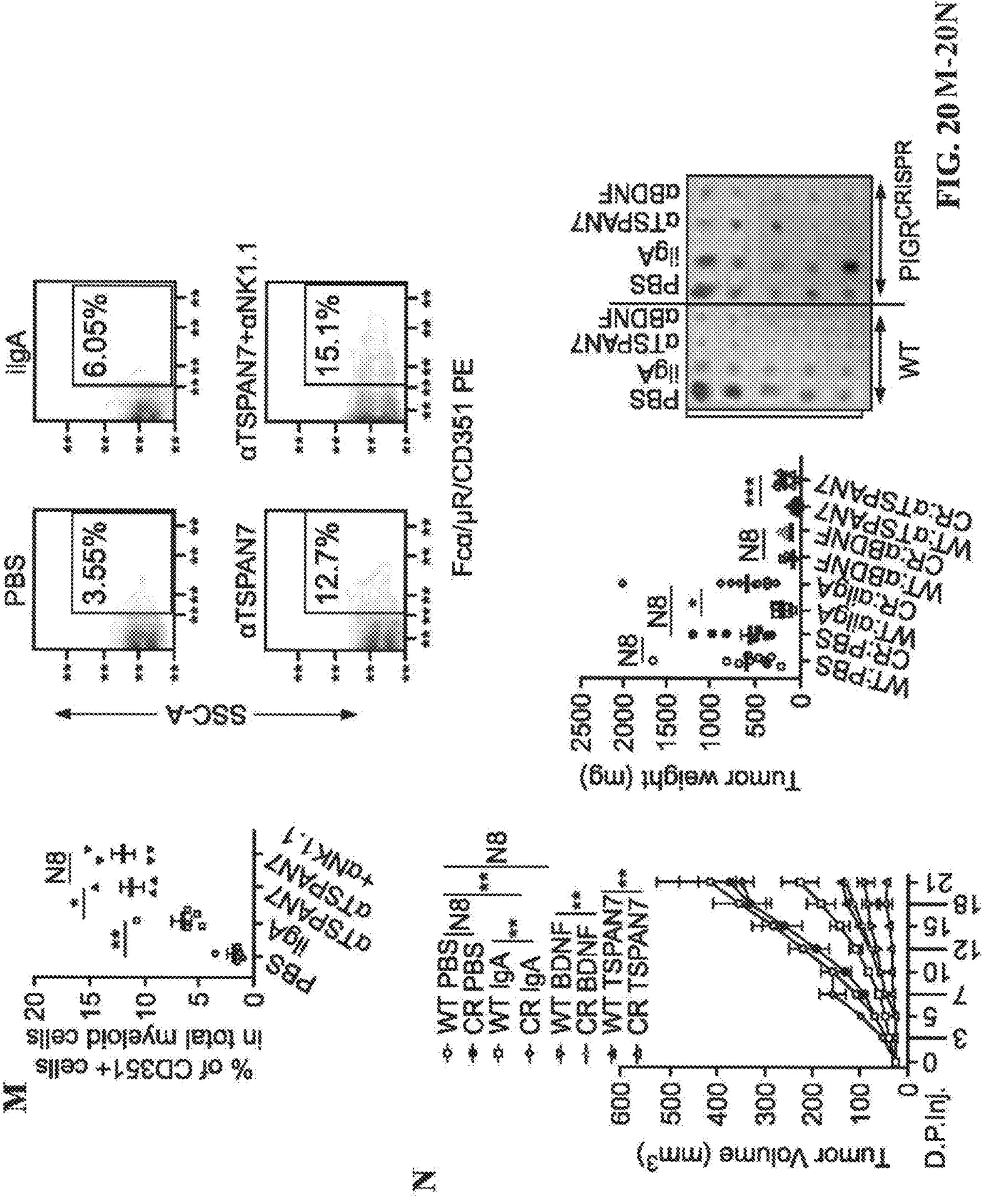
Figures 21A, 21B, 21C, 21D:
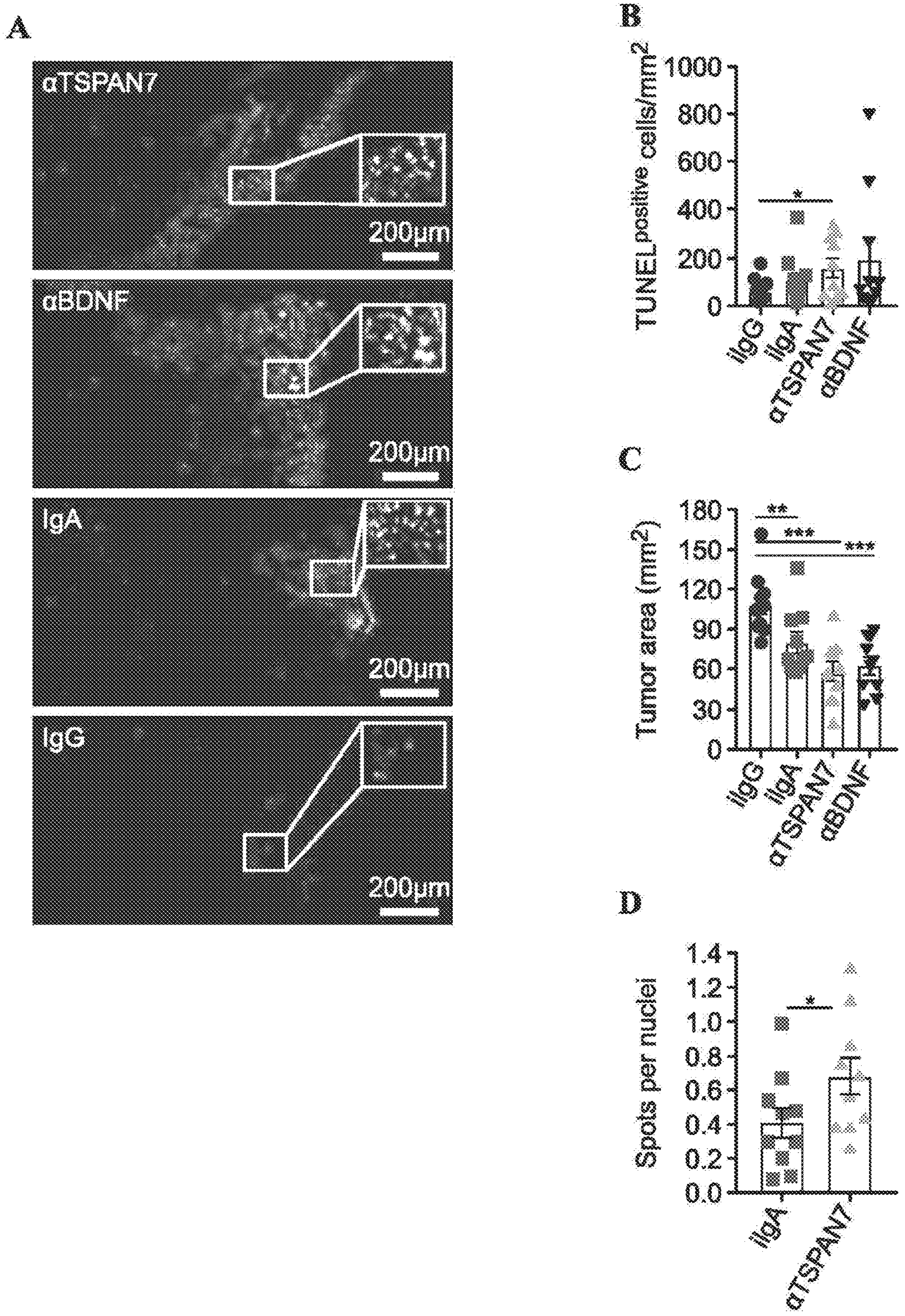

To determine the specificities of antibodies spontaneously generated in ovarian cancer, we optimized a system for the isolation, activation, immortalization and characterization of B cells immunopurified from 10 freshly dissociated HGSOCs, using human proteome arrays (FIG. 20A). We found that IgA and IgG antibodies secreted by tumor-derived B-cells recognized a broad range of tumor antigens, many of which have extracellular domains or represent secreted proteins. To define the functional relevance of extracellular antigen recognition, we focused on TSPAN7, a tetraspanin overexpressed in human carcinomas, and on BDNF, a secreted molecule associated with poor prognosis in HGSOC. A battery of biotinylated 16-20mer peptides contained in the extracellular domains of these molecules was tetramerized using fluorescent streptavidin, and tetramer-reactive B-cells were FACS-sorted from the immortalized batches of intratumoral B-cells, and cultured separately (FIG. 20B). These B-cells predominately produced IgA (FIG. 20C) that specifically recognized these targets expressed in HGSOC tumor cells, as well as recombinant TSPAN7 and BDNF (FIG. 20D). Notably, both TSPAN7- and BDNF-reactive IgAs: 1) antagonized tumor growth in vivo more effectively than irrelevant IgA (FIGS. 20E & 20F); 2) induced areas of central necrosis and TUNEL+ cells (FIG. 20G and FIG. 21A-C); and 3) were engulfed by tumor cells more effectively than irrelevant IgA (FIG. 21D). Interestingly, the anti-tumor effects of BDNF-specific antibodies were retained upon removal of the Fc domain, suggestive of neutralization of secreted BDNF, while pepsinized anti-TSPAN7 antibodies lost their anti-tumor activity, suggestive of antibody-dependent cellular cytotoxicity/phagocytosis (ADCC/ADCP) (FIG. 20H). Accordingly, the superior activity of TSPAN7 antibodies, compared to control IgA, disappeared in NSG mice, which lack functional macrophages, dendritic cells and NK cells (FIG. 20I). NK cell depletion in tumor-bearing Rag1 knockout mice (FIG. 22) had no effect on anti-tumor activity (FIG. 20J). Further supporting ADCP, splenic myeloid cells from tumor-bearing (CD89-deficient) mice bound IgA through Fcα/μR (CD351) (FIG. 20K), and killed OVCAR3 targets more effectively upon coating with TSPAN7 IgA (FIG. 20L). Importantly, there were increases in CD351+ myeloid cells at tumor beds after treatment with TSPAN7 antibodies, compared to control IgA (FIG. 20M). Therefore, polyclonal tumor antigen-specific IgA responses hinder malignant progression through at least two independent mechanisms.

Figures 24A, 24B:
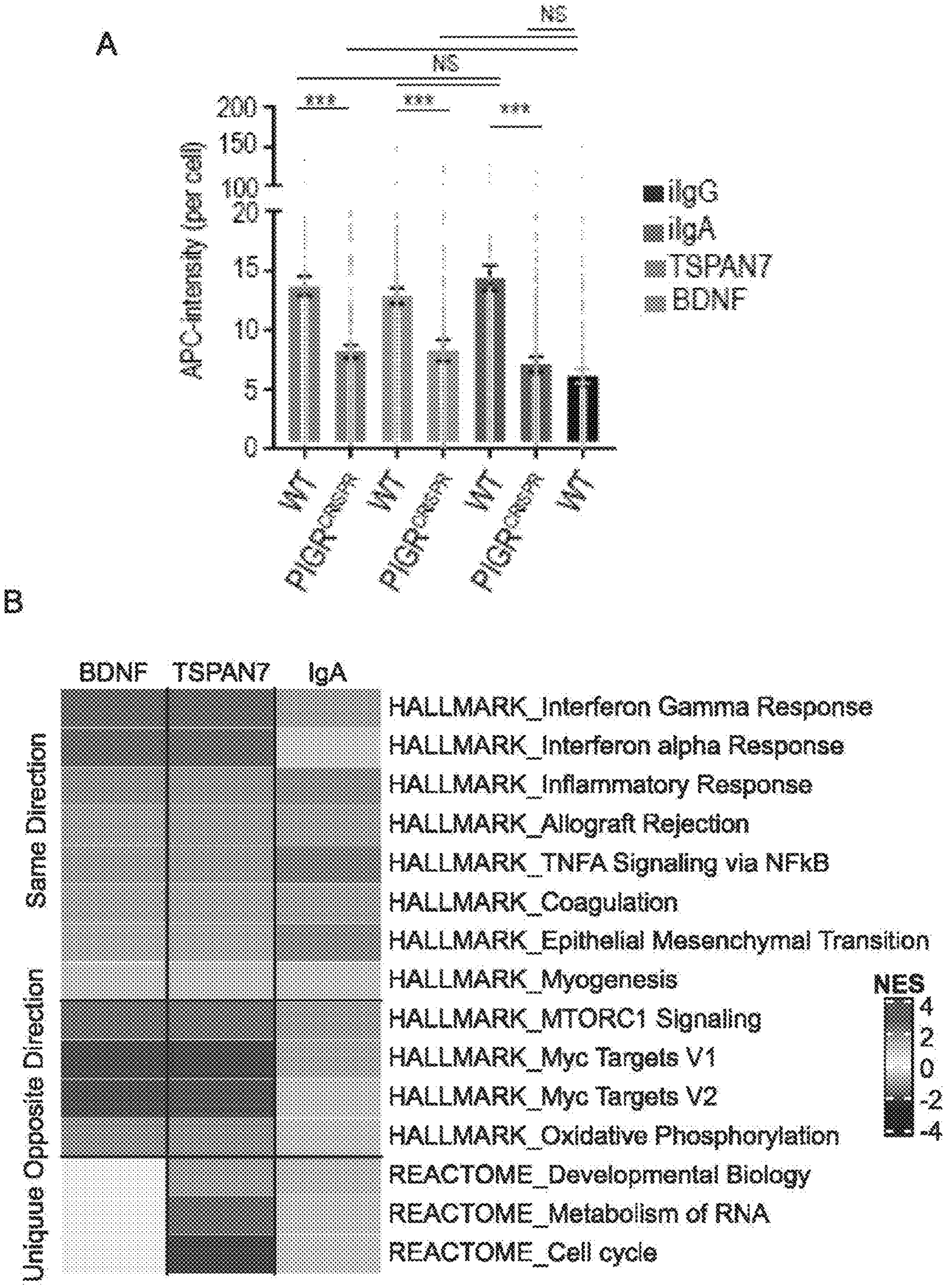

To define the role of pIgR-mediated IgA transcytosis in anti-tumor activity, Rag1-deficient mice were challenged with pIgR-ablated OVCAR3 tumors. Notably, the protective effect of non-antigen-specific IgA disappeared in both Rag1-deficient and NSG mice (FIG. 20N and FIG. 23), while tumor-derived TSPAN7 and BDNF antibodies showed decreased anti-tumor effects, consistent with the capacity to transcytose through tumor cells (FIG. 24A & FIG. 24B).

Characterization of discrete conglomerates of B- and T-cells identified as Tertiary Lymphoid Structures (TLS), which were present in ~21% of HGSOCs (FIG. 25A), revealed that these TLS+ harbored positive spatial interactions between CD4+, CD8+, and B-lymphocytes (CD20+), and that spatial interactions of CD8+ and B-lymphocyte dominated (FIG. 25B). Further, as reported, the presence of TLS was associated with improved outcome (FIG. 25C), and with increased B-cell, CD4+ and CD8+ T-cells infiltrates (FIG. 25D). Increased expression of CXCL13, which is produced by T-Follicular Helper Cells and is a marker of germinal center formation, was also associated with a superior survival in TCGA ovarian cancer datasets (FIG. 9). Notably, >80% of the total BCRs were due to only 2-3 B-cell clones in 4 laser-capture microdissected TLS from frozen sections of different HGSOCs (FIG. 25E and FIG. 26). Dominant CDR3 sequences in TLS were below detection levels among the polyclonal response detected for the whole tumor (FIG. 25E and FIG. 26), yet all TLS identified in 6 frozen specimens from 40 different HGSOC patients contained IgA-producing B cells (FIG. 25F and FIG. 27).

Cancer cells in close proximity (<500 μm) of the TLS-B-cell conglomerates showed distinctive transcriptional profiles (i.e., higher levels of CCL20; FIG. 25G). Finally, consistent with the role of TGF-β signaling in IgA isotype-switching, the expression of T-cell-specific markers and effector molecules was significantly elevated in TCGA ovarian tumors expressing higher levels of TGF-β, challenging the notion that this cytokine is consistently immunosuppressive (FIG. 9).

Collectively these data demonstrate that IgA produced in the ovarian cancer microenvironment contributes to thwarting malignant progression by both neutralizing extracellular oncogenic drivers in an antigen-specific manner, and via non-specific transcytosis through pIgR+ tumor cells. Further, IgA-dominated B-cell responses in human HGSOC, including the assembly of TLS, are consistently associated with immune-reactive landscapes and superior outcomes. These findings indicate that immunotherapies that boost both coordinated B and T-cell responses against human ovarian cancer, an immunogenic disease currently resistant to checkpoint inhibitors, are likely to show therapeutic benefit. In support of this notion, similar synergy has been suggested for other malignancies. As successful vaccines work by inducing humoral responses, identifying other pIgR+ mucosal tumors with protective IgA responses lead to novel anti-cancer immunotherapies exploiting this major arm of adaptive immunity.

Example 6 Staining of PD-1 Using IgA Antibody

PBMCs from a healthy donor were CD3/CD28-activated for 48 hours and lysates were run in a conventional western blot (WB), along with lysates of OVCAR3 tumor cells (negative control). The anti-PD-1 antibody, purified from serum-free supernatants of PD-1-specific, monoclonal, immortalized B cells, was diluted at 1:2000 and used to stain the membrane. After washing, the membrane was incubated with an anti-human IgA Ab (Abcam; 1:5000 dilution). Beta actin was stained after PD-1 was developed. PD-1 is detected at the expected size (~50 kDa). FIG. 28 shows the WB showing positive staining of PD-1 by our IgA using activated T cells, but not OVCAR3 tumor cells

Example 7: Anti-CoV19 Antibody

B cells can be sorted, activated and EBV-infected as described in the general protocol. Antibody-producing B cells are then sorted using tetramers generated against predicted epitopes contained in the RBM domain (underlined) of the S1 protein of SARS-COV-2, as depicted below. This region of the virus is crucial for interactions with the ACE2 receptor in host's cells (PMID: 32155444, 32142651, 32132184). Neutralizing antibodies can prevent viral spread in patients that have been infected, as well as minimizing new infections in people exposed to the virus (i.e., medical personnel). B cells producing antibodies reacting against these epitopes can be sorted and clones will be made through FACS sorting and/or limiting dilution. As reported in the main protocol, the sequence of the $V_H$ and $V_L$ of these monoclonal antibodies can be cloned through multiplex PCR and sequenced. Affinity maturation will be then performed in vitro by exposing clonal B cells to plated bound antigen, in the presence of IL-21.

For therapeutic or prophylactic purposes, a cocktail of a number of antibodies can be used, to prevent resistances arising from viral mutations.

amino acid sequence for S1 (RBM); S2

SEQ ID NO: 11

MFIFLLFLTLTSGSDLDRCTTFDDVQAPNYTQHTSSMRGVYYPDEIFRSDTLYLTQDLFL

PFYSNVTGFHTINHTFGNPVIPFKDGIYFAATEKSNVVRGWVFGSTMNNKSQSVIIINNST

NVVIRACNFELCDNPFFAVSKPMGTQTHTMIFDNAFNCTFEYISDAFSLDVSEKSGNFKH

LREFVFKNKDGFLYVYKGYQPIDVVRDLPSGFNTLKPIFKLPLGINITNFRAILTAFSPAQ

DIWGTSAAAYFVGYLKPTTFMLKYDENGTITDAVDCSONPLAELKCSVKSFEIDKGIYQ

TSNFRVVPSGDVVRFPNITNLCPFGEVFNATKFPSVYAWERKKISNCVADYSVLYNSTFF

STFKCYGVSATKLNDLCFSNVYADSFVVKGDDVRQIAPGQTGVIADYNYKLPDDFMGC

VLAWNTRNIDATSTGNYNYKYRYLRHGKLRPFERDISNVPFSPDGKPCTPPALNCYWPL

NDYGFYTTTGIGYQPYRVVVLSFELLNAPATVCGPKLSTDLIKNQCVNFNFNGLTGTGV

LTPSSKRFQPFQQFGRDVSDFTDSVRDPKTSEILDISPCSFGGVSVITPGTNASSEVAVLY

QDVNCTDVSTAIHADQLTPAWRIYSTGNNVFQTQAGCLIGAEHVDTSYECDIPIGAGICA

SYHTVSLLRSTSQKSIVAYTMSLGADSSIAYSNNTIAIPTNFSISITTEVMPVSMAKTSVDC

NMYICGDSTECANLLLQYGSFCTQLNRALSGIAAEQDRNTREVFAQVKQMYKTPTLKY

FGGFNFSQILPDPLKPTKRSFIEDLLFNKVTLADAGFMKQYGECLGDINARDLICAQKFN

GLTVLPPLLTDDMIAAYTAALVSGTATAGWTFGAGAALQIPFAMQMAYRFNGIGVTQN

VLYENQKQIANQFNKAISQIQESLTTTSTALGKLQDVVNQNAQALNTLVKQLSSNFGAI

SSVLNDILSRLDKVEAEVQIDRLITGRLQSLQTYVTQQLIRAAEIRASANLAATKMSECV

LGQSKRVDFCGKGYHLMSFPQAAPHGVVFLHVTYVPSQERNFTTAPAICHEGKAYFPR

EGVFVFNGTSWFITQRNFFSPQIITTDNTFVSGNCDVVIGIINNTVYDPLQPELDSFKEELD

-continued

KYFKNHTSPDVDLGDISGINASVVNIQKEIDRLNEVAKNLNESLIDLQELGKYEQYIKWP

WYVWLGFIAGLIAIVMVTILLCCMTSCCSCLKGACSCGSCCKFDEDDSEPVLKGVKLHY

T

Epitopes for S1:

(SEQ ID NO: 12)
MGCVLAWNTRNIDATS, (SEQ ID NO: 13)
LRHGKLRPFERDISNV, and the Non-linear epitope:

(SEQ ID NO: 14)
LSNVPFSPDGKPCTPPALNCYW

SEQUENCES
SEQ ID NO: 1: IGHV1-8*01/IGHD6/IGHJ6 Variable Heavy ($V_H$) Chain amino acid sequence
QLVQSGAEVKKPGASVKVSCKASGYTFTSYDINWVRQATGQGLEWMGWMNPNSGNT

GYAQKFQGRVTMTRNTSISTAYMELSSLRSEDTAVYYCARGGGASSWYSVYYYYYMD

VWGKGTTVTVSS

SEQ ID NO: 2: IGKV3D-11/IGKJ3*01 Variable Kappa Light ($V_L$) Chain amino acid sequence
EIVMTQSPATLSLSPGERATLSCRASQGVSSYLAWYQQKPGQAPRLLIYDASNRATGIPA

RFSGSGPGTDFTLTISSLEPEDFAVYYCQQYNNWPPLFTFGPGTKVDIK

IGHV1-8*01/IGHD6/IGHJ6 Heavy Chain CDR1
SEQ ID NO: 3
GYTFTSYDIN

IGHV1-8*01/IGHD6/IGHJ6 Heavy Chain CDR2
SEQ ID NO: 4
WMNPNSGNTGYAQ

IGHV1-8*01/IGHD6/IGHJ6 Heavy Chain CDR3
SEQ ID NO: 5
RGGGASSWYSVYYYYYMDV

IGKV3D-11/IGKJ3*01 Variable Kappa Light Chain CDR1
SEQ ID NO: 6
RASQGVSSYLA

IGKV3D-11/IGKJ3*01 Variable Kappa Light Chain CDR2
SEQ ID NO: 7
DASNRAT

IGKV3D-11/IGKJ3*01 Variable Kappa Light Chain CDR3
SEQ ID NO: 8
QQYNNWPPLFT

IGHV1-8*01/IGHD6/IGHJ6 Heavy Chain nucleic acid sequence
SEQ ID NO: 9
AGGTGCAGCTGGTGCAGTCTGGGGCTGAGGTGAAGAAGCCTGGGGCCTCAGTGAAG

GTCTCCTGCAAGGCTTCTGGATACACCTTCACCAGTTATGATATCAACTGGGTGCGA

CAGGCCACTGGACAAGGGCTTGAGTGGATGGGATGGAAACCCTAACAGTGGTAA

CACAGGCTATGCACAGAAGTTCCAGGGCAGAGTCACCATGACCAGGAACACCTCCA

TAAGCACAGCCTACATGGAGCTGAGCAGCCTGAGATCTGAGGACACGOCCGTGTAT

TACTGTGCGAGAGGGGGGGGGGCCAGCAGCTGGTACTCGGTGTACTACTACTACTA

CATGGACGTCTGGGGCNAAGGGACCACGGTCACCGTCTCCTCAG

IGKV3D-11/IGKJ3*01 Variable Kappa Light Chain nucleic acid sequence
SEQ ID NO: 10
GAGAAATAGTGATGACGCAGTCTCCAGCCACCCTGTCTGTGTCTCCAGGGGAAAGA

GCCACCCTCTCCTGCAGGGCCAGTCAGAGTGTTAGCAGCAACTTAGCCTGGTACCA

GCAGAAACCTGGCCAGGCTCCCAGGCTCCTCATCTATGGTGCATCCACCAGGGCCA

-continued

CTGGTATCCCAGCCAGGTTCAGTGGCAGTGGGTCTGGGACAGAGTTCACTCTCACCA

TCAGCAGCCTGCAGTCTGAAGATTTTGCAGTTTATTACTGTCAGCAGTATAATAACT

GGCCTCCTCTATTCACTTTCGGCCCTGGGACCAAAGTGGATATCAAA amino acid sequence for S1 (RBM); S2

SEQ ID NO: 11

MFIFLLFLTLTSGSDLDRCTTFDDVQAPNYTQHTSSMRGVYYPDEIFRSDTLYLTQDLFL

PFYSNVTGFHTINHTFGNPVIPFKDGIYFAATEKSNVVRGWVFGSTMNNKSQSVIIINNST

NVVIRACNFELCDNPFFAVSKPMGTQTHTMIFDNAFNCTFEYISDAFSLDVSEKSGNFKH

LREFVFKNKDGFLYVYKGYQPIDVVRDLPSGFNTLKPIFKLPLGINITNFRAILTAFSPAQ

DIWGTSAAAYFVGYLKPTTFMLKYDENGTITDAVDCSONPLAELKCSVKSFEIDKGIYQ

TSNFRVVPSGDVVRFPNITNLCPFGEVFNATKFPSVYAWERKKISNCVADYSVLYNSTFF

STFKCYGVSATKLNDLCFSNVYADSFVVKGDDVRQIAPGQTGVIADYNYKLPDDFMGC

VLAWNTRNIDATSTGNYNYKYRYLRHGKLRPFERDISNVPFSPDGKPCTPPALNCYWPL

NDYGFYTTTGIGYQPYRVVVLSFELLNAPATVCGPKLSTDLIKNQCVNFNFNGLTGTGV

LTPSSKRFQPFQQFGRDVSDFTDSVRDPKTSEILDISPCSFGGVSVITPGTNASSEVAVLY

QDVNCTDVSTAIHADQLTPAWRIYSTGNNVFQTQAGCLIGAEHVDTSYECDIPIGAGICA

SYHTVSLLRSTSQKSIVAYTMSLGADSSIAYSNNTIAIPTNFSISITTEVMPVSMAKTSVDC

NMYICGDSTECANLLLQYGSFCTQLNRALSGIAAEQDRNTREVFAQVKQMYKTPTLKY

FGGFNFSQILPDPLKPTKRSFIEDLLFNKVTLADAGFMKQYGECLGDINARDLICAQKFN

GLTVLPPLLTDDMIAAYTAALVSGTATAGWTFGAGAALQIPFAMQMAYRFNGIGVTQN

VLYENQKQIANQFNKAISQIQESLTTTSTALGKLQDVVNQNAQALNTLVKQLSSNFGAI

SSVLNDILSRLDKVEAEVQIDRLITGRLQSLQTYVTQQLIRAAEIRASANLAATKMSECV

LGQSKRVDFCGKGYHLMSFPQAAPHGVVFLHVTYVPSQERNFTTAPAICHEGKAYFPR

EGVFVFNGTSWFITQRNFFSPQIITTDNTFVSGNCDVVIGIINNTVYDPLQPELDSFKEELD

KYFKNHTSPDVDLGDISGINASVVNIQKEIDRLNEVAKNLNESLIDLQELGKYEQYIKWP

WYVWLGFIAGLIAIVMVTILLCCMTSCCSCLKGACSCGSCCKFDEDDSEPVLKGVKLHY

T

Epitope for S1

SEQ ID NO: 12

MGCVLAWNTRNIDATS

Epitope for S1

SEQ ID NO: 13

LRHGKLRPFERDISNV

Epitope for S1

SEQ ID NO: 14

LSNVPFSPDGKPCTPPALNCYW

REFERENCES

Andreu, P. et al. FcRgamma activation regulates inflammation-associated squamous carcinogenesis. *Cancer Cell* 17, 121-134, doi: 10.1016/j.ccr.2009.12.019 (2010).

Boland, J. L. et al. Early disease progression and treatment discontinuation in patients with advanced ovarian cancer receiving immune checkpoint blockade. *Gynecol Oncol* 152, 251-258, doi: 10.1016/j.ygyno.2018.11.025 (2019).

Boyd, A. W., Bartlett, P. F. & Lackmann, M. Therapeutic targeting of EPH receptors and their ligands. *Nat Rev Drug Discov* 13, 39-62, doi: 10.1038/nrd4175 (2014).

Brandtzaeg, P. Mucosal immunity in the female genital tract. *J Reprod Immunol* 36, 23-50 (1997).

Cabrita, R. et al. Tertiary lymphoid structures improve immunotherapy and survival in melanoma. *Nature* 577, 561-565, doi: 10.1038/s41586-019-1914-8 (2020).

Cardone, M. & Mostov, K. Wortmannin inhibits transcytosis of dimeric IgA by the polymeric immunoglobulin receptor. *FEBS Lett* 376, 74-76 (1995).

Conejo-Garcia, J. R. et al. Ovarian carcinoma expresses the NKG2D ligand Letal and promotes the survival and expansion of CD28-antitumor T cells. *Cancer Res* 64, 2175-2182 (2004).

Coukos, G., Conejo-Garcia, J. R., Roden, R. B. & Wu, T. C. Immunotherapy for gynaecological malignancies. *Expert Opin Biol Ther* 5, 1193-1210 (2005).

Counihan, N. A. & Anderson, D. A. Specific IgA Enhances the Transcytosis and Excretion of Hepatitis A Virus. *Sci Rep* 6, 21855, doi: 10.1038/srep21855 (2016).

Cubillos-Ruiz, J. R. et al. CD277 is a Negative Co-stimulatory Molecule Universally Expressed by Ovarian Cancer Microenvironmental Cells. *Oncotarget* 1, 329-328 (2010).

Cubillos-Ruiz, J. R. et al. E R Stress Sensor XBP1 Controls Anti-tumor Immunity by Disrupting Dendritic Cell Homeostasis. *Cell* 161, 1527-1538, doi: 10.1016/j.cell.2015.05.025 S0092-8674 (15) 00575-9 [pii] (2015).

Cubillos-Ruiz, J. R. et al. Polyethylenimine-based siRNA nanocomplexes reprogram tumor-associated dendritic cells via TLR5 to elicit therapeutic antitumor immunity. *J Clin Invest* 119, 2231-2244 (2009).

Curiel, T. J. et al. Blockade of B7-H1 improves myeloid dendritic cell-mediated antitumor immunity. *Nat Med* 9, 562-567, doi: 10.1038/nm863 nm863 [pii] (2003).

Curiel, T. J. et al. Specific recruitment of regulatory T cells in ovarian carcinoma fosters immune privilege and predicts reduced survival. *Nat Med* 10, 942-949, doi: 10.1038/nm1093 (2004).

Denton, A. E. et al. Type I interferon induces CXCL13 to support ectopic germinal center formation. *J Exp Med* 216, 621-637, doi: 10.1084/jem.20181216 (2019).

Di Caro, G. et al. Occurrence of tertiary lymphoid tissue is associated with T-cell infiltration and predicts better prognosis in early-stage colorectal cancers. *Clin Cancer Res* 20, 2147-2158, doi: 10.1158/1078-0432.CCR-13-2590 1078-0432.CCR-13-2590 [pii] (2014).

Dieu-Nosjean, M. C. et al. Tertiary lymphoid structures, drivers of the anti-tumor responses in human cancers. *Immunol Rev* 271, 260-275, doi: 10.1111/imr.12405 (2016).

Figueiro, F. et al. Phenotypic and functional characteristics of CD39high human regulatory B cells (Breg). *Oncoimmunology* 5, e1082703, doi: 10.1080/2162402X.2015.1082703 1082703 [pii] (2016).

Gelabert-Baldrich, M. et al. Dynamics of KRas on endosomes: involvement of acidic phospholipids in its association. *FASEB J* 28, 3023-3037, doi: 10.1096/fj.13-241158 (2014).

Gu-Trantien, C. et al. CXCL13-producing TFH cells link immune suppression and adaptive memory in human breast cancer. *JCI Insight* 2, doi: 10.1172/jci.insight.91487 (2017).

Hamanishi, J. et al. Programmed cell death 1 ligand 1 and tumor-infiltrating CD8+T lymphocytes are prognostic factors of human ovarian cancer. *Proc Natl Acad Sci USA* 104, 3360-3365 (2007).

Hamanishi, J., Mandai, M. & Konishi, I. Immune checkpoint inhibition in ovarian cancer. *Int Immunol* 28, 339-348, doi: 10.1093/intimm/dxw020 dxw020 [pii] (2016).

Havenar-Daughton, C. et al. CXCL13 is a plasma biomarker of germinal center activity. *Proc Natl Acad Sci USA* 113, 2702-2707, doi: 10.1073/pnas.1520112113 (2016).

Helmink, B. A. et al. B cells and tertiary lymphoid structures promote immunotherapy response. *Nature* 577, 549-555, doi: 10.1038/s41586-019-1922-8 (2020).

Hiraoka, N. et al. Intratumoral tertiary lymphoid organ is a favourable prognosticator in patients with pancreatic cancer. *Br J Cancer* 112, 1782-1790, doi: 10.1038/bjc.2015.145 bjc2015145 [pii] (2015).

Huarte, E. et al. Depletion of dendritic cells delays ovarian cancer progression by boosting antitumor immunity. *Cancer Res* 68, 7684-7691, doi: 0008-5472.CAN-08-1167 [pii] 10.1158/0008-5472.CAN-08-1167 (2008).

Huarte, E. et al. PILAR is a novel modulator of human T-cell expansion. *Blood* 112, 1259-1268 (2008).

Hung, C. F., Tsai, Y. C., He, L. & Wu, T. C. Control of mesothelin-expressing ovarian cancer using adoptive transfer of mesothelin peptide-specific CD8+ T cells. *Gene Ther* 14, 921-929, doi: 10.1038/sj.gt.3302913 (2007).

Hunziker, W., Whitney, J. A. & Mellman, I. Selective inhibition of transcytosis by brefeldin A in MDCK cells. *Cell* 67, 617-627 (1991).

Jinushi, M., Hodi, F. S. & Dranoff, G. Therapy-induced antibodies to MHC class I chain-related protein A antagonize immune suppression and stimulate antitumor cytotoxicity. *Proc Natl Acad Sci USA* 103, 9190-9195, doi: 10.1073/pnas.0603503103 (2006).

Kroeger, D. R., Milne, K. & Nelson, B. H. Tumor-Infiltrating Plasma Cells Are Associated with Tertiary Lymphoid Structures, Cytolytic T-Cell Responses, and Superior Prognosis in Ovarian Cancer. *Clin Cancer Res* 22, 3005-3015, doi: 10.1158/1078-0432.CCR-15-2762 1078-0432.CCR-15-2762 [pii] (2016).

Kryczek, I. et al. B7-H4 expression identifies a novel suppressive macrophage population in human ovarian carcinoma. *J Exp Med* 203, 871-881 (2006).

Labidi-Galy, S. I. et al. High grade serous ovarian carcinomas originate in the fallopian tube. *Nat Commun* 8, 1093, doi: 10.1038/s41467-017-00962-1 (2017).

Ladanyi, A. et al. Density of DC-LAMP(+) mature dendritic cells in combination with activated T lymphocytes infiltrating primary cutaneous melanoma is a strong independent prognostic factor. *Cancer Immunol Immunother* 56, 1459-1469, doi: 10.1007/s00262-007-0286-3 (2007).

Lee, K. E. et al. Hif1a Deletion Reveals Pro-Neoplastic Function of B Cells in Pancreatic Neoplasia. *Cancer Discov* 6, 256-269, doi: 10.1158/2159-8290.CD-15-0822 (2016).

Li Chew, C. et al. In Vivo Role of INPP4B in Tumor and Metastasis Suppression through Regulation of PI3K-AKT Signaling at Endosomes. *Cancer Discov* 5, 740-751, doi: 10.1158/2159-8290.CD-14-1347 (2015).

Mazanec, M. B., Kaetzel, C. S., Lamm, M. E., Fletcher, D. & Nedrud, J. G. Intracellular neutralization of virus by immunoglobulin A antibodies. *Proc Natl Acad Sci USA* 89, 6901-6905 (1992).

McMullen, T. P., Lai, R., Dabbagh, L., Wallace, T. M. & de Gara, C. J. Survival in rectal cancer is predicted by T cell infiltration of tumour-associated lymphoid nodules. *Clin Exp Immunol* 161, 81-88, doi: 10.1111/j.1365-2249.2010.04147.x CEI4147 [pii] (2010).

Messina, J. L. et al. 12-Chemokine gene signature identifies lymph node-like structures in melanoma: potential for patient selection for immunotherapy? *Sci Rep* 2, 765, doi: 10.1038/srep00765 (2012).

Montfort, A. et al. A Strong B-cell Response Is Part of the Immune Landscape in Human High-Grade Serous Ovarian Metastases. *Clin Cancer Res* 23, 250-262, doi: 10.1158/1078-0432.CCR-16-0081 (2017).

Murphy, J. E., Padilla, B. E., Hasdemir, B., Cottrell, G. S. & Bunnett, N. W. Endosomes: a legitimate platform for the signaling train. *Proc Natl Acad Sci USA* 106, 17615-17622, doi: 10.1073/pnas.0906541106 (2009).

Mysona, D. et al. A combined score of clinical factors and serum proteins can predict time to recurrence in high grade serous ovarian cancer. *Gynecol Oncol* 152, 574-580, doi: 10.1016/j.ygyno.2018.12.015 (2019).

Nielsen, J. S. et al. CD20+ tumor-infiltrating lymphocytes have an atypical CD27-memory phenotype and together with CD8+ T cells promote favorable prognosis in ovarian cancer. *Clin Cancer Res* 18, 3281-3292, doi: 10.1158/1078-0432.CCR-12-0234 1078-0432.CCR-12-0234 [pii] (2012).
Park, B. V. et al. TGFbeta1-Mediated SMAD3 Enhances PD-1 Expression on Antigen-Specific T Cells in Cancer. *Cancer Discov* 6, 1366-1381, doi: 10.1158/2159-8290.CD-15-1347 (2016).
Patterson, K. I., Brummer, T., O'Brien, P. M. & Daly, R. J. Dual-specificity phosphatases: critical regulators with diverse cellular targets. *Biochem J* 418, 475-489, doi: 10.1042/bj20082234 (2009).
Perales-Puchalt, A. et al. Follicle-Stimulating Hormone Receptor Is Expressed by Most Ovarian Cancer Subtypes and Is a Safe and Effective Immunotherapeutic Target. *Clin Cancer Res* 23, 441-453, doi: 10.1158/1078-0432.CCR-16-0492 (2017).
Petitprez, F. et al. B cells are associated with survival and immunotherapy response in sarcoma. *Nature* 577, 556-560, doi: 10.1038/s41586-019-1906-8 (2020).
Rasoulouniriana, D. et al. A distinct subset of FcgammaRI-expressing Th1 cells exert antibody-mediated cytotoxic activity. *J Clin Invest* 129, 4151-4164, doi: 10.1172/JCI127590 (2019).
Redjimi, N. et al. NY-ESO-1-specific circulating CD4+ T cells in ovarian cancer patients are prevalently T(H)1 type cells undetectable in the CD25+ FOXP3+ Treg compartment. *PLOS One* 6, e22845, doi: 10.1371/journal-.pone.0022845 PONE-D-11-05345 [pii] (2011).
Robbins, P. F. et al. Tumor regression in patients with metastatic synovial cell sarcoma and melanoma using genetically engineered lymphocytes reactive with NY-ESO-1. *J Clin Oncol* 29, 917-924, doi: 10.1200/JCO.2010.32.2537 (2011).
Romanska, H. M. & Berditchevski, F. Tetraspanins in human epithelial malignancies. *J Pathol* 223, 4-14, doi: 10.1002/path.2779 (2011).
Rutkowski, M. R. et al. Microbially driven TLR5-dependent signaling governs distal malignant progression through tumor-promoting inflammation. *Cancer Cell* 27, 27-40, doi: 10.1016/j.ccell.2014.11.009 S1535-6108 (14) 00460-7 [pii] (2015).
Sato, E. et al. Intraepithelial CD8+ tumor-infiltrating lymphocytes and a high CD8+/regulatory T cell ratio are associated with favorable prognosis in ovarian cancer. *Proc Natl Acad Sci USA* 102, 18538-18543 (2005).
Sautes-Fridman, C., Petitprez, F., Calderaro, J. & Fridman, W. H. Tertiary lymphoid structures in the era of cancer immunotherapy. *Nat Rev Cancer*, doi: 10.1038/s41568-019-0144-6 (2019).
Scarlett, U. K. et al. In situ stimulation of CD40 and Toll-like receptor 3 transforms ovarian cancer-infiltrating dendritic cells from immunosuppressive to immunostimulatory cells. *Cancer Res* 69, 7329-7337, doi: 0008-5472.CAN-09-0835 [pii] 10.1158/0008-5472.CAN-09-0835 (2009).
Scarlett, U. K. et al. Ovarian cancer progression is controlled by phenotypic changes in dendritic cells. *J Exp Med* 209, 495-506, doi: jem.20111413 [pii] 10.1084/jem.20111413 (2012).
Schwartz-Cornil, I., Benureau, Y., Greenberg, H., Hendrickson, B. A. & Cohen, J. Heterologous protection induced by the inner capsid proteins of rotavirus requires transcytosis of mucosal immunoglobulins. *J Virol* 76, 8110-8117 (2002).
Shalapour, S. et al. Inflammation-induced IgA+ cells dismantle anti-liver cancer immunity. *Nature* 551, 340-345, doi: 10.1038/nature24302 (2017).
Shen, M., Sun, Q., Wang, J., Pan, W. & Ren, X. Positive and negative functions of B lymphocytes in tumors. *Oncotarget*, doi: 10.18632/oncotarget.10094 10094 [pii] (2016).
Stavnezer, J. & Kang, J. The surprising discovery that TGF beta specifically induces the IgA class switch. *J Immunol* 182, 5-7 (2009).
Stephen, T. L. et al. SATB 1 Expression Governs Epigenetic Repression of PD1 in Tumor-Reactive T Cells. *Immunity* 46, 51-64, doi: 10.1016/j.immuni.2016.12.015 (2017).
Stephen, T. L. et al. Transforming Growth Factor beta-Mediated Suppression of Antitumor T Cells Requires FoxP1 Transcription Factor Expression. *Immunity* 41, 427-439, doi: 10.1016/j.immuni.2014.08.012 S1074-7613 (14) 00306-9 [pii] (2014).
Teillaud, J. L. & Dieu-Nosjean, M. C. Tertiary Lymphoid Structures: An Anti-tumor School for Adaptive Immune Cells and an Antibody Factory to Fight Cancer? *Front Immunol* 8, 830, doi: 10.3389/fimmu.2017.00830 (2017).
Tesone, A. J. et al. Satb1 Overexpression Drives Tumor-Promoting Activities in Cancer-Associated Dendritic Cells. *Cell Rep* 14, 1774-1786, doi: 10.1016/j.celrep.2016.01.056 (2016).
Turula, H. & Wobus, C. E. The Role of the Polymeric Immunoglobulin Receptor and Secretory Immunoglobulins during Mucosal Infection and Immunity. *Viruses* 10, doi: 10.3390/v10050237 (2018).
Wirsing, A. M., Rikardsen, O. G., Steigen, S. E., Uhlin-Hansen, L. & Hadler-Olsen, E. Characterisation and prognostic value of tertiary lymphoid structures in oral squamous cell carcinoma. *BMC Clin Pathol* 14, 38, doi: 10.1186/1472-6890-14-38 1472-6890-14-38 [pii] (2014).
Wu, X. et al. Combined Anti-VEGF and Anti-CTLA-4 Therapy Elicits Humoral Immunity to Galectin-1 Which Is Associated with Favorable Clinical Outcomes. *Cancer Immunol Res* 5, 446-454, doi: 10.1158/2326-6066.CIR-16-0385 (2017).
Xiao, X. et al. PD1hi Identifies a Novel Regulatory B-cell Population in Human Hepatoma That Promotes Disease Progression. *Cancer Discov* 6, 546-559, doi: 10.1158/2159-8290.CD-15-1408 2159-8290.CD-15-1408 [pii] (2016).
Yokokawa, J. et al. Identification of novel human CTL epitopes and their agonist epitopes of mesothelin. *Clin Cancer Res* 11, 6342-6351, doi: 11/17/6342 [pii] 10.1158/1078-0432.CCR-05-0596 (2005).
Zhang, L. et al. Intratumoral T cells, recurrence, and survival in epithelial ovarian cancer. *N Engl J Med* 348, 203-213 (2003).
Zou, W. et al. Stromal-derived factor-1 in human tumors recruits and alters the function of plasmacytoid precursor dendritic cells. *Nat Med* 7, 1339-1346, doi: 10.1038/nm1201-1339 nm1201-1339 [pii] (2001).

---

What is claimed is:

1. An isolated programmed cell death protein 1 (PD1) binding molecule comprising a heavy chain variable domain and a light chain variable domain;

wherein the heavy chain variable domain comprises:

(a) a complementarity determining region (CDR) 1 (CDR1) as set forth in SEQ ID NO: 3;

(b) a CDR2 as set forth in SEQ ID NO: 4; and (c) a CDR3 as set forth in SEQ ID NO: 5;

wherein the light chain variable domain comprises:

(e) a CDR1 as set forth in SEQ ID NO: 6;

(f) a CDR2 as set forth in SEQ ID NO: 7; and (g) a CDR3 as set forth in SEQ ID NO: 8.

2. The isolated PD1 binding molecule of claim 1, wherein the heavy chain variable domain comprises the sequence as set forth in SEQ ID NO: 1.

3. The isolated PD1 binding molecule of claim 1, wherein the light chain variable domain comprises the sequence as set forth in SEQ ID NO: 2.

4. The isolated PD1 binding molecule of claim 1, wherein the binding molecule is an antibody.

5. The isolated PD1 binding molecule of claim 1, wherein the binding molecule is an immunotoxin.

6. A method of treating cancer or cancer-related diseases of cell proliferation in a subject in need thereof, comprising administering to the subject a therapeutically effective amount of any of the PD1 binding molecules of claim 1.

7. The isolated PD1 binding molecule of claim 1, wherein the heavy chain variable domain is encoded by a nucleic acid sequence as set forth in SEQ ID NO: 9, or a nucleic acid sequence at least about 95% identical thereto.

8. The isolated PD1 binding molecule of claim 1, wherein the light chain variable domain is encoded by a nucleic acid sequence as set forth in SEQ ID NO: 10, or a nucleic acid sequence at least about 95% identical thereto.

9. An anti-PD1 antibody comprising a heavy chain variable region as set forth in SEQ ID NO: 1, and a light chain variable region as set forth in SEQ ID NO: 2.

10. A method of treating cancer or cancer-related diseases of cell proliferation in a subject need thereof, comprising administering to the subject a therapeutically effective amount of any of the anti-PD1 antibodies of claim 9.

11. The anti-PD1 antibody of claim 9, wherein the heavy chain variable domain is encoded by a nucleic acid sequence as set forth in SEQ ID NO: 9, or a nucleic acid sequence at least about 95% identical thereto.

12. The anti-PD1 antibody of claim 9, wherein the light claim variable domain is encoded by a nucleic acid sequence as set forth in SEQ ID NO: 10, or a nucleic acid sequence at least about 95% identical thereto.

* * * * *